United States Patent

Devlin et al.

[11] Patent Number: 6,080,516
[45] Date of Patent: Jun. 27, 2000

[54] FLUORESCENT COMPOSITIONS AND THEIR USE

[75] Inventors: Brian Gerrard Devlin, Takarazuka; Junji Otani, Kobe; Kazuhiko Kunimoto, Takatsuki; Takashi Deno, Nishinomiya, all of Japan; Abul Iqbal, Arconciel; Sameer Hosam Eldin, Courtepin, both of Switzerland

[73] Assignee: Ciba Specialty Chemicals Corporation, Tarrytown, N.Y.

[21] Appl. No.: 09/017,870

[22] Filed: Feb. 3, 1998

[51] Int. Cl.[7] .............................. G03F 9/00; C08K 5/00; G03C 5/56
[52] U.S. Cl. .......................... 430/17; 106/494; 430/322
[58] Field of Search .......................... 106/494; 430/17, 430/322

[56] References Cited

U.S. PATENT DOCUMENTS 5,856,508  1/1999  Jaffe et al. ........................... 548/301.7

FOREIGN PATENT DOCUMENTS

| | | |
|---|---|---|
| 0456609 | 11/1991 | European Pat. Off. . |
| 2292947 | 3/1996 | United Kingdom . |
| 9323492 | 11/1993 | WIPO . |
| 9415441 | 7/1994 | WIPO . |

OTHER PUBLICATIONS

J. Appl. Phys. 65(9), May 1989, pp. 3610–3616 "Electroluminescence of Doped Organic Thin Films".
Harris et al, ACS Symp. Ser. 132, (1980) pp. 39–45.
Z. Physik, 17 (1923), 202–212.
Hebd. Seances Acad. Sci., 189, (1929), 1213–1216.
Z. Physik. Chem., 1 (1954), 275–277.
Anal. Biochem., 198, (1911), 308–311.

*Primary Examiner*—Janet Baxter
*Assistant Examiner*—Sin J. Lee
*Attorney, Agent, or Firm*—David R. Crichton

[57] ABSTRACT

Solid-state fluorescent composition comprising at least one host chromophore selected from the group consisting of a benzo[4,5] imidazo[2,1-a]isoindol-11-ones and an effective amount of at least one guest chromophore, and if desired a polymer C, wherein the emission spectrum of the host chromophore overlaps with the absorption spectrum of the guest chromophore, and wherein (a1) the host chromophore is covalently linked to a polymer backbone A ("host polymer"), and/or (a2) the guest chromophore is covalently linked to a polymer backbone B ("guest polymer").

9 Claims, No Drawings

FLUORESCENT COMPOSITIONS AND THEIR USE

The present invention relates to a solid composition comprising at least one host-chromophore selected from the group consisting of a benzo[4,5] imidazo[2,1-a]isoindol-11-ones and an effective amount of at least one guest chromophore, and if desired a polymer C, wherein the emission spectrum of the host chromophore overlaps with the absorption spectrum of the guest chromophore, and wherein (a1) the host chromophore is covalently linked to a polymer backbone A ("host polymer"), and/or (a2) the guest chromophore is covalently linked to a polymer backbone B ("guest polymer").

Further, the present invention relates to a process for the preparation of the inventive composition and its use as fluorescent materials.

In EP-A-0 456 609 is disclosed a process for the preparation of 1,2,3,4-tetrachlorobenzo-[4,5]imidazo[2,1-a] isoindol-11-one and its derivatives in the presence of selected solvents. They are pigments showing solid state fluorescence and improved outdoor durability. It is also mentioned that the combination of 95% 1,2,3,4-benzo[4,5] imidazo[2,1-a]isoindol-11-one with 5% of Indanthrone Blue generates a green fluorescent pigment. Hence, such a system is a pigment composite, wherein the new color generated is simply a sum of the two component colors rather than a new color generated by an energy transfer process.

F. W. Harris et.al. describe in ACS Symp. Ser. 132, 39 (1980) the compound 1,2,3,4-tetraphenyl-benzo[4,5] imidazo[2,1-a]isoindol-11-one as a model material, as a part of their investigations into phenylated polyimidazopyrrolones for potential use in aerospace applications. However, no reference to its fluorescence behavior is made.

Historically, observations of energy transfer and sensitized luminescence were made as early as 1923 by Cario and Frank, who conducted experiments that employed mercury and thallium in the vapor phase, Z. PHYZIK 17, 202 (1923).

In the years to follow J. Perrin and C. R. Choucroun made qualitative observations of energy transfer in solution, HEBD. SEANCES ACAD. SCI., 189, 1213 (1929).

Despite some studies being done in the interim years, it very much remains the acclaimed work of Th. Förster that most fully described, in quantitative terms, the phenomena, mechanisms and parameters of energy transfer specific to sensitized luminescence e.g. Z. PHYZIK CHEM., 1, 275 (1954). Moreover, it was Förster who brought the field of sensitized luminescence to a much wider forum, and subsequently sparked a broader interest which has lead to the concept being employed in a wide range of applications.

For example, in the area of electroluminescence, Tang et. al. demonstrated the usefulness of sensitized luminescence to create extremely bright electroluminescent devices (J. APPL. PHYS. 65(9), 3610 (1989)).

Also, in the field of biological diagnostics, sensitized luminescence is well established as a ubiquitous and highly sensitive tool to detect specifically targeted biological molecules, such as nucleic acids or antigens e.g. Verner et. al. ANAL. BIOCHEM. 198, 308 (1991).

Brinkley et. al. disclosed polymeric materials that employ sensitized luminescence to detect biological molecules, such as DNA and RNA, and can also be utilized in flow cytometry and analytical microscopy techniques (WO 93/23492). In the patent application by Brinkley et. al. (WO 93/23492), the usefulness of fluorescent polymeric beads in biological diagnostics is disclosed. However, no compositions comprising host chromophores and guest chromophores, as mentioned above are disclosed, and no hints are provided to the usefulness of such compositions outside the field of specific biological applications.

Hence, the object of the present invention was to provide a solid-state fluorescent composition with host chromophore based on a benzo[4,5] imidazo[2,1-a]isoindol-11-one, which does not show the abovementioned disadvantages, preferably a composition should be provided in which i) an intense solid state fluorescence is imparted, preferably wherein the emission wavelengths are in the in the visible region of the electromagnetic spectrum, ii) high ratios of host and guest molecules can be incorporated as part of the polymer whilst retaining solid-state fluorescence properties (i.e. negligible concentration quenching), iii) the material can be excited using wavelengths in both the UV and visible regions, iv) very excellent photostabilities can be achieved, v) a wide range emission wavelengths can be achieved through selection of guest molecules ("color tuning"), vi) a high thermal stability can be achieved, vii) soluble and insoluble fluorescent compositions can be generated, viii) migration of fluorescent host and guest molecules preferably is excluded and ix) ease preparation for the materials i.e. single pot reactions are possible.

Accordingly, a solid composition was found comprising at least one host chromophore selected from the group consisting of a benzo[4,5] imidazo[2,1-a]isoindol-11-ones and an effective amount of at least one guest chromophore, and if desired a polymer C, wherein the emission spectrum of the host chromophore overlaps with the absorption spectrum of the guest chromophore, and wherein (a1) the host chromophore is covalently linked to a polymer backbone A ("host polymer"), and/or (a2) the guest chromophore is covalently linked to a polymer backbone B ("guest polymer")

In addition, a process for the preparation of the inventive composition and its use as fluorescent materials were found, too.

A first embodiment object of the instant invention relates to a solid composition comprising at least one host chromophore selected from the group consisting of a benzo[4,5] imidazo[2,1-a]isoindol-11-ones and an effective amount of at least one guest chromophore, and if desired a polymer C, wherein the emission spectrum of the host chromophore overlaps with the absorption spectrum of the guest chromophore, and wherein (a1) the host chromophore is covalently linked to a polymer backbone A ("host polymer"), and/or (a2) the guest chromophore is covalently linked to a polymer backbone B ("guest polymer").

This means that the solid composition either comprises a host chromophore which is covalently linked to a polymer backbone A (referred to as "host polymer") or comprises a guest chromophore which is covalently linked to a polymer backbone B (hereinafter referred to as "guest polymer") or comprises a host chromophore which is covalently linked to a polymer backbone A and a guest chromophore which is covalently linked to a polymer backbone B (the latter then being called usually a blend or mix of two polymers).

In the context of this invention, the meaning of the overlap of the absorption spectrum of the guest chromophore with the fluorescence emission spectrum of the host chromophore, is clear to a skilled person in this field. However, to facilitate the understanding to others, overlap means "spectral overlap" defined by the following integral $$S = \int_0^{+\infty} f_F(v) f_A(v) dv$$

wherein $f_F(v)$ is normalized, so that $\int_0^{+\infty} f_F(v) dv$ is equal to fluorescence quantum yield of the host, and where $v$ is the wave number, $f_F$ the fluorescence spectrum of the host measured in quanta, and $f_A$ the spectral distribution of the molar extinction coefficient of the guest. The spectral overlap to realize photoluminescence enhancement usually is greater than 10, preferably greater than 100, more preferably greater than 500. An upper limit makes no sense, because the quantity "overlap" has no maximum (i.e. the larger, the better).

In a preferred embodiment, the inventive solid composition is characterized in that (a1) the guest chromophore is homogeneously distributed, preferred dissolved and homogeneously distributed, in a matrix formed by the host polymer, or (a2) the host chromophore is homogeneously distributed, preferred dissolved and homogeneously distributed, in a matrix formed by the guest polymer, or (b) the host polymer and the guest polymer are admixed, preferably homogeneously.

In the context of this invention, the term "homogeneously" means that molecules are evenly or uniformly distributed or dispersed throughout a mixture or a polymer matrix, and, preferably in the ideal case are essentially equidistant from each other. According to observations today, the more even or uniform the distribution is, the better are the fluorescence properties. Furthermore, a homogeneous or even distribution is preferred, because usually the chances for aggregation are decreased.

In the context of this invention, the term "dissolved" means that a molecule exists as a free and isolated entity in a given surrounding or matrix, preferably in such a way, that it is disengaged from any interactions between molecules of the same species, i.e. it is entirely surrounded by matrix molecules. Usually the matrix can be a liquid organic solvent or a solid material such as a polymer or another fluorescent material (host), which possesses a different chemical structure. The concentration limits for molecules in the dissolved state in general depend strongly on the associative nature between the molecule and the matrix medium, and/or the intrinsic cohesive forces that exist between the guest molecules in question. Correspondingly, it is impossible to define universal ranges for preferred concentrations, and therefore, usually must be treated on an ad hoc basis, e.g. by a few simple experiments.

In a further preferred embodiment a solid composition comprising of at least one host chromophore and an effective amount of at least one guest chromophore, wherein the emission wavelengths range of the host at least partially overlaps the absorption wavelengths range of the guest, characterised in that (a1) the host chromophore is covalently linked to a polymer backbone and the guest chromophore is dissolved and homogeneously distributed therein; or (a2) the guest chromophore is covalently linked to a polymer backbone and the host chromophores is dissolved and homogeneously distributed therein; or (b) both the host chromophore and the guest chromophore are covalently linked to different polymer backbones, the polymers are admixed and homogeneously distributed; and wherein the host chromophore is selected from the group consisting of a benzo[4,5] imidazo[2,1-a] isoindol-11-ones.

Under the aspects of the invention "host chromophore" means a fluorescent molecule or a fluorescent moiety, preferably selected from or derived from the group of solid-state fluorescent organic compounds like dyes, pigments and their derivatives, such that upon exposure to appropriate radiation wavelengths in the UV and/or daylight regions they absorb energy. This energy is in turn transferred, preferably almost quantitatively, in a resonant manner, to the guest chromophore. In this invention "fluorescent molecule as a host chromophore" is also referred to as host molecule or host monomer. "Fluorescent moiety as a host chromophore" is also referred to as host moiety. Host chromophores covalently linked to polymer backbones are host moieties whilst dissolved host chromophores are free, nonpolymeric host molecules.

Fluorescent molecules as host chromophores used for the composition (a2) according to the invention are preferably sufficiently soluble in the preparation medium, such that they can facilitate themselves to take part in the formation of the composition. Less soluble host chromophores may also be used, however this may require special apparatus to continuously dissolve the host compound into the reaction medium. Solubility may be imparted by the choice of core structures, substituents, functional groups and/or the length of spacers for the functional groups.

The structures containing fluorescent moieties as host chromophores used for the preparation of the compositions (host polymer alone or in admixture with guest polymer) according to the invention are preferably sufficiently soluble in a reaction medium, such that they readily facilitate themselves to be polymerized; or be covalently linked, via chemical reaction, to a polymer backbone or substrate surface. The reaction medium can be comonomers or an appropriate solvent. A less soluble host structure can be used, however this may require special apparatus to continuously dissolve the host compound into the reaction medium. Solubility may be imparted by the choice of core structures, substituents, functional groups and/or the length of spacers for the functional groups.

Under the aspects of the invention, guest chromophore means fluorescent molecules or fluorescent moieties which possess an absorption region that is at least partially overlapping with the emission region of the respective host in the system. Therein, the guest chromophores accept energy from host chromophore, and in turn emit the transferred energy as visible radiation, at wavelengths commensurate to the emission wavelengths of the same guest chromophore dissolved molecularly in a solvent. It is further required that the concentration of guest chromophore in the composition must be such they do not associate with one another to form localized guest domains, but in fact exist as isolated entities in the polymer bulk, as if they were dissolved molecularly. In this invention "fluorescent molecule as guest chromophore" is also referred to as guest molecule or guest monomer. "Fluorescent moiety as a guest chromophore" is also referred to as guest moiety. Guest chromophores covalently linked to polymer backbones are guest moieties whilst guest chromophores dispersed are guest molecules or guest monomers.

Fluorescent molecule as guest chromophores used for the composition (a1) according to the invention are preferably sufficiently soluble in the preparation medium, such that they can facilitate themselves to take part in the formation of the composition. Less soluble guest compounds may also be used, however this may require special apparatus to continuously dissolve the host compound into the reaction medium. Solubility may be imparted by the choice of core structures, substituents, functional groups and/or the length of spacers for the functional groups.

The fluorescent moiety as guest chromophore used for the preparation of the compositions (guest polymer alone or in admixture with the host polymer) according to the invention are preferably sufficiently soluble in a reaction medium, such that they readily facilitate themselves to be polymerized; or be covalently linked, via chemical reaction, to a polymer backbone or substrate surface. The reaction medium can be comonomers or an appropriate solvent. A less soluble guest structure can be used, however this may require special apparatus to continuously dissolve the monomer into the reaction medium. Solubility may be imparted by the choice of core structures, substituents, functional groups and/or the length of spacers for the functional groups.

The fluorescent hostguest composition of the present invention emits solid state fluorescence with a greatly enhanced emission intensity when compared to the solid-state emission intensity of the same composition in the absence of host chromophores, or the same composition in the absence of guest chromophores.

The term "enhancement factor" as used herein, is defined as the increased or decreased factor, in terms of peak height emission intensities of the solid composition of the instant invention compared to the corresponding host chromophore in the absence of the guest chromophore. Comparisons are considered real, for as long as the excitation radiation wavelengths are identical. Naturally however, the emission wavelengths of host/guest material occurs at longer wavelengths (lower energy) as compared to an identical material with no guest chromophore. Enhancement factors for the present invention are preferably all positive and particularly preferably should be at least 1.3, more preferably about at least 2 and most preferably at least 20.

The emission maximum of photoluminescence of the fluorescent polymers of this invention can be in the range from about 400 to about 800 nm, preferably about 420 to about 780 nm, more preferably about 420 to about 750 nm.

One embodiment (a1) of the present invention concerns a solid composition comprising at least one host chromophore selected from the group consisting of a benzo[4,5] imidazo [2,1-a]isoindol-11-ones and an effective amount of at least one guest chromophore, and if desired a polymer C, wherein the emission spectrum of the host chromophore overlaps with the absorption spectrum of the guest chromophore, and wherein the host chromophore is covalently linked to a polymer backbone A ("host polymer").

The fluorescent moiety as a host chromophore to be used in the composition (a1) is covalently linked, directly or via a bridging group, to a polymer backbone.

The bridging group may contain 1 to 60 atoms, preferably 1 to 30 atoms, and particularly preferred 1 to 20 atoms, selected from the group consisting of C, O, S and N. The bridging group especially preferred is a hydrocarbon residue, which may be interrupted with one or more and/or end-capped with one of the heteroatoms selected from the group consisting of O, S, N or the group C(O), and which preferably contain in total 1 to 40 atoms, more preferably 2 to 30 atoms and especially preferred 3 to 20 atoms.

The fluorescent moiety as a host chromophore covalently linked either directly or through a bridging group to the polymer backbone may be represented by the formula II

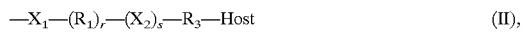

(II), wherein $X_1$ and $X_2$ each independently from one another mean a direct bond, or $X_1$ and $X_2$ each independently from one another mean —O—, —S—, —$NR_2$—, —C(O)—O—, —O—C(O)—, —O—C(O)—O—, —$SO_2$—O—, —O—$SO_2$—, —O—$SO_2$—O—, —$NR_2$—C(O)—, —C(O)—$NR_2$—, —$NR_2$—C(O)—O—, O—C(O)—$NR_2$—, —$NR_2$—C(O)—$NR_2$—, —$NR_2$—$SO_2$—, —$SO_2$—$NR_2$—, —$NR_2$—$SO_2$—O—, O—$SO_2$—$NR_2$— or —$NR_2$—$SO_2$—$NR_2$— each $R_1$ independently from one another mean a bivalent bridging group,

Host stands for a monovalent benzo[4,5] imidazo[2,1-a] isoindol-11-one derivative, $R_2$ each independently from one another is H, $C_1$–$C_{12}$alkyl, $C_5$- or $C_6$cycloalkyl, $C_5$- or $C_6$cycloalkylmethyl or -ethyl, phenyl, benzyl or 1-phenyl-2-ethyl, $R_3$ each independently from one another are a direct bond, $C_1$–$C_{18}$alkylene, $C_5$- or $C_6$cycloalkylene, $C_6$–$C_{10}$ arylene or $C_7$–$C_{12}$ aralkylene, r means the numbers 0 or 1 and s means the numbers 0 or 1, with the proviso that s is 0, if r is 0, and x means the numbers 0 or 1 and y means the numbers 0 or 1, with the proviso that y is 0, if x is 0.

In the context of alkyl, $R_2$ has preferably 1 to 6 and especially preferred 1 to 4 C-atoms. Some examples are methyl, ethyl, n- or i-propyl, butyl, pentyl, hexyl and octyl. In the context of cycloalkyl $R_2$ is preferably cyclohexyl, and in the context of cycloalkylmethyl, cyclohexylmethyl is preferred. In a preferred embodiment $R_2$ means H or $C_1$–$C_4$ alkyl.

The bivalent bridging group is preferably a hydrocarbon residue, which preferably contains 1 to 30, more preferably 2 to 20, most preferably 3 to 20 and particularly preferred 3 to 18 C-atoms, which is unsubstituted or one or more times substituted with $C_1$–$C_4$ alkyl, $C_1$–$C_4$ alkoxy or =O. The hydrocarbon residue may be also one or more times interrupted with heteroatoms selected from the group consisting of —O—, —S— and —$NR_2$—, whereby $R_2$ is preferably H or $C_1$–$C_4$ alkyl.

The bivalent bridging group can be $C_1$–$C_{20}$-, preferably $C_2$–$C_{12}$ alkylene, which may be linear or branched. Some examples are methylene, ethylene, 1,2- or 1,3-propylene, 1,2-, 1,3- or 1,4-butylene, pentylene, hexylene, octylene, dodecylene, tetradecylene, hexadecylene and octadecylene.

The bivalent bridging group can be polyoxyalkylene with 2 to 12, preferably 2 to 6 and more preferably 2 to 4 oxyalkylene units and 2 to 4, preferably 2 or 3 C-atoms in the alkylene moiety. Especially preferred is polyoxyethylene and polyoxypropylene with 2 to 6 oxyalkylene units.

The bivalent bridging group may be $C_5$–$C_{12}$, preferably $C_5$–$C_8$- and most preferably $C_5$- or $C_6$-cycloalkylene like for example cyclopentylene, cyclohexylene, cyclooctylene or cyclododecylene.

The bivalent bridging group may be $C_5$–$C_{12}$-, preferably $C_5$–$C_8$- and more preferably $C_5$- or $C_6$-cycloalkyl-$C_1$–$C_{12}$- alkylene and most preferably $C_5$- or $C_6$-cycloalkyl-$C_1$–$C_4$- alkylene. Some examples are -cyclopentyl-$C_nH_{2n}$— and -cyclohexyl-$C_nH_{2n}$—, wherein n means a number of 1 to 4. Especially preferred is -cyclohexyl-$CH_2$—.

The bivalent bridging group may be $C_5$–$C_{12}$-, preferably $C_5$–$C_8$- and more preferably $C_5$- or $C_6$-cycloalkane-($C_1$–$C_{12}$ alkylene)$_2$- and most preferably —($C_1$–$C_4$-alkylene)$_2$. Some examples are cyclopentane-($C_nH_{2n}$—)$_2$ and cyclohexane- ($C_nH_{2n}$—)$_2$, wherein n means a number of 1 to 4. Especially preferred is —$CH_2$-cyclohexane-$CH_2$—.

The bivalent bridging group may be $C_6$–$C_{14}$ arylene and preferably $C_6$–$C_{10}$ arylene, for example naphthylene or more preferably phenylene.

The bivalent bridging group may be $C_7$–$C_{20}$ aralkylene and preferably $C_7$–$C_{12}$ aralkylene. More preferred is arylene-$C_nH_{2n}$—, wherein arylene means naphthylene and preferably phenylene, and n means a number from 1 to 4. Examples are benzylene and phenylethylene.

The bivalent bridging group may be arene-($C_nH_{2n}$—)$_2$—, wherein arene is preferably naphthalene and more preferably benzene and n is a number from 1 to 4. Examples are xylylene and benzene($CH_2CH_2$)$_2$—.

$R_3$ contains as alkylene preferably 1 to 12 and more preferably 1 to 6 C-atoms. Especially preferred examples are methylene, ethylene, 1,2- or 1,3-propylene and 1,2-, 1,3- and 1,4-butylene. $R_3$ means as arylene preferably phenylene and as aralkylene preferably benzylene.

In a preferred embodiment the bridging group may be selected from the formula (IIa)

—C(O)—O—R'—O—C(O)—(R")—      (IIIa), wherein R' is $C_2$ to $C_{20}$, preferably $C_2$ to $C_{12}$, and more preferably $C_2$ to $C_6$ alkylene, phenylene, benzylene, or oligoxyalkylene with preferably 2 to 6, and more preferably 2 to 4 oxyethylene and/or oxypropylene units, and R" means a direct bond, $C_1$ to $C_{12}$ alkylene, phenylene or benzylene.

The monovalent benzo[4,5] imidazo[2,1-a]isoindol-11-one derivative may be represented by the general formulae (III) or (IIIa)

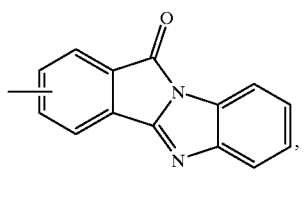
(III)

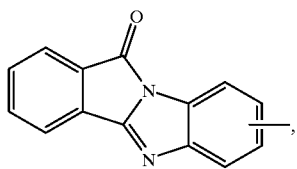
(IIIa)

wherein
   neighboring carbon atoms of the benzene rings can be condensed with benzene rings, heteroaromatic rings or both, and to these rings can be linked the functional group rather than to benzene rings of the core polycyclic structure,
   the aromatic rings are unsubstituted or substituted with F, Cl or Br, I, —CN, —$NO_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —$SO_2$, $C_3$ to $C_{12}$ cycloalkyl-SO— or —$SO_2$, $C_6$ to $C_{18}$ aryl-SO— or —$SO_2$, $C_5$ to $C_{17}$ heteroaryl-SO— or —$SO_2$, $C_3$ to $C_{12}$ cycloalkylalkyl-SO— or —$SO_2$, $C_6$ to $C_{18}$ aralkyl-SO— or —$SO_2$, $C_5$ to $C_{17}$ heteroaralkyl-SO— or —$SO_2$, secundary amino with 2 to 30 carbon atoms, and alkoxyalkyl with 2 to 20 carbon atoms.

The cyclic aliphatic and aromatic residues (substituents) may be also substituted, for example with halogens like F, Cl or Br; or —CN, —$NO_2$, $C_1$ to $C_{18}$ alkyl, $C_3$ to $C_{12}$ cycloalkyl, $C_6$ to $C_{18}$ aryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy $C_3$ to $C_{12}$cycloalkyloxy, $C_6$ to $C_{18}$ aryloxy. The substituent alkyl may be linear or branched and may be substituted with halogen like F or Cl.

Examples of substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-$SO_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 or 2 rings are condensed with the neighboring carbon atoms to form bicyclic or tricyclic systems. They may be selected from benzene, furan, thiophene, pyrrole, pyridine, and pyrimidine.

In a preferred embodiment the monovalent benzo[4,5] imidazo[2,1-a]isoindol-11-one derivative corresponds to formula (IIIb) or (IIIc),

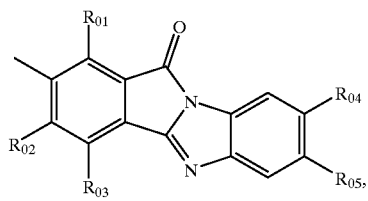
(IIIb)

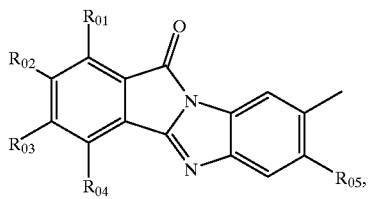
(IIIc)

wherein
   $R_{01}$, $R_{02}$, $R_{03}$, $R_{04}$, and $R_{05}$ independently from one another mean H, Cl, $C_1$ to $C_{18}$ alkyl, $C_1$ to $C_{18}$ alkoxy, phenyl, benzyl, $C_1$ to $C_{12}$ alkylphenyl or $C_1$ to $C_{12}$ alkylbenzyl.

$R_{05}$ in formula IIIc means preferably H. $R_{01}$, $R_{02}$, $R_{03}$ and $R_{04}$ are especially preferred H, phenyl, benzyl, $C_1$ to $C_{12}$ alkylphenyl or $C_1$ to $C_{12}$ alkylbenzyl and $R_{05}$ is especially preferred H.

Some preferred examples of fluorescent moieties as host chromophores corresponding to formula II are

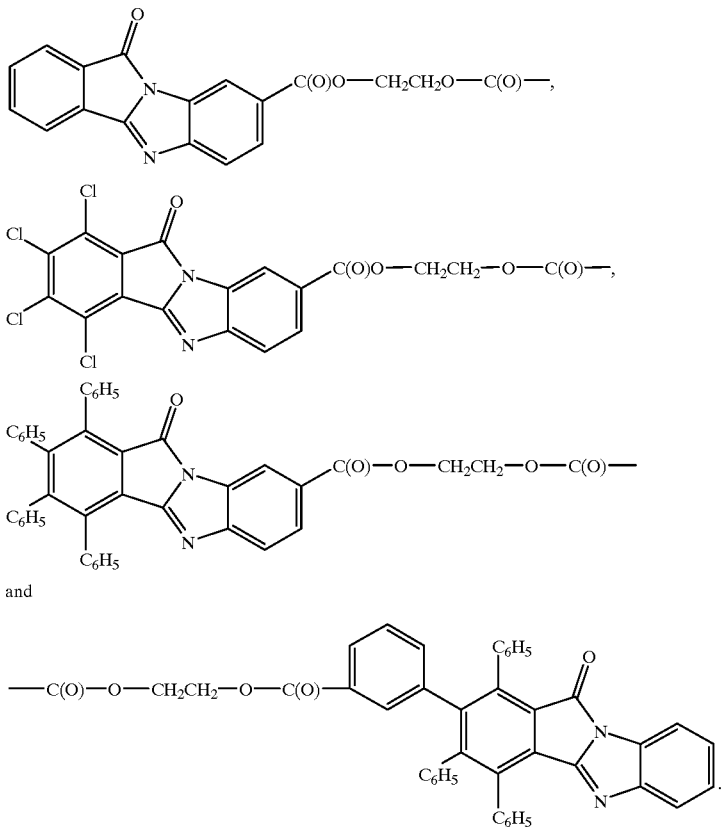

and

The fluorescent moieties as host chromophores are linked through functional groups bonded to structural units of the backbone. Examples of functional groups are —OH, —SH, —NHR$_2$, —CH=O, carboxylic acid, carboxylic acid ester, carboxylic acid amide, —SO$_3$H, epoxide, vinyl or isocyanate, wherein R$_2$ is preferably H or C$_1$ to C$_4$ alkyl.

The polymers can be selected from natural or synthetic polymers. Examples of natural polymers are polysaccharides like cellulose, starch or chitosane, which may be partially etherified by C$_1$–C$_4$ alkyl or esterified with C$_1$–C$_8$ acyl. Synthetic polymers with functional groups can be prepared in accordance with well known methods. Some examples of synthetic polymers are polyvinylalcohol and copolymers of vinyl alcohol with unsubstituted or substituted olefines as comonomers; polymethacrylic acid, polyacrylic acid and polymaleic acid and copolymers of methacrylic acid, acrylic acid and/or maleic acid with unsubstituted or substituted olefines as comonomers; polyhydroxyalkylacrylates, polyhydroxyalkylmethacrylates and polymaleic acid hydroxyalkylesters, and copolymers of hydroxyalkylesters of methacrylic acid, acrylic acid and/or maleic acid with unsubstituted or substituted olefins as comonomers; polyacrylamide and polymethacrylamide and copolymers of acryl amide, methacrylamide or both with unsubstituted or substituted olefins as comonomers; polyaminoalkylacrylates, -methacrylates and -maleic acid esters and copolymers of aminoalkylacrylates, -methacrylates, -maleic acid esters or two or three of these with unsubstituted or substituted olefins as comonomers; polyhydroxyalkyl- or polyaminoalkylvinylalcohol and copolymers of hydroxyalkylvinylether, aminoalkylvinylether or both with unsubstituted or substituted olefins as comonomers; hydroxylated polybutadienes from butadiene, isoprene or chloroprene and copolymers of butadiene, isoprene, chloroprene or two or three of these monomers with unsubstituted or substituted olefins as comonomers; hydroxy- or aminopolystyrene, chlormethylpolystyrene, and polystyrenesulfonic acid and copolymers of hydroxystyrene, aminostyrene, chloromethylstyrene, polystyrenesulfonic acid, or two or more of these monomers with unsubstituted or substituted olefins as comonomers; polyglycidyl ethers and hydroxyalkylated or aminoalkylated polyglycidyl ethers; and polyesters, polyamides and polyurethanes from hydroxylic group containing monomersFurther suitable vinyl polymers are polyvinylpyrrolidone, polyvinylimidazole and polyvinylpyridine and copolymers of vinylpyrrolidone, vinylimidazole, vinylpyridine or two or three of them together with unsubstituted or substituted olefins as comonomers. Suitable olefinic comonomers are for example ethene, propene, butene, pentene, octene, vinylchloride, vinylidenechloride, styrenes and acrylonitrile.

The polymer may also be composed of crosslinked polymers, for example polymerisates from olefins, optionally nonfunctionalized olefinic monomers, and di-olefinic monomers like butadiene, divinylbenzene or dioldiacrylates or dioldimethacrylates. The polymer may also be composed of thermosetting resins, for example epoxide resins, melamine-formaldehyde resins and phenol-formaldehyde resins.

The host moiety linked to the polymers may be derived from mono-functional or polyfunctional host molecules. Preferably the molecules are mono- to trifunctional, especially preferred are mono- or difunctional molecules.

A weight average molecular weight of the non-crosslinked polymers used in the present invention can be in the range from $10^3$ to $2\times10^6$, preferably, $10^4$ to $10^6$, more preferably, $2 \times 10^4$ to $10^6$, and most preferably $4 \times 10^4$ to $5 \times 10^5 \text{gmol}^{-1}$, as determined by gel permeation chromatography, using polystyrene standards as calibration.

The polymer may be composed of monomeric units with covalently linked monovalent to trivalent residues of a host chromophore and optionally of other comonomeric units.

The weight ratio of host chromophore structural units (k) to non-fluorescent structural units (n) is dependent on the actual practical application, hence there are no well defined preferred ratios, other than the broad range 100:0 to 1:999. In certain applications where both color strength and fluorescence are required, then the preferred ratios of chromophore structural units to non-luorescent structural units are 20:80 to 100:0, preferably 50:50 to 100:0 and more preferably 80:20 to 100:0. In circumstances where fluorescence is desired but color strength is not required, then the preferred ratio of chromophore structural units to non-fluorescent structural units are 20:80 to 1:999, more preferably 10:90 to 1:999 and more preferably 5:95 to 1:999.

The polymers may be composed of recurring structural units of formula (IV)

 (IV)

or may be composed of recurring crosslinking units of formula (IVa), alone or in combination with structural units of formula (IV)

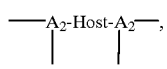 (IVa)

wherein

A is a trivalent organic residue, $A_2$ is a trivalent organic residue,

Host is a monovalent or divalent fluorescent moiety derived from a benzo[4,5]imidazo[2,1-a]isoindol-11-ones, as defined before, which is covalently linked, either directly or via a bridging group, whereby A and $A_2$ are copolymerisable when used in combination.

The polymer may additionally contain structural units of formula (IVb)

 (IVb)

wherein $A_4$ means the same or a different divalent residue copolymerizable with A and $A_2$.

A, $A_2$, and $A_4$ may be derived from monomers selected from the group consisting of olefins, polyolefines like di- or triolefines, polyalcohols like diols and triols, polyamines like diamines and triamines, polyisocyanates like di- or tri-isocyanates, polycarboxylic acids like di- and tricaboxylic acids, and polyepoxides like di- and triepoxides.

The weight ratio of chromophore structural units (IV)and (IVa) to non-fluorescent structural units (Ivb) is dependent on the actual practical application, hence there are no well defined preferred ratios, other than the broad range 100:0 to 1:999. In certain applications where both color strength and fluorescence are required, then the preferred ratios of chromophore structural units to non-fluorescent structural units are 20:80 to 100:0, preferably 50:50 to 100:0 and more preferably 80:20 to 100:0. In circumstances where fluorescence is desired but color strength is not required, then the preferred ratio of chromophore structural units to non-fluorescent structural units are 20:80 to 1:999, more preferably 10:90 to 1:999 and more preferably 5:95 to 1:999.

In a preferred embodiment the polymers according to the invention contain recurring structural units of formula (V) and optionally recurring structural units of formula (VI),

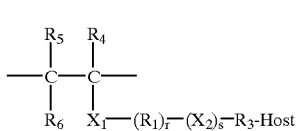 (V)

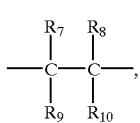 (VI)

wherein $X_1$ and $X_2$ each independently of one another mean a direct bond, or $X_1$ and $X_2$ each independently of one another mean —O—, —S—, —$NR_2$—, —C(O)—O—, —O—C(O)—, —O—C(O)—O—, —$SO_2$—O—, —O—$SO_2$—, —O—$SO_2$—O—, —$NR_2$—C(O)—, —C(O)—$NR_2$—, —$NR_2$—C(O)—O—, O—C(O)—$NR_2$—, —$NR_2$—C(O)—$NR_2$—, —$NR_2$—$SO_2$—, —$SO_2$—$NR_2$—, —$NR_2$—$SO_2$—O—, —O—$SO_2$—$NR_2$— or —$NR_2$—$SO_2$—$NR_2$—, $R_1$ means a bivalent bridging group, Host means a monovalent fluorescent moiety as a host chromophore selected from the group of benzo[4,5] imidazo[2,1-a]isoindol-11-ones, $R_2$ means H, $C_1$–$C_{12}$ alkyl, $C_5$- or $C_6$ cycloalkyl, $C_5$- or $C_6$ cycloalkylmethyl or -ethyl, phenyl, benzyl or 1-phenyl-2-ethyl, $R_3$ means a direct bond, $C_1$–$C_{18}$ alkylene, $C_5$- or $C_6$-cycloalkylene, $C_6$–$C_{10}$ arylene or $C_7$–$C_{12}$ aralkylene, r and s independently of one another mean the numbers 0 or 1, with the proviso that if s is 0, r is 0, $R_4$ and $R_5$ each independently of one another mean H, $C_1$–$C_6$ alkyl, $C_6$–$C_{10}$ aryl or $C_7$–$C_{12}$ aralkyl, $R_6$ means H or the group —C(O)O—$R_{11}$, $R_7$ means H, $C_1$–$C_6$ alkyl, $C_6$–$C_{10}$ aryl or $C_7$–$C_{12}$ aralkyl, $R_8$ means H, F, Cl, CN, $C_1$–$C_6$ alkyl or $C_6$–$C_{10}$ aryl, $R_9$ means H, $C_1$–$C_6$ alkyl or —C(O)O—$R_{11}$, $R_{10}$ means H, $C_1$–$C_6$ alkyl, $C_6$–$C_{10}$ aryl, $C_7$–$C_{12}$ aralkyl, imidazolyl, pyrrolidonyl, F, Cl, CN or the group —$X_1$—$(R_1)_r$—$(X_2)_s$—H, and $R_{11}$ means H, K, Na, $C_1$–$C_{18}$ alkyl, $C_1$–$C_{18}$ hydroxyalkyl, cyclohexyl, cyclopentyl, cyclohexylmethyl, phenyl, $C_1$–$C_4$ alkylphenyl, benzyl or $C_1$–$C_4$ alkylbenzyl.

For $X_1$, $X_2$, $R_1$, $R_2$, $R_3$, r, s and Host, the meanings and preferred embodiments are the same as previously described herein.

$R_4$ and $R_5$ as alkyl mean preferably $C_1$–$C_4$ alkyl, for example methyl, ethyl, n- or i-propyl and n-, i- or t-butyl; as aryl preferably naphthyl or phenyl; and as aralkyl preferably benzyl. Especially preferred $R_4$ is H and $R_5$ is H or methyl.

$R_6$ means preferably H, —C(O)OH or —C(O)O—$C_1$ to $C_4$-alkyl.

$R_7$ means as alkyl preferably $C_1$ to $C_4$ alkyl, for example methyl, ethyl, n- or i-propyl, and n-, i- or t-butyl; as aryl preferably naphthyl or phenyl and as aralkyl preferably benzyl. Especially preferred $R_7$ is H.

As alkyl $R_8$ means preferably $C_1$ to $C_4$ alkyl, for example methyl, ethyl, n- or i-propyl and n-, i- or t-butyl; and for aryl it is preferably phenyl or naphthyl. Especially preferred $R_8$ is H, Cl, CN, phenyl or $C_1$ to $C_4$ alkyl.

$R_9$ means as alkyl preferably $C_1$–$C_4$ alkyl, for example methyl, ethyl, n- or i-propyl and n-, i- or t-butyl. In the group —C(O)O—$R_{11}$, $R_{11}$ means preferably H or $C_1$–$C_{12}$ alkyl, more preferably $C_1$–$C_6$ alkyl, like for example methyl, ethyl, propyl, butyl, pentyl, hexyl, heptyl, octyl, nonyl, decyl, undecyl, dodecyl, tetradecyl, hexadecyl and octadecyl. Especially preferred $R_9$ is H, —C(O)OH or —C(O)—O—$C_1$–$C_4$ alkyl.

$R_{10}$ means as alkyl preferably $C_1$–$C_4$ alkyl, for example methyl, ethyl, n- or i-propyl and n-, i- or t-butyl, as aryl preferably phenyl and naphthyl, and as aralkyl preferably benzyl. $R_{10}$ means preferably H, $C_1$–$C_4$ alkyl, phenyl, pyrrolidonyl, F, Cl, CN or the group —$X_1$—$(R_1)_r$—$(X_2)_s$—H.

$R_{11}$ may be for example H, K, Na, $C_1$–$C_6$ alkyl, $C_1$–$C_6$-hydroxyalkyl, cyclohexyl, cyclopentyl, cyclohexylmethyl, phenyl, methylphenyl, benzyl or methylbenzyl.

The weight ratio of chromophore structural units (V) to non-fluorescent structural units VI is dependent on the actual practical application, hence there are no well defined preferred ratios, other than the broad range 100:0 to 1:999. In certain applications where both color strength and fluorescence are required, then the preferred ratios of chromophore structural units to non-fluorescent structural units are 20:80 to 100:0, preferably 50:50 to 100:0 and more preferably 80:20 to 100:0. In circumstances where fluorescence is desired but color strength is not required, then the preferred ratio of chromophore structural units to non-fluorescent structural units are 20:80 to 1:999, preferably 10:90 to 1:999, more preferably 5:95 to 1:999, most preferably 20:80 to 100:0, especially preferred 50:50 to 100:0, and particularly prefered 80:20 to 100:0.

The polymers with the structural elements of formulae (V) and optionally (VI) may be crosslinked in combination with multi-functional monomers, for example with 0.01 to 80 weight-%, preferably 0.1 to 60 weight-% of these monomers, related to 100 g of the polymer. Depending upon the kind of the polymer at least trifunctional carboxylic acids, isocyanates, alcohols, amines, vinyls or epoxides may be used. Furthermore residues containing at least two olefinically (ethylenically) unsaturated groups may be employed. The ethylenically unsaturated crosslinking agent may be selected from the group consisting of divinylbenzol, di-methylmaleinimide-alkylene like bi-(dimethylmaleinimidyle)-methylene or -ethylene, acrylic acid- or methacrylic acid esters or -amides of polyols, preferably diols to tetrols, or polyamines respectively, preferably diamines to tetramines.

Preferred ethylenically unsaturated crosslinking agents are selected from the group of acrylic or methacrylic acid esters of aliphatic, cycloaliphatic and cycloaliphatic-aliphatic diols to tetrols and diamines to tetramines containing especially preferred 2 to 12, and particularly preferred 2 to 8 C-atoms. Some examples of these diols are alkylenediols like ethylenglycol, 1,2- or 1,3-propanediol, 1,2-, 1,3- and 1,4-butanediol, pentanediol, hexanediol, octanediol, decanediol, dodecanediol, cyclohexanediol, di(hydroxymethyl)-cyclohexane, polyoxyalkylendiols from preferably $C_2$–$C_6$ alkylendiols with preferably 2 to 100 alkylenediol units, more preferably 2 to 50 alkylenediol units, and most preferably 2 to 20 alkylenediol units, like for example polyethylenediols, polypolypropylenediols, polybutylenediols and polyethylene/polypropylenediols, further 1,1,1-trihydroxymethylethane or -propane, pentaerythritol and dipentaerythritol. Some examples for polyamines are ethylenediamine, 1,3- and 1,3-propanediamine, 1,2-, 1,3- and 1,4-butanediamine, 1,6-hexanediamine, diethylenetriamine, triethylenetetramine, cyclohexanediamine, (aminomethyl)cyclohexaneamine, isophorondiamine and di-(aminomethyl)cyclohexane.

In a preferred embodiment of the invention the polymers contain structural elements of the formula (VII)

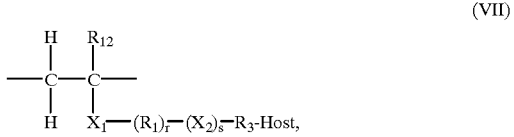

(VII)

wherein $R_{12}$ is H or methyl, and $X_1$, $X_2$, $R_1$, $R_3$, Host, r and s have the same meanings as described before, including the preferred embodiments; and optionally structural elements of formula VI.

The group —$X_1$—$(R_1)_r$—$(X_2)_s$—$R_3$— in the structural elements of formulae V and VII mean preferably —C(O)—O—, —C(O)—O—$C_2$–$C_6$ alkylene-O—C(O)—, —C(O)—O—($C_2$–$C_6$ alkylene-O)$_u$—C(O)— with u being a number from 2 to 10, —O—C(O)—$C_6H_5$—$CH_2$—, —O—C(O)—$C_6H_5$- or —O—C(O)—$C_1$ to $C_{12}$ alkylene.

The polymers with the structural elements of formulae (V) or (VII), and optionally structural elements of formula (VI) may contain additionally identical or different structural elements of formula (VIII)

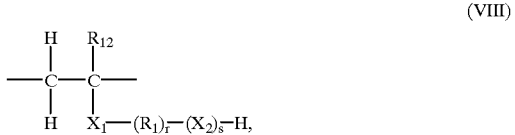

(VIII)

wherein $R_{12}$, $X_1$, $X_2$, $R_1$, r and s have the meanings given before, inclusive of the preferred embodiments. These structural elements are especially present when the groups Host are introduced to the polymer through reaction between pendant functional groups on the polymer and functional groups on the respective host and guest molecules.

The polymers with the structural elements of formulae (V) or (VII), and optionally structural elements of formula (VI), contain preferably same or different structural elements of formula (IX) as preferred units of formula (VI)

(IX)

wherein
  $R_{12}$ means H or methyl, and
  $R_{13}$ means H, $C_1$–$C_4$ alkyl, $C_1$–$C_4$ alkoxy, —CN, Cl, phenyl, pyrrolidonyl, pyridinyl, imidazolyl, —C(O)OR$_{14}$ or —C(O)—NR$_{15}$R$_{16}$,
  $R_{14}$ means H or $C_1$–$C_{18}$- and preferably $C_1$–$C_{12}$ alkyl, and
  $R_{15}$ and $R_{16}$ independently of one another mean H or $C_1$–$C_{12}$-, and preferably $C_1$–$C_6$ alkyl.

The polymers with the structural elements of formula (V) or (VII), and optionally identical or different structural elements of formula (VI) or formula (IX), may additionally contain structural elements of formulae (X) or (XI) as preferred units of crosslinking agents,

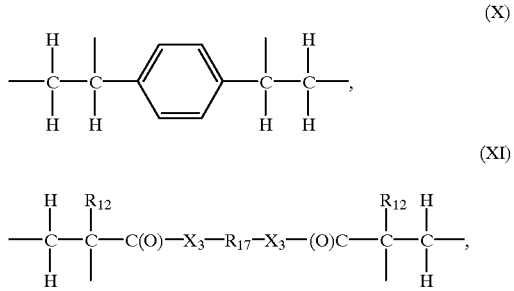

(X)

(XI)

wherein $R_{12}$ means H or methyl, $X_3$ means —O—, —NH— or —N($C_1$–$C_4$-alkyl)-, and $R_{17}$ means $C_2$–$C_{12}$- and preferably $C_1$–$C_6$ alkylene, cyclohexylene, cyclohexanedimethylene, phenylene, or $X_3$ means —O— and $R_{17}$ means $C_2$–$C_6$ alkylene-($C_2$–$C_6$ alkylen-O)$_{2\ to\ 20}$—$C_2$–$C_6$ alkylene.

The polymerisates and preferred polymerisates described before may contain additionally same or different ionic structural elements, for example (XII)

(XII)

wherein $R_{12}$ means H or methyl, $R_{18}$ means H and $R_{19}$ means —C(O)O$R_{20}$, —SO$_3R_{20}$, —$C_6H_4$—COO$R_{20}$, —$C_6H_4$—SO$_3R_{20}$, —$C_6H_4$—$R_{21}$ or —C(O)—$X_4$—$C_2$–$C_6$ alkylene-$R_{22}$, $X_4$ means —O— or —NH—, $R_{18}$ and $R_{19}$ mean independently of one another —C(O)O$R_{20}$ or —C(O)—$X_4$—$C_2$–$C_6$ alkylene-$R_{22}$, $R_{20}$ means an alkaline metal, preferably Li, Na or K, $R_{21}$ means an ammonium group or an ammoniummethyl group, and $R_{22}$ means an ammonium group.

The ammonium group or the ammonium in the ammoniummethyl group may be derived from primary, secondary or tertiary amine groups; preferred are quaternary ammonium groups. The ammonium groups or the ammonium in the ammoniummethyl group may correspond to the formula (XIII)

$$-^+NR_{23}R_{24}R_{25}$$ (XIII), wherein $R_{23}$, $R_{24}$ and $R_{25}$ are independently from one another H, $C_1$–$C_{18}$-, preferably $C_1$–$C_{12}$- and more preferably $C_1$–$C_6$ alkyl, $C_5$- or $C_6$cycloalkyl, phenyl, benzyl, 1-phenyl-2-ethyl, or $R_{23}$ and $R_{24}$ together are tetramethylene, pentamethylene or —CH$_2$CH$_2$—O—CH$_2$CH$_2$—;$R_{26}$ has the meaning as given before.

Suitable counter anions may be derived from inorganic or organic acids, like for example carboxylic acids, sulfonic acids and halogenhydrogen acids. Preferred counter anions are chloride and bromide.

The polymerisates and preferred polymerisates described before may contain additionally structural elements with acidic groups like for example —C(O)OH or —SO$_3$H, especially when emulsion polymerisates are involved.

The structural elements with acidic groups may correspond to the formula (XIV)

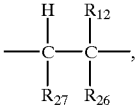

(XIV)

wherein $R_{12}$ means H or methyl, $R_{27}$ means H and $R_{26}$ means —C(O)OH, —SO$_3$H, —$C_6H_4$—COOH, —$C_6H_4$—SO$_3$H, or $R_{26}$ and $R_{27}$ means —C(O)OH.

Polymers with amino or acidic groups may be preferably soluble in water or they may be prepared by emulsion polymerization for dispersing and/or dissolving monomers. In another preferred embodiment the polymers according to the invention may be cross-linked with difunctional host and/or guest molecules. These polymers may contain recurring structural elements of formulae (XV), alone or together with structural elements of formula (V),

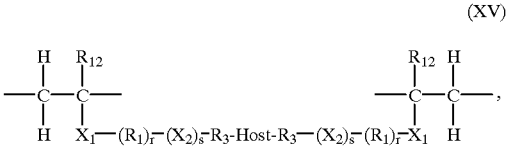

(XV)

wherein $R_1$, $R_3$, $R_{12}$, $X_1$, $X_2$, r, s and -Host- have the meanings given before, inclusive of preferred embodiments. These polymers may additionally contain non-fluorescent structural units from mono- and/or polyolefinically unsaturated monomers.

The weight ratio of chromophore structural units (XV) and optionally (V) to non-fluorescent structural units is dependent on the actual practical application, hence there are no well defined preferred ratios, other than the broad range 100:0 to 1:999. In certain applications where both color strength and fluorescence are required, then the preferred ratios of chromophore structural units to non-fluorescent structural units are 20:80 to 100:0, preferably 50:50 to 100:0 and more preferably 80:20 to 100:0. In circumstances where fluorescence is desired but color strength is not required, then the preferred ratio of chromophore structural units to non-luorescent structural units are 20:80 to 1:999, more preferably 10:90 to 1:999 and more preferably 5:95 to 1:999.

The above crosslinked polymers with one or both structural elements of formula (XV) may contain structural elements of formulae (V), (VI), (IX), (X), (XI), (XII), (XIII) and (XIV) alone or in any combination of at least 2 of these structural elements, or may contain structural elements of preferred residues formulae (VI), (X) and (IX), and further (X), (XI), (XII), (XIII) and (XIV) alone or in any combination of at least 2 of these structural elements.

Preferred divalent residues of the host chromophore correspond to the formula (XVI)

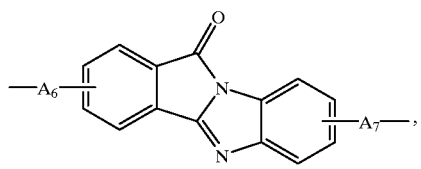

(XVI)

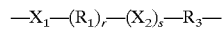

(XVII), wherein neighboring carbon atoms of the benzene rings can be condensed with benzene rings, heteroaromatic rings or both, and the functional groups can be linked to these rings, rather than to the benzene rings of the polycyclic core structure, and the aromatic rings are unsubstituted or substituted with halogens like F, Cl or Br; —CN, —NO$_2$, C$_1$ to C$_{18}$ alkyl, C$_3$ to C$_{12}$ cycloalkyl, C$_6$ to C$_{18}$ aryl, C$_5$ to C$_{17}$ heteroaryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$, aryloxy, C$_5$ to C$_{17}$ heteroaryloxy, C$_3$ to C$_{12}$ cycloalkylalkyloxy, C$_6$ to C$_{18}$ aralkyloxy, C$_5$ to C$_{17}$ heteroaralkyloxy, C$_1$ to C$_{18}$ alkylthio, C$_3$ to C$_{12}$ cycloalkylthio, C$_6$ to C$_{18}$ arylthio, C$_5$ to C$_{17}$ heteroarylthio, C$_3$ to C$_{12}$ cycloalkylalkylthio, C$_6$ to C$_{18}$ aralkylthio, C$_5$ to C$_{17}$ heteroaralkylthio, C$_1$ to C$_{18}$ alkyl-SO— or —SO$_2$, C$_3$ to C$_{12}$ cycloalkyl-SO— or -SO$_2$, C$_6$ to C$_{18}$ aryl-SO— or —SO$_2$, C$_5$ to C$_{17}$ heteroaryl-SO— or —SO$_2$, C$_3$ to C$_{12}$ cycloalkylalkyl—SO— or —SO$_2$, C$_6$ to C$_{18}$ aralkyl-SO— or —SO$_2$, C$_5$ to C$_{17}$ heteroaralkyl-SO— or —SO$_2$, secundary amino with 2 to 30 carbon atoms, and alkoxyalkyl with 2 to 20 carbon atoms, the cyclic aliphatic and aromatic residues (substituents) may also be substituted, for example with halogens like F, Cl or Br; or —CN, —NO$_2$, C$_1$ to C$_{18}$ alkyl, C$_3$ to C$_{12}$cycloalkyl, C$_6$ to C$_{18}$ aryl, C$_3$ to C$_{12}$cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, and A$_6$ and A$_7$ mean a direct bond or a divalent organic group.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 or 2 rings are condensed with the neighboring carbon atoms to form bicyclic or tricyclic systems. They may be selected from benzene, furane, thiophene, pyrrole, pyridine, and pyrimidine.

In a preferred embodiment, A$_6$ and A$_7$ correspond to the formula (XVII)

wherein

X$_1$, X$_2$, R$_1$, R$_3$, r and s have the meanings described before, inclusive of the preferred embodiments.

In a preferred embodiment the bivalent host residues correspond to formulae (XVIII) and (XVIIIa)

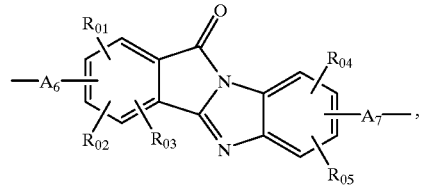

(XVIII)

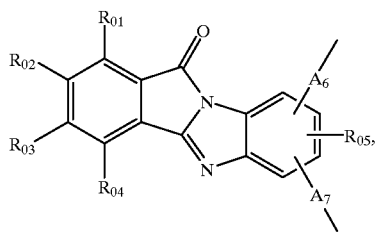

(XVIIIa)

wherein R$_{01}$, R$_{02}$, R$_{03}$, R$_{04}$, and R$_{05}$ independently from one another mean H, Cl, C$_1$ to C$_{18}$ alkyl, C$_1$ to C$_{18}$ alkoxy, phenyl, benzyl, C$_1$ to C$_{12}$ alkylphenyl or C$_1$ to C$_{12}$ alkylbenzyl. R$_{05}$ means preferably H, and A$_6$ and A$_7$ correspond to a bivalent residue of formula XVI.

In a preferred embodiment the groups A$_6$ and A$_7$ may be selected from the formulae

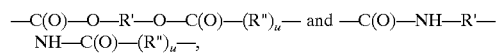

wherein R' is C$_2$ to C$_{20}$, preferably C$_2$ to C$_{12}$, and more preferably C$_2$ to C$_6$ alkylene, phenylene, benzylene, or oligoxyalkylene with preferably 2 to 6, and more preferably 2 to 4 oxyethylene and/or oxypropylene units, R'' means C$_1$ to C$_{12}$ alkylene, phenylene or benzylene, and u means 0 or 1.

Some preferred examples of host chromophore residues corresponding to formula (XVI) are

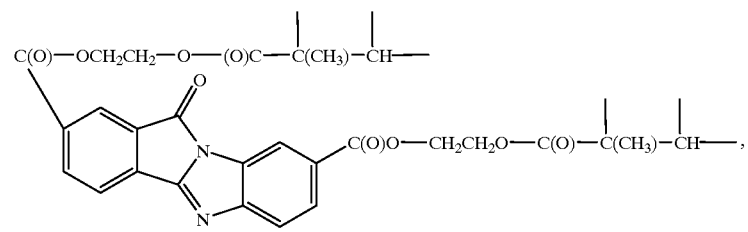

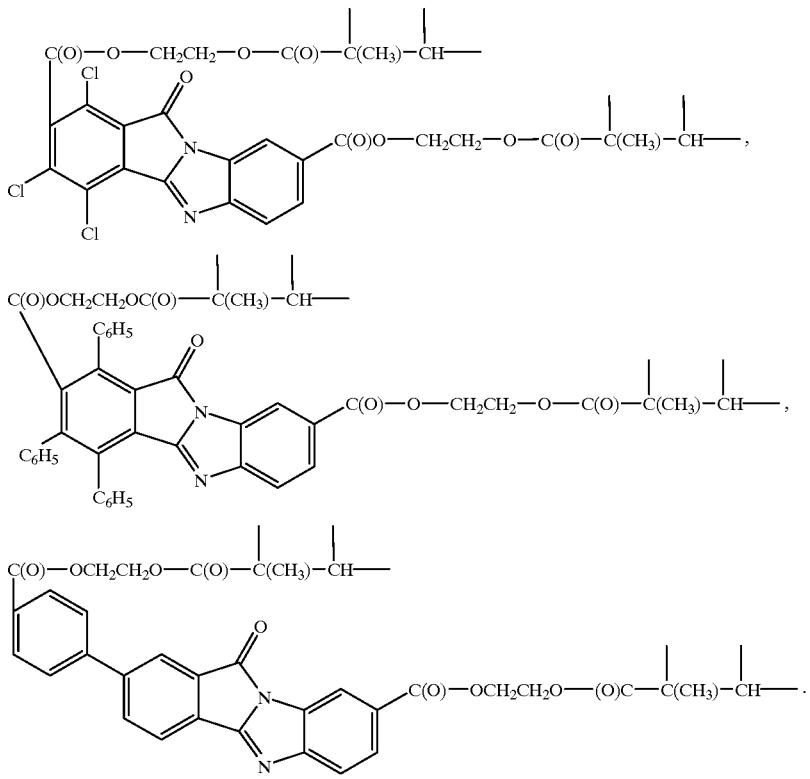

In another preferred embodiment of the invention the polymer according to the invention may contain or may be composed of functional host structures which contain two or three functional groups covalently linked, via a bridging group, to one ring of the host core structure. Thus the polymers with recurring structural units of the formulae (IV), (IVa) and (IVb) may additionally contain, or the units of the formula (IVa) may be replaced by recurring crosslinking units of the formula (IVc), (IVd) or both,

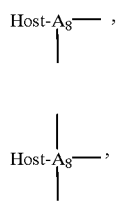

wherein $A_8$ means a trivalent or tetravalent organic residue, copolymerisable with the groups A to $A_4$, and Host is a monovalent fluorescent moiety, as defined before.

Preferred divalent and trivalent residues of the host chromophore may also correspond to the formulae (XIX) and (XIXa)

(XIX)

(XIXa)

wherein
neighboring carbon atoms of the benzene ring can be condensed with benzene rings, heteroaromatic rings or both, and
the aromatic rings are unsubstituted or substituted with halogens like F, Cl or Br; —CN, —NO$_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —SO$_2$, $C_3$ to $C_{12}$ cycloalkyl-SO— or —SO$_2$, $C_6$ to $C_{18}$ aryl-SO— or —SO$_2$, $C_5$ to $C_{17}$ heteroaryl-SO— or —SO$_2$, C$_3$ to C$_{12}$ cycloalkylalkyl-SO— or —SO$_2$, C$_6$ to C$_{18}$ aralkyl-SO— or —SO$_2$, C$_5$ to C$_{17}$ heteroaralkyl-SO— or —SO$_2$, secunday amino with 2 to 30 carbon atoms, and alkoxyalkyl with 2 to 20 carbon atoms, the cyclic aliphatic and aromatic residues (substituents) may also be substituted, for example with halogens like F, Cl or Br; or —CN, —NO$_2$, C$_1$ to C$_{18}$ alkyl, C$_3$ to C$_{12}$cycloalkyl, C$_6$ to C$_{18}$ aryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, and A$_8$ mean a trivalent or tetravalent organic group.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 ring is condensed with the neighboring carbon atoms to form bicyclic systems. They may be selected from benzene, furane, thiophene, pyrrole, pyridine, and pyrimidine.

In a preferred embodiment, A$_8$ corresponds to the formulae (XX) or (XXa), $$—R_{31}—(X_4)_{\overline{a}}—R_{32}—(X_5)_b, \quad (XX)$$

$$—R_{31}—X_6\begin{array}{c}R_{33}—X_7\\R_{33}—X_7,\end{array} \quad (XXa)$$

wherein (a) R$_{31}$ is a direct bond, C$_1$ to C$_{12}$ alkylene, phenylene or benzylene;
X$_4$ is N, O, S, C(O)O or C(O)N;
R$_{32}$ means C$_2$ to C$_{12}$ alkyltriyl, phenyltriyl or benztriyl, when a is 1 and b is 2, or means C$_2$ to C$_{12}$ alkyltetrayl, phenyltetrayl or benztetrayl, when a is 1 and b is 3;
X$_5$ means O, S, NH, C(O)O, C(O)NH, OC(O)—CH(—)—CH$_2$—, OC(O)—C(CH$_3$)(—)—CH$_2$—,
HNC(O)—CH(—)—CH$_2$—, HNC(O)—C(CH$_3$)(—)—CH$_2$—; or (b) R$_{32}$ is a bond, a is 0 and b is 2 or 3, X$_5$ has the above meanings and R$_{31}$ means C$_2$ to C$_{12}$ alkyltriyl, phenyltriyl or benztriyl, when b is 2, or means C$_2$ to C$_{12}$ alkyltetrayl, phenyltetrayl or benztetrayl, when b is 3;

(c) R$_{31}$ is a direct bond, C$_1$ to C$_{12}$ alkylene, phenylene or benzylene;
X$_6$ is N or C(O)N;
R$_{33}$ is C$_2$ to C$_{12}$ alkylene;
X$_7$ is O, S, C(O)O, C(O)NH, and OC(O)—CH(—)—CH$_2$—, OC(O)—C(CH$_3$)(—)—CH$_2$—,
HNC(O)—CH(—)—CH$_2$—, HNC(O)—C(CH$_3$)(—)—CH$_2$— or

—CH(—)—CH$_2$—.

R$_{31}$ and R$_{33}$ in the meaning of alkylene contain preferably 2 to 8 and mostly preferred 2 to 4 C-atoms. R$_{32}$ in the meaning of alktriyl contain preferably 2 to 8, more preferred 2 to 6, and mostly preferred 2 to 4 C-atoms.

In another preferred embodiment the bivalent or trivalent fluorescent moiety as host chromophore correspond to formulae (XXI) and (XXIa)

(XXI)

(XXIa)

wherein

R$_{01}$, R$_{02}$, R$_{03}$, R$_{04}$, and R$_{05}$ independently from one another mean H, Cl, C$_1$ to C$_{18}$ alkyl, C$_1$ to C$_{18}$ alkoxy, phenyl, benzyl, C$_1$ to C$_{12}$ alkylphenyl or C$_1$ to C$_{12}$ alkylbenzyl, and A$_8$ correspond to formulae XXVI or XXVIa. R$_{05}$ means preferably H.

In a preferred embodiment the group A$_8$ may be selected from the group

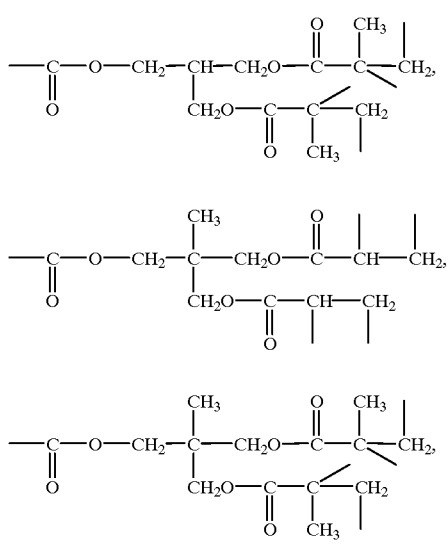
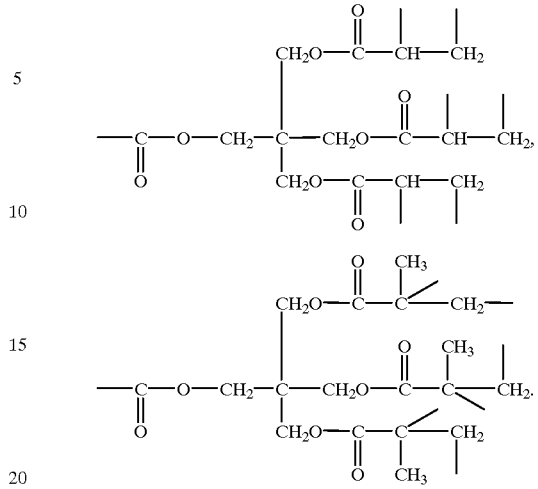
Some preferred examples are residues from the group (Ph means phenyl):
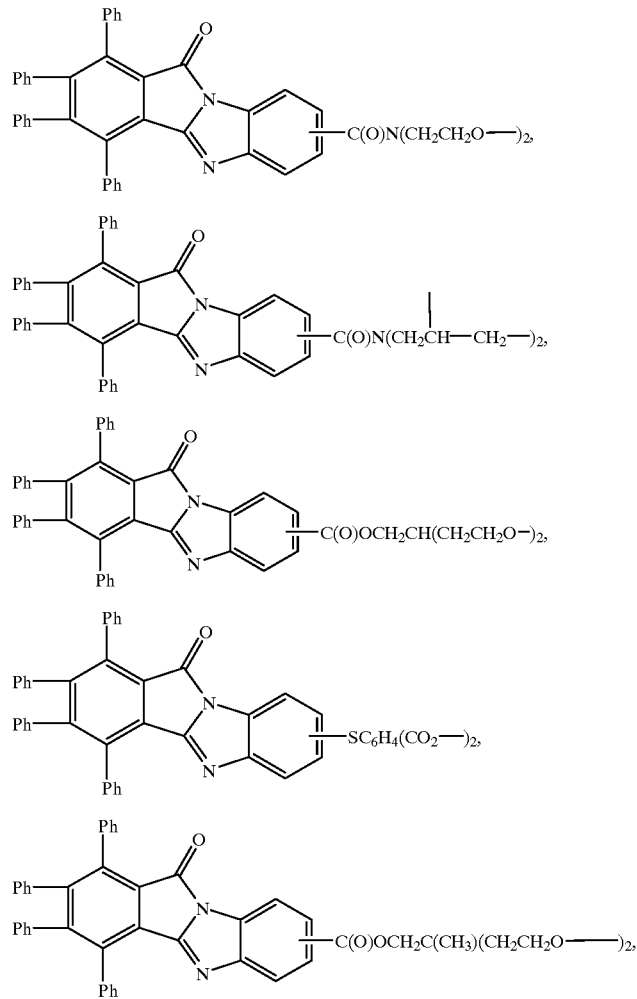

-continued
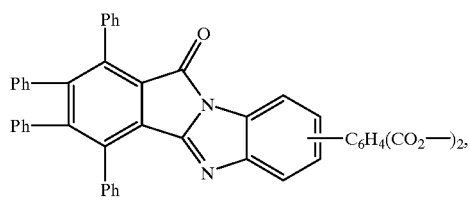
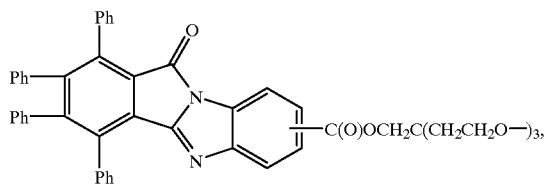
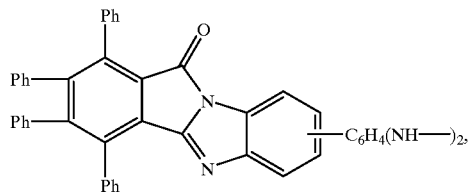
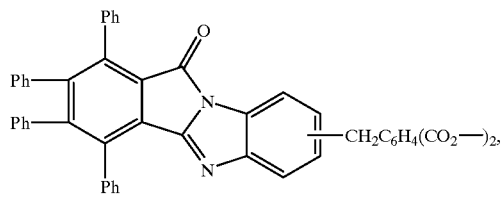
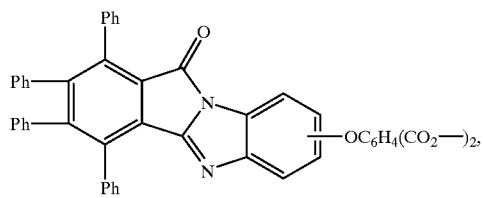
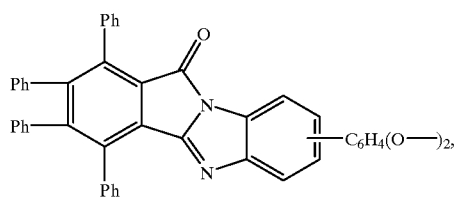
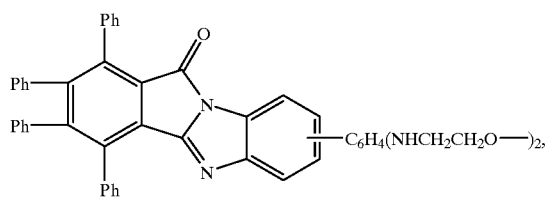
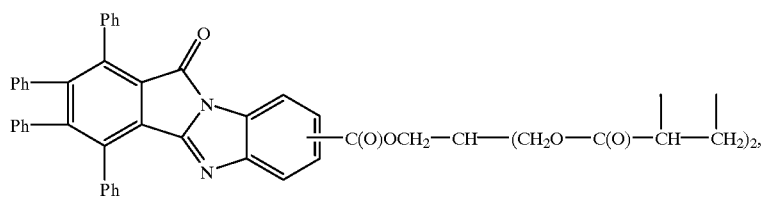

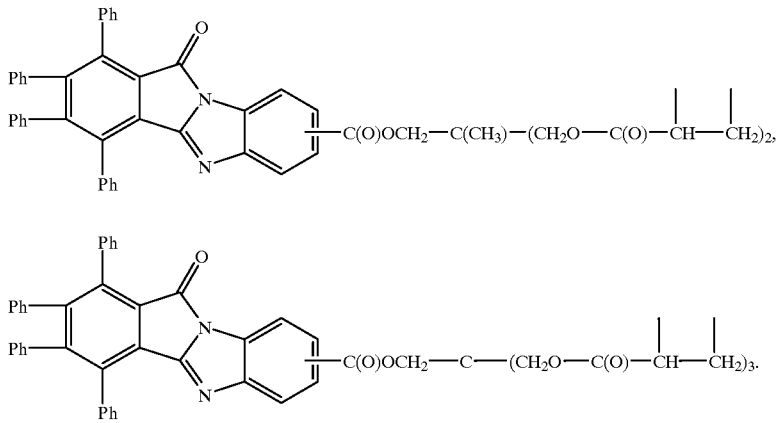

The polymers used in the instant invention may be random, block, graft or emulsion polymers (latices).

The preparation of polymers and their immobilization is well known in the art. One such method is to polymerize monomers with pendent host molecules, whilst another is to use polymers with pendent functional groups and to react them with host molecules that also possess functional groups.

The preparation of the polymers according to the invention may be carried out according to processes well known in the art of polymer chemistry such as step growth, anionic, cationic and radical polymerisations. Polymerization processes are solution, bulk, emulsion, photo- and interface polymerization.

Reaction temperatures may range from 0 to 250° C. The use of suitable and well established catalysts and photoinitiators are not described in detail herein. Azobisisobutyronitrile is well known as an effective radical catalyst for thermal polymerisations of olefinically unsaturated compounds. The polymerization may be carried out by mixing the monomers, catalysts and optionally a solvent together and heating, irradiating or by both heating and irradiating. The polymers may be isolated by precipitation into non-solvents or removing the solvents. If required further purification can be performed by means of repeat precipitations and drying.

The monomers are partially novel and partially known or they can be prepared by known or analogous methods.

The host monomers can be prepared according to the methods described in EP 0 456 609 Functional host chromophores are known or can be synthesized by known or analogous methods for their synthesis by employing optionally protected functional intermediates. wherein phthalic anhydride is reacted with 1,2-diaminobenzenes, whereby the anhydride, the diaminobenzenes or both contain optionally protected functional groups. More details are disclosed in the examples.

The functional groups may be selected from the group consisting of alkyl bonded halogen like Cl and Br; —N$_3$, epoxide, —OH, —SH, —CN, —NHR$_{100}$, =C=NR$_{100}$, =CO, —CH—O, —NCO, —CH=CH$_2$, —C(CH$_3$)=CH$_2$, —C(O)OH, —SO$_3$H, —SO$_2$Cl, —SO$_2$Br, —C(O)—Cl, —C(O)—Br, —OC(O)—OR$_{101}$, —OC(O)—NR$_{102}$R$_{103}$, —C(O)—OR$_{104}$, —SO$_2$—OR$_{104}$—C(O)—NR$_{102}$R$_{103}$, and —SO$_2$—NR$_{102}$R$_{103}$, wherein $R_{100}$ means H, $C_1$–$C_{18}$ alkyl, phenyl, or benzyl, $R_{101}$ means $C_1$–$C_{18}$ alkyl, phenyl, or benzyl, $R_{102}$ and $R_{103}$ independently from one another means H, $C_1$–$C_{18}$ alkyl, phenyl, or benzyl, and $R_{104}$ means $C_1$–$C_{18}$ alkyl, phenyl, or benzyl.

$R_{100}$, $R_{101}$, $R_{102}$, $R_{103}$ and $R_{104}$ contain as alkyl preferably 1 to 12, more preferably 1 to 8 and most preferably 1 to 4 carbon atoms.

More preferred functional groups are selected from the group consisting of alkyl linked Cl and Br; epoxide, —OH, —SH, —NHR$_{100}$, —CH=CH$_2$, —C(CH$_3$)=CH$_2$, —NCO, —C(O)OH, —C(O)—Cl, —C(O)—Br, —C(O)—OR$_{104}$, —C(O)—NR$_{102}$R$_{103}$, wherein $R_{100}$ means H or $C_1$–$C_{12}$ alkyl, $R_{102}$ and $R_{103}$ independently from one another means H or $C_1$–$C_4$ alkyl, and $R_{104}$ means $C_1$–$C_8$ alkyl.

Especially preferred difunctional host compounds used for the preperation of composition (a1) crosslinked polymers correspond to the formula (XXII)

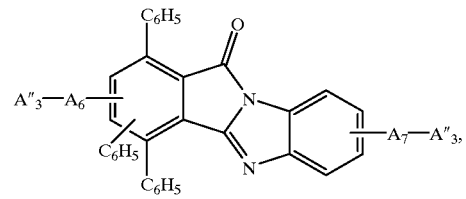
(XXII)

wherein $A_6$ is $C_6H_4$ and $A_7$ is a direct bond or $C_1$ to $C_6$ alkylene, phenylene or benzylene, and $A''_3$ means —COOH, —C(O)—Cl, —C(O)—Br, —C(O)—OR$_{104}$, —C(O)—NR$_{102}$R$_{103}$, —C(O)O—C$_2$ to C$_{12}$ alkylene-OH, —C(O)O—C$_2$ to C$_{12}$ alkylene-O—C(O)—CH=CH$_2$, or —C(O)O—C$_2$ to C$_{12}$ alkylene-O—C(O)—C(CH$_3$)=CH$_2$.

As examples for difunctional host compounds the following compounds may be mentioned:

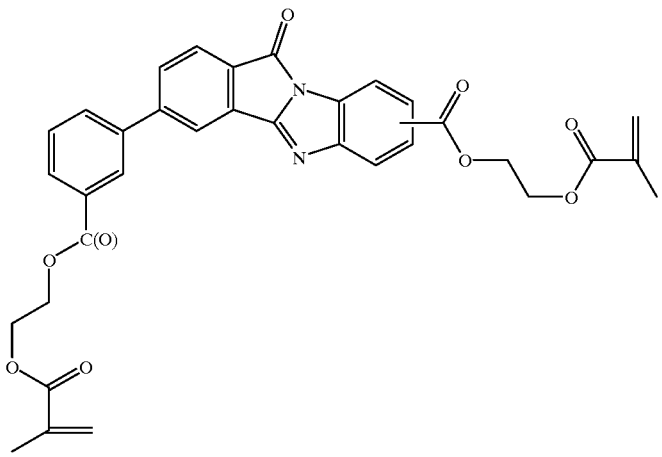

which may be synthesized starting from the corresponded acid chloride, for example by carrying out the reaction in a solvent like dry pyridine and thereby adding a, preferably large, excess of hydroxy ethyl methacrylate, preferably dissolved in the same solvent. Workup may be done by pouring the completed reaction mixture slowly on ice which may contain an acid like HCl, yielding a precipitate, which may be filtered and dried, for example by vacuum pumping. This crude precipitate preferably may be further purified, to remove residual hydroxyethyl methacrylate, by re-precipitation for example from chloroform into a large excess of hexane.

The corresponding acid chloride may be synthesized preferably reaction of the corresponding diacid compound with thionyl chloride, preferably in a solvent like dry benzene. The reaction mixture may be heated to complete the reaction, for example to reflux temperature. Solvent and excess thionyl chloride can be removed preferably using a stream of nitrogen.

The corresponding diacid compound may be synthesized for example starting from biphenyl-3,4,3' tricarboxylic acid, which is obtainable in accordance with the method described in Zh. Org. Khim 2(7), 1288 (1966), by reaction with 3,4-diamino benzoic, preferably in a solvent like acetic anhydride. The obtained benzo[4,5]-imidazo[2,1-a]isoindol-11-one-carboxylic diacid may be filtered and washed as usual with for example water and methanol, and may be further purified by column chromatography using preferably chloroform as the eluting solvent.

(II)

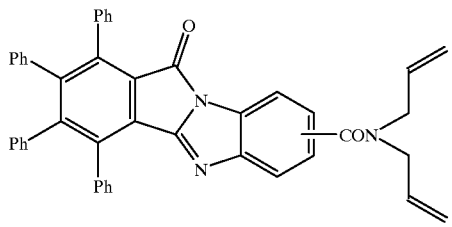

which may be synthesized starting from the corresponding trapheny-benzo[4,5] imidazo[2,1-a]isoindol-11-one-carboxylic acid chloride (obtainable in a similar manner as the abovementioned diacid chloride) by reaction with diallylamine, preferably dissolved in a solvent like dry pyridine. Workup may be carried out by pouring the reaction mixture in ice cold water, washing the obtained crude reaction product with water and dried it. Further purification may be done via column chromatography using for example chloroform as the eluting solvent.

As an example for a trifunctional host compound the following compound may be manufactured:

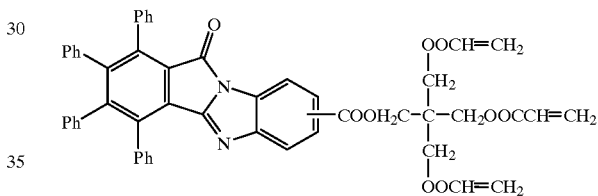

The preparation of this compound may be carried out starting from the corresponding trifunctional OH-derivative of tetraphenyl-benzo[4,5]imidazo[2,1-a]isoindol-11-one with acryloylchloride, preferably in a solvent like dichloromethane. Workup may be carried out in pouring the reaction mixture in a large excess of water, followed by filtering the obtained precipitate. If desired the crude product may be washed further for example with water and methanol and then dried, for example in an atmosphere under reduced pressure. The corresponding trifunctional OH-derivative may be synthesized preferably by the reaction of pentaerythritol (large excess) with tetraphenyl-benzo[4,5] imidazo[2,1-a]isoindol-11-one-carboxylic acid chloride (obtainable by reaction of the corresponding carboxylic acid with thionyl chloride), preferably in a solvent like dry pyridine. Workup may be carried out as usual and described before.

Monofunctional benzo[4,5]imidazo[2,1-a]isoindol-11-ones are known or novel. The functional group may be selected from the group consisting of halogens like Cl and Br; —$N_3$, epoxide, —OH, —SH, —CN, —$NHR_{100}$, =C=$NR_{100}$, =CO, —CH=O, —NCO, —CH=$CH_2$, —C($CH_3$)=$CH_2$, —C(O)OH, —$SO_3H$, —$SO_2Cl$, —$SO_2Br$, —C(O)—Cl, —C(O)—Br, —OC(O)—$OR_{101}$, —OC(O)—$NR_{102}R_{103}$, —C(O)—$OR_{104}$, —$SO_2$—$OR_{104}$, —C(O)—$NR_{102}R_{103}$, and —$SO_2$—$NR_{102}R_{103}$, wherein $R_{100}$ means H, $C_1$–$C_{18}$ alkyl, phenyl, or benzyl, $R_{101}$ means $C_1$–$C_{18}$ alkyl, phenyl, or benzyl, $R_{102}$ and $R_{103}$ independently from one another means H, $C_1$–$C_{18}$ alkyl, phenyl, or benzyl, and $R_{104}$ means $C_1$–$C_{18}$ alkyl, phenyl, or benzyl.

$R_{100}$, $R_{101}$, $R_{102}$, $R_{103}$ and $R_{104}$ contain as alkyl preferably 1 to 12, more preferably 1 to 8 and most preferably 1 to 4 carbon atoms.

More preferred functional groups are selected from the group consisting of alkyl linked Cl and Br; epoxide, —OH, —SH, —NHR$_{100}$, —CH=CH$_2$, —C(CH$_3$)=CH$_2$, —NCO, —C(O)OH, —C(O)—Cl, —C(O)—Br, —C(O)—OR$_{104}$, —C(O)—NR$_{102}$R$_{103}$, wherein $R_{100}$ means H or $C_1$–$C_{12}$ alkyl, $R_{102}$ and $R_{103}$ independently from one another means H or $C_1$–$C_4$ alkyl, and $R_{104}$ means $C_1$–$C_8$ alkyl.

Especially preferred compounds correspond to the formula (XXIII) are

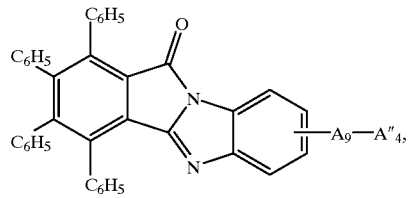

(XXIII)

wherein $A_9$ is a direct bond or $C_1$ to $C_6$ alkylene, phenylene or benzylene, and $A''_4$ means —COOH, —C(O)—Cl, —C(O)—Br, —C(O)—OR$_{104}$, —C(O)— NR$_{102}$R$_{103}$, —C(O)O—$C_2$ to $C_{12}$ alkylene-OH, —C(O)O—$C_2$ to $C_{12}$ alkylene-O—C(O)—CH=CH$_2$, or —C(O)O—$C_2$ to $C_{12}$ alkylene-O—C(O)—C(CH$_3$)=CH$_2$.

Examples of monofunctional host compounds used for the preperation of composition (a1) polymers are (Ph means phenyl):

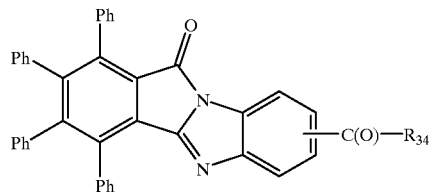

wherein $R_{34}$ is Cl, OH, OR$_{104}$ and $R_{104}$ means $C_1$–$C_8$ alkyl, NR$_{102}$R$_{103}$ and $R_{102}$ and $R_{103}$ independently from one another mean H, $C_1$–$C_4$ alkyl or $C_2$ to $C_4$ hydroxyalkyl, —C(O)O—$C_2$ to $C_{12}$ alkylene-O—C(O)—CH=CH$_2$, —C(O)O—$C_2$ to $C_{12}$ alkylene-O—C(O)—C(CH$_3$)=CH$_2$, —C(O)ONH—$C_2$ to $C_{12}$ alkylenene-O—C(O)—CH=CH$_2$, or —C(O)NH—$C_2$ to $C_{12}$ alkylene-O—C(O)—C(CH$_3$)=CH$_2$;

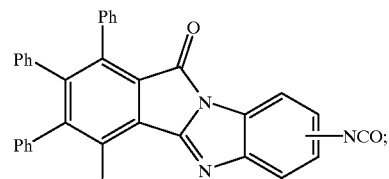

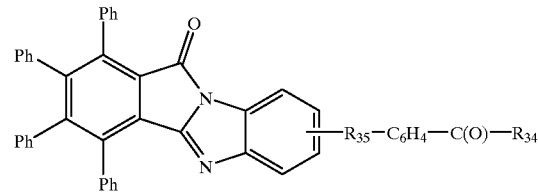

wherein $R_{35}$ is a direct bond, methylene, ethylidene, 2,2-propylidene, O, S, NH, N($C_1$ to $C_4$ alkyl), C(O) or C(O)NH, and $R_{34}$ has the meaning given before;

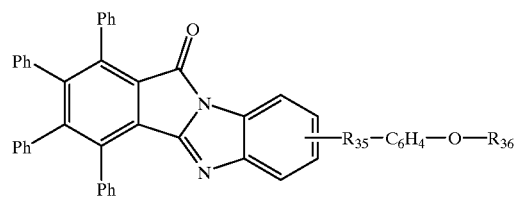

wherein $R_{35}$ has the meaning given before and $R_{36}$ means H, $C_2$ to $C_4$ hydroxyalkyl, glycidyl or OR$_{36}$ means NH-glycidyl or NHC$_2$ to $C_4$ hydroxyalkyl; and

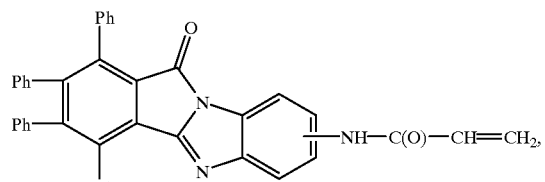

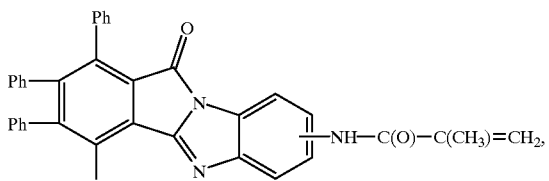

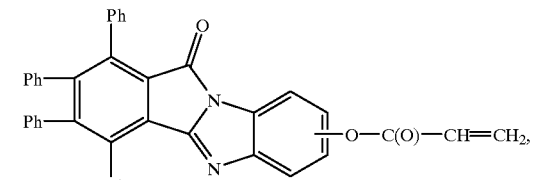

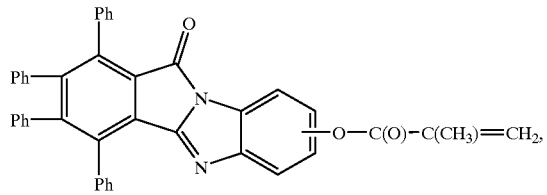

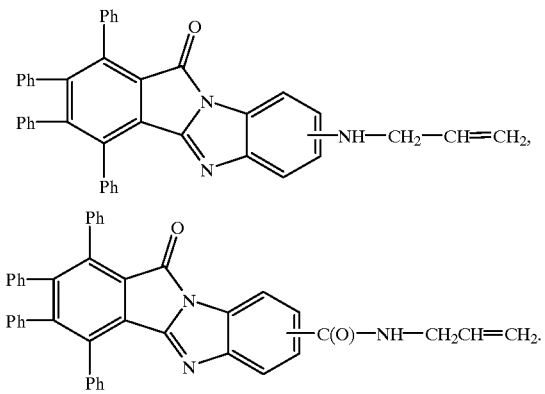

The process to prepare the materials and compounds used for the polymers containing host moieties according to the composition (a1) can be carried out in an inert solvent. Inert means, that the choice of a solvent is determined by the reactivity of the used ingredients, hence a solvent is selected such that no undesired side reactions occur.

Suitable inert solvents are for example protic-polar and aprotic solvents, which may be used alone or in an admixture of at least two solvents. Examples are: water, alcohols (methanol, ethanol, propanol, butanol), ethyleneglycolmonomethyl- or -monoethylether, ether (dibutylether, tetrahydrofuran, dioxane, ethyleneglycol dimethylether, ethyleneglycoldiethylether, diethyleneglycoldiethylether, triethyleneglycoldimethylether), halogenated hydrocarbons (methylenchloride, chloroform, 1,2-dichloroethane, 1,1,1-trichlororethane, 1,1,2,2-tetrachloroethane), carboxylic esters and lactones (acetic acid ethylester, propionic acid methylester, benzoic acid ethylester, 2-methoxyethylacetate, g-butyrolactone, d-valerolactone, pivalolactone), carboxylic acid amides and lactames; N,N-dimethylformamide, N,N-diethylformamide, N,N-dimethylacetamide, tetramethylurea, hexamethylphosphorous acidtriamide, g-butyrolactame, î-caprolactame, N-methylpyrrolidone, N-acetylpyrrolidone, N-methylcaprolactame; sulfoxides (dimethylsulfoxide), sulfones (dimethylsulfone, diethylsulfone, trimethylenesulfone, tetramethylenesulfone), tertiary amines (N-methylpiperidine, N-methylmorpholine), aliphatic and aromatic hydrocarbons like petroleumether, pentane, hexane, cyclohexane, methylcyclohexane, benzene or substituted benzenes (chlorobenzol, o-dichlorobenzene, 1,2,4-tri-chlorobenzene, nitrobenzene, toluene, xylene) and nitriles (acetonitrile, propionitrile, benzenenitrile, phenylacetonitrile), ketones (acetone, methyl-isobutyleketone).

Suitable guest chromophores are those fluorescent molecules whose absorption wavelengths overlap with the emission wavelengths of the respective host. The guest molecules are preferably selected from those that posses absorption wavelengths in the range from 380 to 800 nm and fluoresce at wavelengths in the range 400 to 780 nm. It is also preferred that the guest molecules possess fluorescence quantum yields of 0.1 to 1.0, preferably 0.3 to 1.0, more preferably 0.5 to 1.0 and most preferred 0.7 to 1.0.

Fluorescent molecules as guest chromophores are selected preferably from the group consisting of quinacridones, perylenes, diketopyrrolopyrroles, fluoresceines, rhodamines, coumarines, xanthenes, pyrenes, oxazines, oxazoles, cyanines, phthalocyanines, porphyrines and styryl dyes.

The guest molecules may be unsubstituted or substituted with F, Cl, Br, I, —CN, —NO$_2$, C$_1$ to C$_{18}$ alkyl, C$_3$ to C$_{12}$ cycloalkyl, C$_6$ to C$_{18}$ aryl, C$_5$ to C$_{17}$ heteroaryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, C$_5$ to C$_{17}$ heteroaryloxy, C$_3$ to C$_{12}$ cycloalkylalkyloxy, C$_6$ to C$_{18}$ aralkyloxy, C$_5$ to C$_{17}$ heteroaralkyloxy, C$_1$ to C$_{18}$ alkylthio, C$_3$ to C$_{12}$ cycloalkylthio, C$_6$ to C$_{18}$ arylthio, C$_5$ to C$_{17}$ heteroarylthio, C$_3$ to C$_{12}$ cycloalkylalkylthio, C$_6$ to C$_{18}$ aralkylthio, C$_5$ to C$_{17}$ heteroaralkylthio, C$_1$ to C$_{18}$ alkyl-SO— or —SO$_2$, C$_3$ to C$_{12}$ cycloalkyl-SO— or —SO$_2$, C$_6$ to C$_{18}$ aryl-SO— or —SO$_2$, C$_5$ to C$_{17}$ heteroaryl-SO— or —SO$_2$, C$_3$ to C$_{12}$ cycloalkylalkyl-SO— or —SO$_2$, C$_6$ to C$_{18}$ aralkyl-SO— or —SO$_2$, C$_5$ to C$_{17}$ heteroaralkyl-SO— or —SO$_2$, secundary amino with 2 to 30 carbon atoms, and alkoxyalkyl with 2 to 20 carbon atoms.

The cyclic aliphatic and aromatic residues (substituents) may be also substituted, for example with F, Cl, Br, I, —CN, —NO$_2$, C$_1$ $_{to}$ $_{C18}$ alkyl, C$_3$ to C$_{12}$ cycloalkyl, C$_6$ to C$_{18}$ aryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy. The substituent alkyl may be linear or branched and may be substituted with a halogen like F or Cl.

Examples of substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

The number of substituents is arbitrary and depends essentially upon synthetic possibilities and the desired optical properties pertaining to fluorescence and absorption.

Preferably, the guest molecules are represented by the following formulae:

-continued

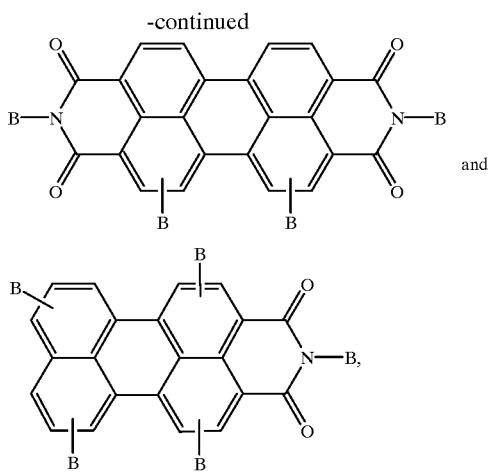

and salts of the rhodamine residue, inclusive salts with the group =N$^+$ R$_{011}$R$_{012}$,
wherein $R_{06}$, $R_{07}$ and $R_{08}$ are independently H or a substituent, or one of $R_{07}$ is H and the other $R_{07}$, $R_{06}$ and $R_{08}$ are independently H or a substituent, or $R_{08}$ is H and the other $R_{07}$ and $R_{06}$ are independently H or a substituent, B is H or a substituent, $R_{011}$, means $C_1$ to $C_{20}$ alkyl, or phenyl or benzyl which are unsubstituted or substituted with $C_1$ to $C_{18}$ alkyl, $R_{09}$ and $R_{010}$ independently of one another mean H, $C_1$ to $C_{20}$ alkyl, or phenyl or benzyl which are unsubstituted or substituted with $C_1$ to $C_{18}$ alkyl, $R_{012}$ is H or $C_1$ to $C_{18}$ alkyl, whereby the rings are unsubstituted or substituted with F, Cl, Br, I, —CN, —NO$_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —SO$_2$, $C_3$ to $C_{12}$ cycloalkyl-SO— or —SO$_2$, $C_6$ to $C_{18}$ aryl-SO— or —SO$_2$, $C_5$ to $C_{17}$ heteroaryl-SO— or —SO$_2$, $C_3$ to $C_{12}$ cycloalkylalkyl-SO— or —SO$_2$, $C_6$ to $C_{18}$ aralkyl-SO— or —SO$_2$, $C_5$ to $C_{17}$ heteroaralkyl-SO— or —SO$_2$, secunary amino with 2 to 30 carbon atoms, and alkoxyalkyl with 2 to 20 carbon atoms.

The cyclic aliphatic and aromatic residues may be also substituted, for example with F, Cl, Br, I, —CN, —NO$_2$, $C_1$ to $C_{18}$ alkyl, $C_3$ to $C_{12}$ cycloalkyl, $C_6$ to $C_{18}$ aryl, $C_3$ to $C_{12}$ cycloalklalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy. The alkyl may be substituted with halogens like F, Cl or Br.

More preferred substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

$R_{011}$ means preferably $C_1$ to $C_{18}$ alkyl, which may linear or branched, or phenyl or benzyl which are unsubstituted or substituted with $C_1$ to $C_{12}$ alkyl, and $R_{09}$ and $R_{010}$ independently of one another mean preferably H, $C_1$ to $C_{18}$ alkyl, or phenyl or benzyl which are unsubstituted or substituted with $C_1$ to $C_{12}$ alkyl. Examples are methyl, ethyl, and the isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, phenyl, benzyl, methylphenyl, ethylphenyl, propylphenyl, butylphenyl, pentylphenyl, hexylphenyl, heptylphenyl, octylphenyl, methylbenzyl, ethylbenzyl, propylbenzyl, butylbenzyl, pentylbenzyl, hexylbenzyl, heptylbenzyl, and octylbenzyl.

$R_{012}$ means preferably $C_1$ to $C_{12}$ alkyl, more preferably $C_1$ to $C_8$ alkyl and most preferably $C_1$ to $C_4$ alkyl.

Suitable salts may be derived from inorganic or organic acids, for example HCl, HBr, H$_2$SO$_4$, carboxylic acids like acetic acid, chloro- or fluoroacetic acids, propionic acid, benzoic acid, chloro- or fluorobenzoic acids, sulfonic acids like methylsulfonic acid, chloro- or fluoromethylsulfonic acids, phenylsulfonic acid, toluylsulfonic acid, and chloro- or fluorobenzenesulfonic acids.

More preferred guest molecules are those represented by the following formulae:

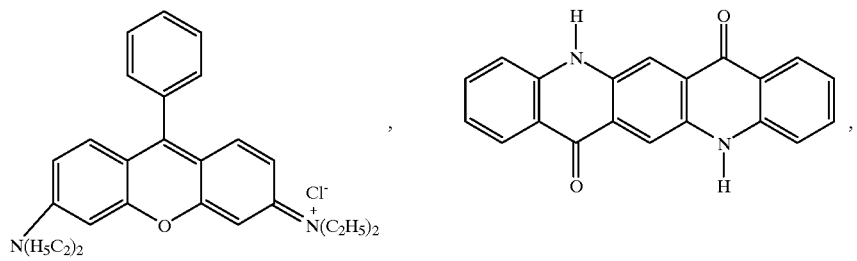

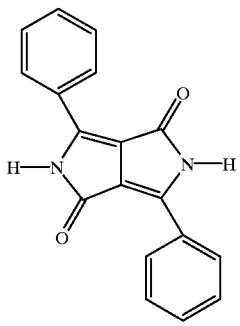
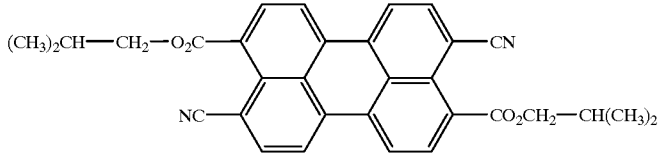

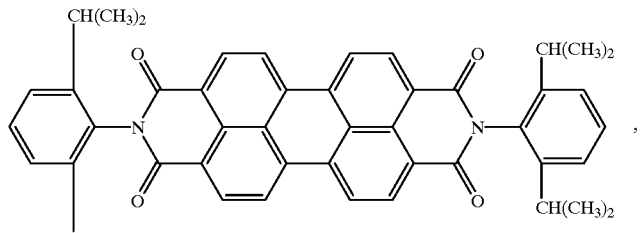

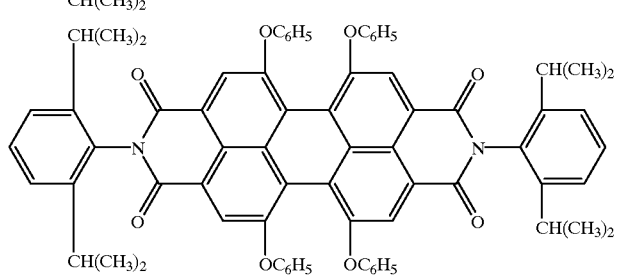

Pigment precursors having removable alkoxycarbonyl groups such as those described for example in in EP-A-0 654 711 are also preferred guest molecules. They have high solubilities in polar solvents as mentioned previously herein, enabling easy preparation of compositions (a1) and even easy regeneration of molecularly dissolved pigments as the guest molecules by simple heat treatment after the preparation of the compositions (a1).

The guest molecules used for composition (a1) can be selected from, but not restricted to, the below listing:
Diphenyl N,N'-dibutyl diketo pyrrolo[3,4-c]pyrrole,
Di-(m-methyl)phenyl N,N'-dibutyl diketo pyrrolo[3,4-c] pyrrole,
Diphenyl N,N'-dibenzyl diketo pyrrolo[3,4-c]pyrrole,
Di-(p-pheny)phenyl N,N'-dibutyl diketo pyrrolo[3,4-c] pyrrole,
Di-(p-methyl)phenyl N,N'-dibutyl diketo pyrrolo[3,4-c] pyrrole,
Diphenyl N,N'-diethyi diketo pyrrolo[3,4-c]pyrrole,
Di-(p-tertiaer-butyl)phenyl N,N'-dimethyl diketo pyrrolo[3,4-c]pyrrole,
N,N'-Di(1-heptyloctyl)perylene-3,4:9,10-bis(dicarboximide),
N,N'-Di(1-octyinonyl)perylene-3,4:9,10-bis(dicarboximide),
N,N'-Di(1-nonyidecyl)perylene-3,4:9,10-bis(dicarboximide),
N,N'-Di(1-decylundecyl)perylene-3,4:9,10-bis(dicarboximide),
N,N'-Di(1-dodecyltridecyl)perylene-3,4:9,10-bis(dicarboximide),
N,N'-Di(1-hexadecylheptadecyl)perylene-3,4:9,10-bis(dicarboximide),
N,N'-Di(1-heptyloctyl)perylene-3,4:9,10-bis(dicarboximide),
N,N'-Di(1-octadecylnonadecyl)perylene-3,4:9,10-bis(dicarboximide),
N,N'-Di(1-2,5, di-teff-butylphenyl)perylene-3,4:9,10-bis(dicarboximide),
N,N' dimethyl quinacridone,
N,N' diethyl quinacridone,
N,N' dibenzyl quinacridone,
N,N' di(o-chlorobenzyl) quinacridone
N,N' di(isopropyl) quinacridone,
N,N' di(nbutyl) quinacridone,
Fluorescein,
2',7'-dichloro fluorescein,
Lumogen Series Compounds (BASF)
Rhodamine 6G,
Rhodamine 6G perchlorate,
Rhodamine 6G tetrafluoroborate,
Rhodamine 19 perchlorate,
Rhodamine 110,
Rhodamine B,
Rhodamine 116,
Rhodamine 123.

The solid composition (a1) according to the instant invention comprises a host chromophore and an effective amount of a guest chromophore. The weight ratio between the host chromophores and the guest chromophores is preferably 50:50 to 9999:1, more preferably 60:40 to 999:1 and most preferably 70:30 to 999:1.

Another aspect of this invention is the preparation of semi-interpenetrating networks that employ linear (thermoplastic) polymers of composition (a1). By admixing a host containing polymer and guest molecules with multi-functional comonomers or multi-functional prepolymers, such that neither the host polymer or guest molecules participate in the polymerisation reaction, but are entangled and dispersed respectively therein, a highly fluorescent semi-interpenetrating network is obtained. Alternatively, the guest molecules can be dispersed in the crosslinked network by swelling the crosslinked system in a solvent containing guest molecules, and allowing them to diffuse into the network. Preferred crosslinking systems include, but are not restricted to, alcohol-isocyanates, amine-isocyanates, multivinyl monomers, multi-vinyl containing prepolymers, multi-allyl containing prepolymers, amine-epoxy and acid-epoxy.

Another aspect of this invention is the preparation of an interpenetrating network employing the polymers of composition (a1). Such a system preferably employs host polymers that contain pendant- or end functional groups that can participate in the crosslinking reaction with multi-vinyl or multi-functional comonomers or prepolymers, and affords a highly fluorescent crosslinked network. The guest molecules are dispersed in the crosslinking reaction medium. Alternatively, if the crosslinked polymer is swollen in a solvent containing guest molecules, the guest molecules can diffuse into the network. Preferred crosslinking systems include, but are not restricted to, alcohol-isocyanates, amine-isocyanates, multivinyl monomers, multi-vinyl containing prepolymers, multi-allyl containing prepolymers, amine-epoxy and acid-epoxy.

The fluorescent molecules to be used as host chromophores in the instant invention of composition (a2) are benzo[4,5]imidazo[2,1-a]isoindol-11-ones, preferably represented by the general formula (I),

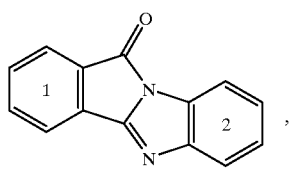

(I)

wherein
the neighboring carbon atoms of the benzene rings 1 and 2 are condensed with benzene rings, heteroaromatic rings, aliphatic rings, or heteroaliphatic rings, and wherein the benzene rings 1 or 2 or both, the condensed ring moieties or all are unsubstituted or substituted with an organic group.

The groups forming a condensed ring are preferably selected from the group consisting of bivalent residues of formulae —CH=CH—CH=CH—, —CH=CH—N=CH—, —CH=CH—CH=N—, —CH=N—CH=N—, —CH=CH—NR$_{37}$—, —CH=N—CH$_2$—, —CH=CH—S—, —CH=CH—O—, —(CH$_2$)$_3$—, —(CH$_2$)$_4$—, —CH$_2$—CH$_2$—NR$_1$—CH$_2$—, —CH$_2$—CH$_2$—CH$_2$—NR$_{37}$—, —CH$_2$—CH$_2$—O—CH$_2$—, —CH$_2$—CH$_2$—CH$_2$—O—, —CH$_2$—CH$_2$—S—CH$_2$—, —CH$_2$—CH$_2$—CH$_2$—, —CH$_2$—O—CH$_2$—, —CH$_2$— CH$_2$—O—, —CH$_2$—O—CH$_2$—S—CH$_2$—, and —CH$_2$—CH$_2$—S—, wherein R$_{37}$ is H or an organic substituent, and the bivalent residues are unsubstituted or substituted with an organic group.

R$_{37}$ as organic substituent may be linear or branched C$_1$ to C$_{20}$ alkyl, C$_5$ to C$_7$ cycloalkyl, benzyl or R$_{38}$—C(O)—, wherein R$_{38}$ is C$_1$ to C$_{20}$ alkyl, which is unsubstituted or substituted with F, Cl or C$_1$ to C$_{12}$ alkoxy, or C$_5$ to C$_7$ cycloalkyl, phenyl or benzyl, which are is unsubstituted or substituted with F, Cl, C$_1$ to C$_{12}$ alkyl, or C$_1$ to C$_{12}$ alkoxy.

Preferred examples for R$_1$ are H, methyl, ethyl, propyl, butyl, pentyl, hexyl, benzyl, methylbenzyl, dimethylbenzyl, acetyl, propionyl, butyroyl, benzyl-C(O)—, phenyl-C(O)—, toluyl-C(O)—, mono-, di- or tri-chloroacetyl, and mono-, di- or tri-fluoroacetyl, mono- and dichlorophenyl-C(O)—.

The organic group substituent may be selected from the group consisting of halogen, —CN, —NO$_2$, C$_1$ to C$_{18}$ alkyl, C$_2$ to C$_{18}$ alkenyl, C$_2$ to C$_{18}$ alkinyl, C$_1$ to C$_{18}$ hydroxyalkyl, C$_1$ to C$_{18}$ halogenalkyl, C$_3$ to C$_{12}$ cycloalkyl, C$_6$ to C$_{18}$ aryl, C$_5$ to C$_{17}$ heteroaryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, C$_5$ to C$_{17}$ heteroaryloxy, C$_3$ to C$_{12}$ cycloalkylalkyloxy, C$_6$ to C$_{18}$ aralkyloxy, C$_5$ to C$_{17}$ heteroaralkyloxy, C$_1$ to C$_{18}$ alkylthio, C$_3$ to C$_{12}$ cycloalkylthio, C$_6$ to C$_{18}$ arylthio, C$_5$ to C$_{17}$ heteroarylthio, C$_3$ to C$_{12}$ cycloalkylalkylthio, C$_6$ to C$_{18}$ aralkylthio, C$_5$ to C$_{17}$ heteroaralkylthio, C$_1$ to C$_{18}$ alkyl-SO— or —SO$_2$, C$_3$ to C$_{12}$ cycloalkyl-SO— or —SO$_2$, C$_6$ to C$_{18}$ aryl-SO— or —SO$_2$, C$_5$ to C$_{17}$ heteroaryl-SO— or —SO$_2$, C$_3$ to C$_{12}$ cycloalkylalkyl-SO— or —SO$_2$, C$_6$ to C$_{18}$ aralkyl-SO— or —SO$_2$, C$_1$ to C$_{18}$ alkyl-CO—, C$_3$ to C$_{12}$ cycloalkyl-CO—, C$_6$ to C$_{18}$ aryl-CO—, C$_5$ to C$_{17}$ heteroaryl-CO—, C$_3$ to C$_{12}$ cycloalkylalkyl-CO—, C$_6$ to C$_{18}$ aralkyl-CO—, C$_5$ to C$_{17}$ heteroaralkyl-CO—, —NR$_{39}$R$_{40}$, alkoxyalkyl with 2 to 20 carbon atoms, polyoxyalkylene-OR$_{42}$, —X—(R$_{41}$)$_k$—C(O)—NR$_{39}$R$_{40}$, —X—(R$_{41}$)$_k$—C(O)—OR$_{42}$, —X—(R$_{41}$)$_k$—SO$_2$—OR$_{42}$, —X—(R$_{41}$)$_k$—SO$_2$—NR$_{39}$R$_{40}$, —NH—C(O)—R$_{42}$ and —O—C(O)—R$_{42}$, wherein R$_{39}$ and R$_{40}$ mean independently from one another H, C$_1$ to C$_{20}$ alkyl, cyclopentyl, cyclohexyl, phenyl, benzyl, C$_1$ to C$_{12}$ alkylphenyl or C$_1$ to C$_{12}$ alkylbenzyl, or R$_{39}$ and R$_{40}$ together mean tetramethylene, pentamethylene, or the groups —CH$_2$—CH$_2$—O—CH$_2$CH$_2$— or —CH$_2$—CH$_2$—NR$_3$—CH$_2$—CH$_2$—, R$_3$ is H or C$_1$ to C$_6$ alkyl, R$_{41}$ is C$_1$ to C$_{12}$ alkylene, phenylene or benzylene, R$_{42}$ means H, C$_1$ to C$_{20}$ alkyl, cyclopentyl, cyclohexyl, phenyl, benzyl, C$_1$ to C$_{12}$ alkylphenyl or C$_1$ to C$_{12}$ alkylbenzyl, X is a direct bond, —O— or S, k is 0 or 1 and and salts of the acids.

Preferred salts are the alkaline metal and earth alkiline metal salts, e.g. from Li, Na, K, Mg, Ca, Sr, Ba.

The cyclic aliphatic and aromatic residues (substituents for the organic group) may be also substituted, for example with halogen like F, Cl or Br, —CN, —NO$_2$, C$_1$ to C$_{18}$ alkyl, C$_3$ to C$_{12}$ cycloalkyl, C$_6$ to C$_{18}$ aryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy.

In the context of the invention the organic group substituent alkyl may be linear or branched and contains preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl.

In the context of the invention the organic group substituent halogen may be F, Cl, Br or I and is preferably F or Cl.

In the context of the invention the organic group substituent alkenyl may be linear or branched and contains preferably 2 to 12 C-atoms, more preferably 2 to 8 C-atoms, most preferably 2 to 6 C-atoms and particularly preferred 2 to 4 C-atoms. Some examples are vinyl, allyl, methylvinyl, but-1-ene-4-yl, but-2-ene-4-yl, but-3-ene-4-yl, 3-methyl-prop-1-ene-3-yl, and the isomers of pentenyl, hexenyl, heptenyl, octenyl, nonenyl, decenyl, undeencyl, dodecenyl, tridecenyl, tetradecenyl, pentadecenyl, hexadecenyl, heptadecenyl and octadecenyl.

In the context of the invention the organic group substituent alkinyl may be linear or branched and contains preferably 2 to 12 C-atoms, more preferably 2 to 8 C-atoms, most preferably 2 to 6 C-atoms and particularly preferred 2 to 4 C-atoms. Some examples are ethinyl, crotonyl, methylethinyl, but-1-ine-4-yl, but-2-ine-4-yl, but-3-ine-4-yl, 3-methyl-prop-1-in-3-yl, and the isomers of pentinyl, hexinyl, heptinyl, octinyl, noninyl, decinyl, undecinyl, dodecinyl, tridecinyl, tetradecinyl, pentadecinyl, hexadecinyl, heptadecinyl and octadecinyl. In the context of the invention the organic group substituent hydroxyalkyl may be linear or branched and contains preferably 1 to 12 C-atoms, more preferably 1 to 8 C-atoms, most preferably 1 to 6 C-atoms and particularly preferred 1 to 4 C-atoms. Some examples are hydroxymethyl, hydroxyethyl, n- or i-hydroxypropyl, n-, i- or t-hydroxybutyl, and the isomers of hydroxypentyl, hydroxyhexyl, hydroxyheptyl, hydroxyoctyl, hydroxynonyl, hydroxydecyl, hydroxyundecyl, hydroxydodecyl, hydroxytridecyl, hydroxytetradecyl, hydroxypentadecyl, hydroxyhexadecyl, hydroxyheptadecyl and hydroxyoctadecyl.

In the context of the invention the organic group substituent halogenalkyl may be linear or branched and contains preferably 1 to 12 C-atoms, more preferably 1 to 8 C-atoms, most preferably 1 to 6 C-atoms and particularly preferred 1 to 4 C-atoms. The holgen may be F, Cl, Br or I, and is preferably F and Cl. Some examples are chloromethyl, dichloromethyl, trichloromethyl, fluoromethyl, difluoromethyl, trifluoromethyl, chloroethyl, n- or i-chloropropyl, n-, i- or t-chlorobutyl, perfluoroethyl and perfluorobutyl.

In the context of the invention the organic group substituent cycloalkyl contains preferably 4 to 8 and more preferred 5 to 7 ring carbon atoms. Examples are cyclopropyl, cyclobutyl, cyclopentyl, cyclohexyl, cycloheptyl, cyclooctyl and cyclododecyl. Preferred groups are cyclopentyl and cyclohexyl.

In the context of the invention the organic group substituent aryl may be naphthyl or preferably phenyl.

In the context of the invention the organic group substituent heteroaryl contains preferably 5 or 6 ring atoms and preferably 1 to 3, more preferably 1 or 2 heteroatoms selected from group consisting of O, S and N. Some examples are pyridinyl, pyrimidinyl, furanyl, pyrrolyl and thiophenyl.

In the context of the invention the organic group substituent cycloalkyl-alkyl is preferably cycloalkyl-methyl or -ethyl, and cycloalkyl means preferably cyclopentyl or cyclohexyl. In the context of the invention the organic group substituent aralkyl is preferably arylmethyl or -ethyl, and aryl means preferably phenyl or naphthyl. Some examples are benzyl, phenylethyl and naphthylmethyl.

In the context of the invention the organic group substituent heteroaralkyl is preferably heteroarylmethyl or -ethyl, and the heteroaryl contains preferably 5 or 6 ring atoms and preferably 1 to 3, more preferably 1 or 2 heteroatoms selected from group consisting of O, S and N. Some examples are pyridinylmethyl or -ethyl, pyrimidinyl, furanylmethyl, pyrrolylmethyl and thiophenylmethyl.

In the context of the invention the organic group substituent alkoxy may be linear or branched and contains preferably 1 to 12 C-atoms, more preferably 1 to 8 C-atoms, most preferably 1 to 6 C-atoms and particularly preferred 1 to 4 C-atoms. Some examples are methoxy, ethoxy, n- or i-propoxy, n-, i- or t-butoxy, and the isomers of pentoxy, hexoxy, heptoxy, octoxy, nonyloxy, decyloxy, undecyloxy, dodecyloxy, tridecyloxy, tetradecyloxy, pentadecyloxy, hexadecyloxy, heptadecyloxy and octadecyloxy.

In the context of the invention the organic group substituent cycloalkyloxy contains preferably 4 to 8 and more preferred 5 to 7 ring carbon atoms. Examples are cyclopropyloxy, cyclobutyloxy, cyclopentyloxy, cyclohexyloxy, cycloheptyloxy, cyclooctyloxy and cyclododecyloxy. Preferred groups are cyclopentyloxy and cyclohexyloxy.

In the context of the invention the organic group substituent aryloxy may be naphthyloxy or preferably phenyloxy.

In the context of the invention the organic group substituent heteroaryloxy contains preferably 5 or 6 ring atoms and preferably 1 to 3, more preferably 1 or 2 heteroatoms selected from group consisting of O, S and N. Some examples are pyridinyloxy, pyrimidinyloxy, furanyloxy, pyrrolyloxy and thiophenyloxy.

In the context of the invention the organic group substituent cycloalkyl-alkyloxy is preferably cycloalkyl-methyloxy or -ethyloxy, and cycloalkyl means preferably cyclopentyl or cyclohexyl.

In the context of the invention the organic group substituent aralkyloxy is preferably arylmethyloxy or -ethyloxy, and aryl means preferably phenyl or naphthyl. Some examples are benzyloxy, phenylethyloxy and naphthylmethyloxy.

In the context of the invention the organic group substituent heteroaralkyloxy is preferably heteroarylmethyl or -ethyl, and the heteroaryl contains preferably 5 or 6 ring atoms and preferably 1 to 3, more preferably 1 or 2 heteroatoms selected from group consisting of O, S and N. Some examples are pyridinylmethyloxy or -ethyloxy, pyrimidinyloxy, furanylmethyloxy, pyrrolylmethyloxy and thiophenylmethyloxy.

In the context of the invention the organic group substituent alkylthio may be linear or branched and contains preferably 1 to 12 C-atoms, more preferably 1 to 8 C-atoms, most preferably 1 to 6 C-atoms and particularly preferred 1 to 4 C-atoms. Some examples are methylthio, ethylthio, n- or i-propylthio, n-, i- or t-butylthio, and the isomers of pentylthio, hexylthio, heptylthio, octylthio, nonylthio, decylthio, undecylthio, dodecylthio, tridecylthio, tetradecylthio, pentadecylthio, hexadecylthio, heptadecylthio and octadecylthio.

In the context of the invention the organic group substituent cycloalkyl contains preferably 4 to 8 and more preferred 5 to 7 ring carbon atoms. Examples are cyclopropylthio, cyclobutylthio, cyclopentylthio, cyclohexylthio, cycloheptylthio, cyclooctylthio and cyclododecylthio. Preferred groups are cyclopentylthio and cyclohexylthio.

In the context of the invention the organic group substituent arylthio may be naphthylthio or preferably phenylthio.

In the context of the invention the organic group substituent heteroarylthio contains preferably 5 or 6 ring atoms and preferably 1 to 3, more preferably 1 or 2 heteroatoms selected from group consisting of O, S and N. Some examples are pyridinylthio, pyrimidinylthio, furanylthio, pyrrolylthio and thiophenylthio.

In the context of the invention the organic group substituent cycloalkyl-alkylthio is preferably cycloalkyl-methylthio or -ethylthio, and cycloalkyl means preferably cyclopentyl or cyclohexyl.

In the context of the invention the organic group substituent aralkylthio is preferably arylmethylthio or -ethylthio, and aryl means preferably phenyl or naphthyl. Some examples are benzylthio, phenylethylthio and naphthylmethylthio.

In the context of the invention the organic group substituent heteroaralkylthio is preferably heteroarylmethylthio or -ethylthio, and the heteroaryl contains preferably 5 or 6 ring atoms and preferably 1 to 3, more preferably 1 or 2 heteroatoms selected from group consisting of O, S and N. Some examples are pyridinylmethylthio or -ethylthio, pyrimidinylthio, furanylmethylthio, pyrrolylmethyfthio and thiophenylmethylthio.

In the context of the invention the organic group substituent alkyl-SO— or —$SO_2$— may be linear or branched and contains preferably 1 to 12 C-atoms, more preferably 1 to 8 C-atoms, most preferably 1 to 6 C-atoms and particularly preferred 1 to 4 C-atoms. Some examples are methyl-SO— or —$SO_2$—, ethyl-SO— or —$SO_2$—, n- or i-propyl-SO— or —$SO_2$—, n-, i- or t-butyl-SO— or —$SO_2$—, and the isomers of pentyl-SO— or —$SO_2$—, hexyl-SO— or —$SO_2$—, heptyl-SO— or —$SO_2$—, octyl-SO— or —$SO_2$—, nonyl-SO— or —$SO_2$—, decyl-SO— or —$SO_2$—, undecyl-SO— or —$SO_2$—, dodecyl-SO— or —$SO_2$—, tridecyl-SO— or —$SO_2$—, tetradecyl-SO— or —$SO_2$—, pentadecyl-SO— or —$SO_2$—, hexadecyl-SO— or —$SO_2$—, heptadecyl-SO— or —$SO_2$— and octadecyl-SO— or —$SO_2$—.

In the context of the invention the organic group substituent cycloalkyl-SO— or —$SO_2$- contains preferably 4 to 8 and more preferred 5 to 7 ring carbon atoms. Examples are cyclopropyl-SO— or —$SO_2$—, cyclobutyl-SO— or —$SO_2$—, cyclopentyl-SO— or —$SO_2$—, cyclohexyl-SO— or —$SO_2$-cycloheptyl-SO— or —$SO_2$—, cyclooctyl-SO— or —$SO_2$— and cyclododecyl-SO— or —$SO_2$—. Preferred groups are cyclopentyl-SO— or —$SO_2$— and cyclohexyl-SO— or —$SO_2$—.

In the context of the invention the organic group substituent aryl-SO— or —$SO_2$— may be naphthyl-SO— or —$SO_2$— or preferably phenyl-SO— or —$SO_2$—.

In the context of the invention the organic group substituent heteroaryl-SO— or —$SO_2$— contains preferably 5 or 6 ring atoms and preferably 1 to 3, more preferably 1 or 2 heteroatoms selected from group consisting of O, S and N. Some examples are pyridinyl-SO— or —$SO_2$—, pyrimidinyl-SO— or —$SO_2$—, furanyl-SO— or —$SO_2$—, pyrrolyl-SO— or —$SO_2$— and thiophenyl-SO— or —$SO_2$—.

In the context of the invention the organic group subsfituent cycloalkyl-alkyl-SO— or —$SO_2$— is preferably cycloalkyl-methyl-SO— or —$SO_2$— or -ethyl-SO— or —$SO_2$—, and cycloalkyl means preferably cyclopentyl or cyclohexyl.

In the context of the invention the organic group substituent aralkyl-SO— or —$SO_2$— is preferably arylmethyl-SO— or —$SO_2$— or -ethyl-SO— or —$SO_2$—, and aryl means preferably phenyl-SO— or —$SO_2$— or naphthyl-SO— or —$SO_2$—. Some examples are benzyl-SO— or —$SO_2$—, phenylethyl-SO— or —$SO_2$— and naphthylmethyl-SO— or —$SO_2$—.

In the context of the invention the organic group substituent heteroaralkyl-SO— or —$SO_2$— is preferably heteroarylmethyl-SO— or —$SO_2$— or -ethyl-SO— or —$SO_2$—, and the heteroaryl contains preferably 5 or 6 ring atoms and preferably 1 to 3, more preferably 1 or 2 heteroatoms selected from group consisting of O, S and N. Some examples are pyridinylmethyl-SO— or —$SO_2$— or -ethyl-SO— or —$SO_2$—, pyrimidinyl-SO— or —$SO_2$—, furanylmethyl-SO— or —$SO_2$—, pyrrolylmethyl-SO— or —$SO_2$— and thiophenylmethyl-SO— or —$SO_2$—.

In the context of the invention the organic group substituent alkyl-CO— may be linear or branched and contains preferably 1 to 12 C-atoms, more preferably 1 to 8 C-atoms, most preferably 1 to 6 C-atoms and particularly preferred 1 to 4 C-atoms. Some examples are methyl-CO—, ethyl-CO—, n- or i-propyl-CO—, n-, i- or t-butyl-CO—, and the isomers of pentyl-CO—, hexyl-CO—, heptyl-CO—, octyl-CO—, nonyl-CO—, decyl-CO—, undecyl-CO—, dodecyl-CO—, tridecyl-CO—, tetradecyl-CO—, pentadecyl-CO—, hexadecyl-CO—, heptadecyl-CO— and octadecyl-CO—.

In the context of the invention the organic group substituent cycloalkyl-CO— contains preferably 4 to 8 and more preferred 5 to 7 ring carbon atoms. Examples are cyclopropyl-CO—, cyclobutyl-CO—, cyclopentyl-CO—, cyclohexyl-CO—, cycloheptyl-CO—, cyclooctyl-CO— and cyclododecyl-CO—. Preferred groups are cyclopentyl-CO— and cyclohexyl-CO—.

In the context of the invention the organic group substituent aryl-CO— may be naphthyl-CO— or preferably phenyl-CO—.

In the context of the invention the organic group substituent heteroaryl contains preferably 5 or 6 ring atoms and preferably 1 to 3, more preferably 1 or 2 heteroatoms selected from group consisting of O, S and N. Some examples are pyridinyl, pyrimidinyl, furanyl, pyrrolyl and thiophenyl.

In the context of the invention the organic group substituent cycloalkyl-alkyl-CO— is preferably cycloalkyl-methyl-CO— or -ethyl-CO—, and cycloalkyl means preferably cyclopentyl or cyclohexyl.

In the context of the invention the organic group substituent aralkyl-CO— is preferably arylmethyl-CO— or -ethyl-CO—, and aryl means preferably phenyl-CO— or naphthyl-CO—. Some examples are benzyl-CO—, phenylethyl-CO— and naphthylmethyl-CO—.

In the context of the invention the organic group substituent heteroaralkyl-CO— is preferably heteroarylmethyl-CO— or -ethyl-CO—, and the heteroaryl contains preferably 5 or 6 ring atoms and preferably 1 to 3, more preferably 1 or 2 heteroatoms selected from group consisting of O, S and N. Some examples are pyridinylmethyl-CO— or -ethyl-CO—, pyrimidinyl-CO—, furanylmethyl-CO—, pyrrolylmethyl-CO— and thiophenylmethyl-CO—.

In the context of the invention the organic group substituent alkoxyalkyl contains preferably in total 2 to 12, more preferably 2 to 8 and most preferably 2 to 6 carbon atoms. The alkoxy may contain 1 to 4 carbon atoms. Some examples are methoxyethyl, methoxyethyl, methoxypropyl, methoxybutyl, methoxypentyl, methoxyhexyl, ethoxymethyl, ethoxyethyl, ethoxypropyl, ethoxybutyl, ethoxypentyl, ethoxyhexyl, propoxymethyl and butoxymethyl.

In the context of the invention the organic group substituent polyoxyalkylene-O—$R_6$ preferably contains 2 to 12 and more preferably 2 to 6 oxyalkylene units, wherein alkylene is preferably ethylene, 1,2- or 1,3-propylene or 1,2-, 1,3- or 1,4-butylene. $R_6$ is preferably H or $C_1$ to $C_4$ alkyl.

In the context of the invention $R_{39}$ and $R_{40}$ in the meaning of alkyl may be linear or branched and contain preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl.

In the context of the invention $R_{39}$ and $R_{40}$ in the meaning of alkylphenyl may be preferably $C_1$ to $C_8$ alkylphenyl, $C_1$ to $C_4$ alkylphenyl. Some examples are methylphenyl, ethylphenyl, n- or i-propylphenyl, n-, i- or t-butylphenyl, hexylphenyl, octylphenyl, dodecylphenyl, and dimethylphenyl.

In the context of the invention $R_{39}$ and $R_{40}$ in the meaning of alkylbenzyl may be preferably $C_1$ to $C_8$ alkylbenzyl, $C_1$ to $C_4$ alkylpenzyl. Some examples are methylbenzyl, ethylbenzyl, n- or i-propylbenzyl, n-, i- or t-butylbenzyl, hexylbenzyl, octylbenzyl, dodecylbenzyl, and dimethylbenzyl.

In the context of the invention $R_{39}$ and $R_{40}$ mean independently from one another preferably H, $C_1$ to $C_4$ alkyl, cyclohexyl, phenyl, benzyl, $C_1$ to $C_4$ alkylphenyl or $C_1$ to $C_4$ alkylbenzyl, or $R_{39}$ and $R_{40}$ together mean tetramethylene, pentamethylene, or the group —$CH_2$—$CH_2$—O—$CH_2$—$CH_2$—.

In the context of the invention $R_{41}$ is in the meaning of alkylene preferably $C_1$ to $C_6$ alkylene, $C_1$ to $C_4$ alkylene, for example methylene, ethylene, propylene or butylene. Most preferred $R_{41}$ is methylene, ethylene, phenylene or benzylene.

In the context of the invention $R_{42}$ in the meaning of alkyl may be linear or branched and contain preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl. $R_{42}$ is peferably H, $C_1$ to $C_{12}$ alkyl, cyclopentyl, cyclohexyl, phenyl, benzyl.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl, $CH_3$—CO—, $C_6H_5$—CO—, $CH_3$—CO—O—, $C_6H_5$—CO—O—, $CH_3$—$SO_2$—O—, $C_6H_5$—$SO_2$—O—, —$NH_2$, —$NHCH_3$, —$NHC_2H_5$, —$NHC_8H_{17}$, —$N(CH_3)_2$, —COOH, —CO—$OCH_3$, —CO—$OC_2H_5$, $SO_3H$, —$SO_2$—$OCH_3$, $SO_2$—$OC_2H_5$, —CO—$NH_2$, —CO—$NCH_3$, —CO—$NHC_2H_5$, —CO—$NHC_8H_{17}$, —CO—$NH(CH_3)_2$, —$SO_2$—$NH_2$, —$SO_2$—$NHCH_3$, —$SO_2$—$NHC_2H_5$, —$SO_2$—$NHC_8H_{17}$, —$SO_2$—$N(CH_3)_2$, $H_2N$—$SO_2$—, methoxymethyl, methoxyethyl, ethoxyethyl, —($OCH_2CH_2$)$_2$—OH, —CN and —$NO_2$.

The number of substituents is arbitrary and depends essentially upon synthetic possibilities, the desired optical properties related to fluorescence and absorption, and the desired solubility.

In a preferred embodiment of the invention the compounds of formula I correspond to formula XXIV,

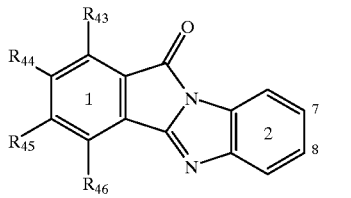

(XXIV)

wherein $R_{43}$, $R_{44}$, $R_{45}$ and $R_{46}$ are independently from one another H, $C_1$ to $C_{18}$ alkyl, $C_1$ to $C_{18}$ alkoxy, $C_1$ to $C_{18}$ alkylthio, aryl, aralkyl, $C_1$ to $C_{12}$ alkyl-aryl or $C_1$ to $C_{12}$ alkyl-aralkyl, and the ring 2 is unsubstituted or substituted as described before, including the preferred substituents.

Preferably at least one of $R_{43}$, $R_{44}$, $R_{45}$ and $R_{46}$ is one of the defined substituents. More preferably $R_{44}$ and $R_{45}$ are one of the defined substituents. Mostly preferred $R_{43}$, $R_{44}$, $R_{45}$ and $R_{46}$ are substituents.

In the context of the invention $R_{43}$, $R_{44}$, $R_{45}$ and $R_{46}$ may be in the meaning of alkyl linear or branched and contains preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl.

In the context of the invention $R_{43}$, $R_{44}$, $R_{45}$ and $R_{46}$ may be in the meaning of alkoxy linear or branched and contains preferably 1 to 12 C-atoms, more preferably 1 to 8 C-atoms, most preferably 1 to 6 C-atoms and particularly preferred 1 to 4 C-atoms. Some examples are methoxy, ethoxy, n- or i-propoxy, n-, i- or t-butoxy, and the isomers of pentoxy, hexoxy, heptoxy, octoxy, nonyloxy, decyloxy, undecyloxy, dodecyloxy, tridecyloxy, tetradecyloxy, pentadecyloxy, hexadecyloxy, heptadecyloxy and octadecyloxy.

In the context of the invention $R_{43}$, $R_{44}$, $R_{45}$ and $R_{46}$ may be in the meaning of alkylthio linear or branched and contains preferably 1 to 12 C-atoms, more preferably 1 to 8 C-atoms, most preferably 1 to 6 C-atoms and particularly preferred 1 to 4 C-atoms. Some examples are methylthio, ethylthio, n- or i-propylthio, n-, i- or t-butylthio, and the isomers of pentylthio, hexylthio, heptylthio, octylthio, nonylthio, decylthio, undecylthio, dodecylthio, tridecylthio, tetradecylthio, pentadecylthio, hexadecylthio, heptadecylthio and octadecylthio.

In the context of the invention $R_{43}$, $R_{44}$, $R_{45}$ and $R_{46}$ may be in the meaning of aryl naphthyl or preferably phenyl.

In the context of the invention $R_{43}$, $R_{44}$, $R_{45}$ and $R_{46}$ may be in the meaning of aralkyl preferably arylmethyl or -ethyl, and aryl means preferably phenyl or naphthyl. Some examples are benzyl, phenylethyl and naphthylmethyl.

In the context of the invention $R_{43}$, $R_{44}$, $R_{45}$ and $R_{46}$ may be in the meaning of alkyl-aryl preferably alkylphenyl, more preferably $C_1$ to $C_8$ alkylphenyl, and most preferably $C_1$ to $C_4$ alkylphenyl. Some examples are methylphenyl, ethylphenyl, n- or i-propylphenyl, n-, i- or t-butylphenyl, hexylphenyl, octylphenyl, dodecylphenyl, and dimethylphenyl.

In the context of the invention $R_{43}$, $R_{44}$, $R_{45}$ and $R_{46}$ in the meaning of alkyl-aralkyl may be preferably alkyl-benzyl, more preferably $C_1$ to $C_8$ alkylbenzyl, and most preferably $C_1$ to $C_4$ alkylbenzyl. Some examples are methylbenzyl, ethylbenzyl, n- or i-propylbenzyl, n-, i- or t-butylbenzyl, hexylbenzyl, octylbenzyl, dodecylbenzyl, and dimethylbenzyl.

In an especially preferred embodiment of the invention the ring 2 is also substituted, particularly in the 7-position, in the 8-position or in both with in organic group substituent. In a particularly preferred embodiment of the invention the compounds of formula I corresponds to formula XXV,

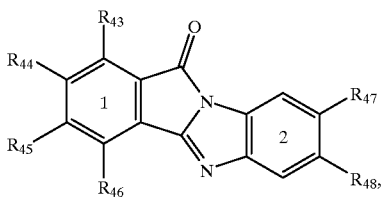

(XXV)

wherein

R₄₃, R₄₄, R₄₅ and R₄₆ are phenyl or $C_1$ to $C_{12}$ alkylphenyl,

R₄₇ is H or an organic group substituent, and

R₄₈ is H or an organic group substituent, or the ring 2 is substituted by 1 or 2 groups selected from —CH=CH—CH=CH—.

The ring 2 is preferably monosubstituted, meaning that at least one of R₄₇ and R₄₈ is an or ganic group substituent.

R₄₃, R₄₄, R₄₅ and R₄₆ are particularly preferred phenyl.

In the context of the invention R₄₇ or R₄₈ in the meaning of an organic group substituent are preferably selected from the group consisting of —CN, —NO₂, $C_1$ to $C_{18}$ alkyl, $C_2$ to $C_{18}$ alkenyl, $C_2$ to $C_{18}$ alkinyl, $C_1$ to $C_{18}$ hydroxyalkyl, $C_1$ to $C_{18}$ halogenalkyl, $C_3$ to $C_{12}$ cycloalkyl, $C_6$ to $C_{18}$ aryl, $C_3$ to $C_{12}$ cycloalkyl-alkyl, $C_6$ to $C_{18}$ aralkyl, $C_1$ to $C_{18}$ alkyloxy, $C_3$ to $C_{12}$ cycloalkyloxy, $C_6$ to $C_{18}$ aryloxy, $C_3$ to $C_{12}$ cycloalkyl-alkyloxy, $C_6$ to $C_{18}$ aralkyloxy, $C_1$ to $C_{18}$ alkylthio, $C_3$ to $C_{12}$ cycloalkylthio, $C_6$ to $C_{18}$ arylthio, $C_3$ to $C_{12}$ cycloalkyl-alkylthio, $C_6$ to $C_{18}$ aralkylthio, $C_1$ to $C_{18}$ alkyl-CO—, $C_3$ to $C_{12}$ cycloalkyl-CO—, $C_6$ to $C_{18}$ aryl-CO—, $C_3$ to $C_{12}$ cycloalkylalkyl-CO—, $C_6$ to $C_{18}$ aralkyl-CO—, —NR₃₉R₄₀, alkoxyalkyl with 2 to 20 carbon atoms, polyoxyalkylene-OR₄₂, —X—(R₄₁)$_k$—C(O)—NR₃₉R₄₀, —X—(R₄₁)$_k$—C(O)—OR₄₂, —X—(R₄₁)$_k$—SO₂—OR₄₂, —X—(R₄₁)$_k$—SO₂—NR₃₉R₄₀, —NH—C(O)—R₄₂ and —O—C(O)—R₄₂, wherein R₃₉ and R₄₀ mean independently from one another H, $C_1$ to $C_{20}$ alkyl, cyclopentyl, cyclohexyl, phenyl, benzyl, $C_1$ to $C_{12}$ alkylphenyl or $C_1$ to $C_{12}$ alkylbenzyl, or R₃₉ and R₄₀ together mean tetramethylene, pentamethylene, or the groups —CH₂—CH₂—O—CH₂—CH₂— or —CH₂—CH₂—NR₃—CH₂—CH₂—, R₃ is H or $C_1$ to $C_6$ alkyl, R₄₁, is $C_1$ to $C_{12}$ alkylene, phenylene or benzylene, R₄₂ means H, $C_1$ to $C_{20}$ alkyl, cyclopentyl, cyclohexyl, phenyl, benzyl, $C_1$ to $C_{,2}$ alkylphenyl or $C_1$ to $C_{12}$ alkylbenzyl, X is a direct bond, —O— or S, k is 0 or 1 and and salts of the acids.

The preferred meanings described before are also valid for the meanings of R₄₇, R₄₈, X and R₃₉ to R₄₂.

R₄₇ and R₄₈ in the meaning of an organic group substituent are most preferably selected from the group consisting of —CN, —NO₂, $C_1$ to $C_{18}$ alkyl, $C_1$ to $C_{18}$ hydroxyalkyl, $C_5$ to $C_7$ cycloalkyl, $C_6$ to $C_{10}$ aryl, $C_7$ to $C_{11}$, aralkyl, $C_1$ to $C_{18}$ alkyloxy, $C_3$ to $C_{12}$ cycloalkyloxy, $C_6$ to $C_{10}$ aryloxy, $C_5$ to $C_7$ cycloalkyl-alkyloxy, $C_7$ to $C_{11}$ aralkyloxy, $C_1$ to $C_{18}$ alkylthio, $C_5$ to $C_7$ cycloalkylthio, $C_6$ to $C_{10}$ arylthio, $C_5$ to $C_7$ cycloalkyl-alkylthio, $C_7$ to $C_{11}$ aralkylthio, $C_1$ to $C_{18}$ alkyl-CO—, $C_5$ to $C_7$ cycloalkyl-CO—, $C_6$ to $C_{10}$ aryl-CO—, $C_5$ to $C_7$ cycloalkyl-alkyl-CO—, $C_7$ to $C_{11}$ aralkyl-CO—, —NR₃₉R₄₀, alkoxyalkyl with 2 to 12 carbon atoms, polyoxyalkylene-OR₄₂, —X—(R₄₁)$_k$—C(O)—NR₃₉R₄₀, —X—(R₄₁)$_k$—C(O)—OR₄₂, —X—(R₄₁)$_k$—SO₂—OR₄₂, —X—(R₄₁)$_k$—SO₂—NR₃₉R₄₀, —NH—C(O)—R₄₂ and —O—C(O)—R₄₂, wherein R₃₉ and R₄₀ mean independently from one another H, $C_1$ to $C_6$alkyl, cyclopentyl, cyclohexyl, phenyl, benzyl, $C_1$ to $C_6$ alkylphenyl or $C_1$ to $C_6$ alkylbenzyl, or R₃₉ and R₄₀ together mean tetramethylene, pentamethylene, or the group —CH₂—CH₂—O—CH₂—CH₂—, R₄₁ is $C_1$ to $C_4$ alkylene, phenylene or benzylene, R₄₂ means H, $C_1$ to $C_{12}$ alkyl, cyclopentyl, cyclohexyl, phenyl, benzyl, $C_1$ to $C_6$ alkylphenyl or $C_1$ to $C_6$ alkylbenzyl, X is a direct bond, —O— or S, k is 0 or 1 and and salts of the acids.

In an especially preferred embodiment of the invention R₄₇ and R₄₈ are selected from the group consisting of —NO₂, $C_1$ to $C_{18}$ alkyl, which is linear or branched, $C_1$ to $C_{18}$ alkyloxy, which is linear or branched, —C(O)OH, or —C(O)—O—$C_1$ to $C_{18}$ alkyl.

The compounds of formula I are partially known or can be easily prepared from unsubstituted or substituted orthophenylenediamines and from unsubstituted or substituted phthalic anhydride as described for example in EP-A-0 456 609.

The fluorescent moiety as a guest chromophore (or "guest polymer") to be used in composition (a2) of the instant invention is derived from a guest molecule as mentioned before, which is covalently linked, directly or via a bridging group, to a polymer backbone.

The bridging group may be selected independently from the bridging groups disclosed above for the host chromophore polymers, including the preferred embodiments.

It is preferred that the solubilities of the guest monomer structures are such that they can readily facilitate themselves to solution polymerization or can be readily dissolved in the comonomers of a bulk polymerization mixture. Solvents available for use in solution polymerizations are well known to those familiar in the art and were mentioned above.

More preferably the guest molecule is a monovalent residue selected from the group consisting of quinacridones, diketopyrrolopyrroles, rhodamines, and perylenes.

Most preferably the selected guests may be unsubstituted or substituted with F, Cl, Br, I, —CN, —NO₂, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloal $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —SO₂, $C_3$ to $C_{12}$ cycloalkyl-SO— or —SO₂, $C_6$ to $C_{18}$ aryl-SO— or —SO₂, $C_5$ to $C_{17}$ heteroaryl-SO— or —SO₂, $C_3$ to $C_{12}$ cycloalkylalkyl-SO— or —SO₂, $C_6$ to $C_{18}$ aralkyl-SO— or —SO₂, $C_5$ to $C_{17}$ heteroaralkyl-SO— or —SO₂, secundary amino with 2 to 30 carbon atoms, and alkoxyalkyl with 2 to 20 carbon atoms.

The cyclic aliphatic and aromatic residues (substituents) may be also substituted, for example with halogens like F, Cl or Br, —CN, —NO₂, $C_1$ to $C_{18}$ alkyl, $C_3$ to $C_{12}$ cycloalkyl, $C_6$ to $C_{18}$ aryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy. The substituent alkyl may be linear or branched and may be substituted with halogens like F or Cl.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

The number of substituents is arbitrary and depends essentially upon synthetic possibilities and the desired optical properties related to fluorescence and absorption.

Preferably the monovalent fluorescent moiety, as a guest chromophore, is selected from the group consisting of monovalent residues having the formulae

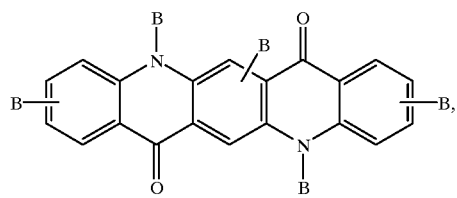

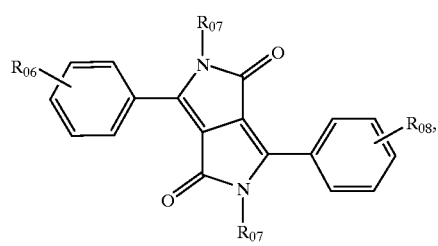

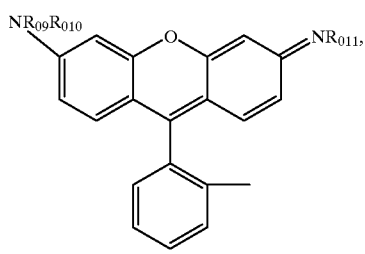

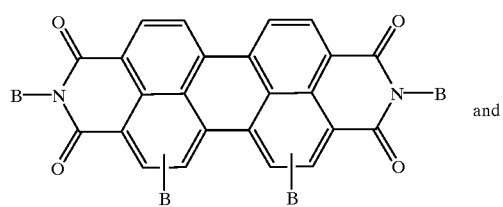

and

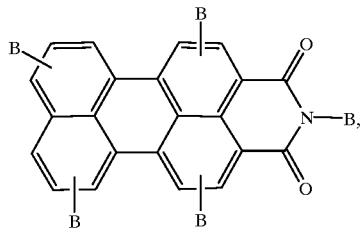

and salts of the rhodamine residue, inclusive salts with the group $=N^+R_{011}R_{012}$, wherein
$R_{06}$ is a bond and both $R_{07}$ and $R_{08}$ or independently H or a substituent, or one of $R_{07}$ is H and the other $R_{07}$, $R_{06}$ and $R_{08}$ are independently H or a substituent, or $R_{08}$ is a bond and the other $R_{07}$ and $R_{06}$ are independently H or a substituent, one of B is a bond and the others are H or a substituent, $R_{011}$ means $C_1$ to $C_{20}$ alkyl, or phenyl or benzyl which are unsubstituted or substituted with $C_1$ to $C_{18}$ alkyl, $R_{09}$ and $R_{010}$ independently of one another mean H, $C_1$ to $C_{20}$ alkyl, or phenyl or benzyl which are unsubstituted or substituted with $C_1$ to $C_{18}$ alkyl, $R_{012}$ is H or $C_1$ to $C_{18}$ alkyl, whereby the rings are unsubstituted or substituted with subsituents F, Cl, Br, I, —CN, —NO$_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —SO$_2$, $C_3$ to $C_{12}$cycloalkyl-SO— or —SO$_2$, $C_6$ to $C_{18}$ aryl-SO— or —SO$_2$, $C_5$ to $C_{17}$ heteroaryl-SO— or —SO$_2$, $C_3$ to $C_{12}$ cycloalkylalkyl-SO— or —SO$_2$, $C_6$ to $C_{18}$ aralkyl-SO— or —SO$_2$, $C_5$ to $C_{17}$ heteroaralkyl-SO— or —SO$_2$, secundary amino with 2 to 30 carbon atoms, and alkoxyalkyl with 2 to 20 carbon atoms.

The cyclic aliphatic and aromatic residues may be also substituted, for example with F, Cl, Br, I, —CN, —NO$_2$, $C_1$ to $C_{18}$ alkyl, $C_3$ to $C_{12}$ cycloalkyl, $C_6$ to $C_{18}$ aryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy. The alkyl may be substituted with halogen like F, Cl or Br.

More preferred substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

$R_{011}$ means preferably $C_1$ to $C_{18}$ alkyl, which may linear or branched, or phenyl or benzyl which are unsubstituted or substituted with $C_1$ to $C_{12}$ alkyl, and $R_{09}$ and $R_{010}$ independently of one another mean preferably H, $C_1$ to $C_{18}$ alkyl, or phenyl or benzyl which are unsubstituted or substituted with $C_1$ to $C_{12}$ alkyl. Examples are methyl, ethyl, and the isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, phenyl, benzyl, methylphenyl, ethylphenyl, propylphenyl, butylphenyl, pentylphenyl, hexylphenyl, heptylphenyl, octylphenyl, methylbenzyl, ethylbenzyl, propylbenzyl, butylbenzyl, pentylbenzyl, hexylbenzyl, heptylbenzyl, and octylbenzyl.

$R_{012}$ means preferably $C_1$ to $C_{12}$ alkyl, more preferably $C_1$ to $C_8$ alkyl and most preferably $C_1$ to $C_4$ alkyl.

Suitable salts may be derived from inorganic or organic acids, for example HCl, HBr, $H_2SO_4$, carboxylic acids like acetic acid, chloro- or fluoroacetic acids, propionic acid, benzoic acid, chloro- or fluorobenzoic acids, sulfonic acids like methylsulfonic acid, chloro- or fluoromethylsulfonic acids, phenylsulfonic acid, toluylsulfonic acid, and chloro- or fluorobenzenesulfonic acids.

More preferred fluorescent moieties as guest chromophores are residues of the following formulae:

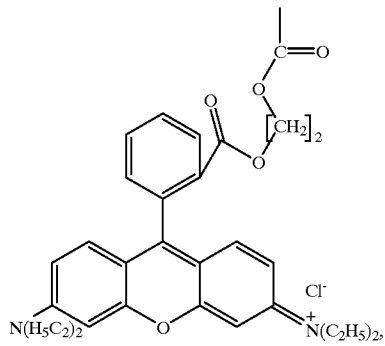

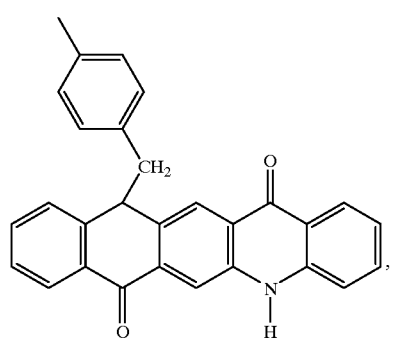

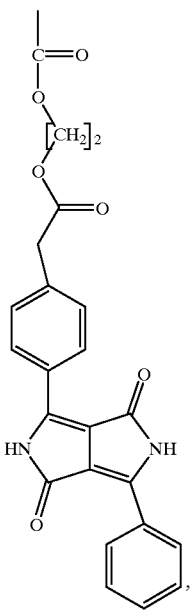

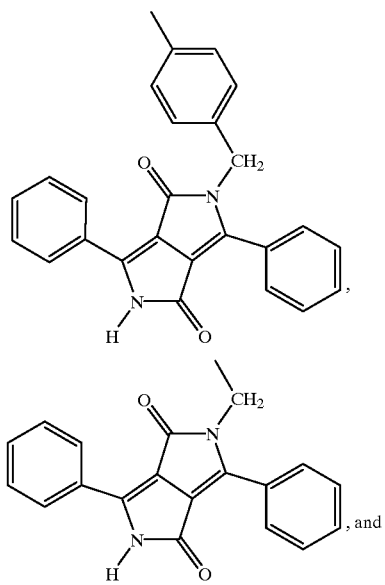

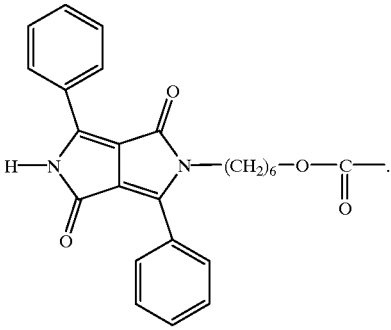

The guest moieties are linked through functional groups bonded to structural units of the backbone. Examples of functional groups are —OH, —SH, —NH$_2$, —NHR$_2$, —CH=O, carboxylic acid, —SO$_3$H, epoxide, vinyl or isocyanate, wherein R$_2$ is preferably H or C$_1$ to C$_4$ alkyl.

The polymers can be selected from the same polymer natural or synthetic polymers as disclosed for the composition (a1). Examples are given above.

The guest chromophore linked to the polymers may be derived from mono-functional or polyfunctional guest molecules. Preferably the molecules are mono- to trifunctional, especially preferred are mono- or difunctional. The polymer may be composed of monomeric units with covalently linked monovalent and/or divalent residues of a guest chromophore, and optionally from other comonomeric units.

The polymers with with covalently linked guest chromophores may be homopolymers or copolymers. The monomeric units containing the guest (designated as m) are preferably present in the range from 0.001 to 0.5, more preferably 0.01 to 0.3, and most preferably 0.001 to 0.05. Non-fluorescent monomeric units (designated as n) being in the range from 0 to 0.999, whereby m and n are typically selected such as to satisfy m+n=1.

The polymers may be composed of recurring structural units of formula (XXVI)

(XXVI)

or may be composed of recurring crosslinking units of formula (XXVIa), alone or in combination with structural units of formula (XXVIa)

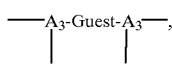

(XXVIa)

wherein

A$_1$ and A$_3$ are trivalent organic residues,

Guest is a monovalent or divalent fluorescent moiety as a guest chromophore, as defined before, which is covalently linked, either directly or via a bridging group, whereby A$_1$ and A$_3$ are copolymerisable when used in combination.

The polymer may additionally contain structural units of formula (XXVII)

(XXVII)

wherein A$_4$ means the same or a different divalent residue copolymerizable with A$_1$ and/or A$_3$.

A$_1$, A$_3$, and A$_4$ may be derived from monomers selected from the group consisting of olefins, polyolefines like di- or triolefines, polyalcohols like diols and triols, polyamines like diamines and triamines, polyisocyanates like di- or triisocyanates, polycarboxylic acids like di- and tricaboxylic acids, and polyepoxides like di- and triepoxides.

The structural elements of formula (XXVI) may be present in an amount of 0.01 to 50 weight %, preferably 0.1 to 30 weight %, more preferably 0.1 to 5 weight %, most preferably 0.1 to 3 weight % of the polymer.

The structural elements of formula (XXVIa) may be present in an amount of 0.01 to 50 weight %, preferably 0.1 to 30 weight %, more preferably 0.1 to 5 weight %, most preferably 0.1 to 3 weight % of the polymer.

In a preferred embodiment the polymers according to the invention contain recurring structural units of formula (XXVIII), and optionally recurring structural units of formula (XXIX)

(XXVIII)

(XXIX)

wherein

X$_1$ and X$_2$ each independently of one another mean a direct bond, or X$_1$ and X$_2$ each independently of one another mean —O—, —S—, —NR$_2$—, —C(O)—O—, —O—C(O)—, —O—C(O)—O—, —SO$_2$—O—, —O—SO$_2$—, —O—SO$_2$—O—, —NR$_2$—C(O)—, —C(O)—NR$_2$—, —NR$_2$—C(O)—O—, O—C(O)—NR$_2$—, —NR$_2$—C(O)—NR$_2$—, —NR$_2$—SO$_2$—, —SO$_2$—NR$_2$—, —NR$_2$—SO$_2$—O—, —O—SO$_2$—NR$_2$— or —NR$_2$—SO$_2$—NR$_2$—, R$_1$ means a bivalent bridging group, Guest means a monovalent fluorescent guest chromophore, R$_2$ means H, C$_1$–C$_{12}$ alkyl, C$_5$- or C$_6$ cycloalkyl, C$_5$- or C$_6$ cycloalkylmethyl or -ethyl, phenyl, benzyl or 1-phenyl-2-ethyl, R$_3$ means a direct bond, C$_1$–C$_{18}$ alkylene, C$_5$- or C$_6$-cycloalkylene, C$_6$–C$_{10}$ arylene or C$_7$–C$_{12}$ aralkylene, r and s independently of one another mean the numbers 0 or 1, with the proviso that if s is 0, r is 0, R$_4$ and R$_5$ each independently of one another mean H, C$_1$–C$_6$ alkyl, C$_6$–C$_{10}$ aryl or C$_7$–C$_{12}$ aralkyl, R$_6$ means H or the group —C(O)O—R$_{11}$, R$_7$ means H, C$_1$–C$_6$ alkyl, C$_6$–C$_{10}$ aryl or C$_7$–C$_{12}$ aralkyl, R$_8$ means H, F, Cl, CN, C$_1$–C$_6$ alkyl or C$_6$–C$_{10}$ aryl, R$_9$ means H, C$_1$–C$_6$ alkyl or —C(O)O—R$_{11}$, R$_{10}$ means H, C$_1$–C$_6$ alkyl, C$_6$–C$_{10}$ aryl, C$_7$–C$_{12}$ aralkyl, imidazolyl, pyrrolidonyl, F, Cl, CN or the group —X$_1$—(R$_1$)$_r$—(X$_2$)$_s$—H, and R$_{11}$ means H, K, Na, C$_1$–C$_{18}$ alkyl, C$_1$–C$_{18}$ hydroxyalkyl, cyclohexyl, cyclopentyl, cyclohexylmethyl, phenyl, C$_1$–C$_4$ alkylphenyl, benzyl or C$_1$–C$_4$ alkylbenzyl.

For X$_1$, X$_2$, R$_1$, R$_2$, R$_3$, r, s and Guest the meanings and preferred embodiments as described before are valid for the structural elements of formulae XXVIII and XXIX.

R$_4$ and R$_5$ as alkyl mean preferably C$_1$–C$_4$ alkyl, for example methyl, ethyl, n- or i-propyl and n-, i- or t-butyl; as aryl preferably naphthyl or phenyl; and as aralkyl preferably benzyl. Especially preferred R$_4$ is H and R$_5$ is H or methyl.

$R_6$ means preferably H, —C(O)OH or —C(O)O—$C_1$ to $C_4$-alkyl.

$R_7$ means as alkyl preferably $C_1$ to $C_4$ alkyl, for example methyl, ethyl, n- or i-propyl, and n-, i- or t-butyl; as aryl preferably naphthyl or phenyl and as aralkyl preferably benzyl. Especially preferred $R_7$ is H.

As alkyl $R_8$ means preferably $C_1$ to $C_4$ alkyl, for example methyl, ethyl, n- or i-propyl and n-, i- or t-butyl; and for aryl it is preferably phenyl or naphthyl. Especially preferred $R_8$ is H, Cl, CN, phenyl or $C_1$ to $C_4$ alkyl.

$R_9$ means as alkyl preferably $C_1$–$C_4$ alkyl, for example methyl, ethyl, n- or i-propyl and n-, i- or t-butyl. In the group —C(O)O—$R_{11}$, $R_{11}$ means preferably H or $C_1$–$C_{12}$ alkyl, more preferably $C_1$–$C_6$ alkyl, like for example methyl, ethyl, propyl, butyl, pentyl, hexyl, heptyl, octyl, nonyl, decyl, undecyl, dodecyl, tetradecyl, hexadecyl and octadecyl. Especially preferred $R_9$ is H, —C(O)OH or —C(O)—O—$C_1$–$C_4$ alkyl.

$R_{10}$ means as alkyl preferably $C_1$–$C_4$ alkyl, for example methyl, ethyl, n- or i-propyl and n-, i- or t-butyl, as aryl preferably phenyl and naphthyl, and as aralkyl preferably benzyl. $R_{10}$ means preferably H, $C_1$–$C_4$ alkyl, phenyl, pyrrolidonyl, F, Cl, CN or the group —$X_1$—$(R_1)_r$—$(X_2)_s$—H.

$R_{11}$ may be for example H, K, Na, $C_1$–$C_6$ alkyl, $C_1$–$C_6$-hydroxyalkyl, cyclohexyl, cyclopentyl, cyclohexylmethyl, phenyl, methylphenyl, benzyl or methylbenzyl.

The structural elements of formula (XXVIII) may be present in an amount of 0.01 to 50 weight- %, preferably 0.1 to 30 weight- %, more preferably 0.1 to 5 weight- %, most preferably 0.1 to 3 weight- %, related to total weight of the polymer. The structural elements of formula (XXIX) may be present in an amount of 0 to 99.99 weight- %, preferably 10 to 99.9 weight- %, and more preferably 50 to 99.9 weight- %, related to the total weight of the polymer.

The polymers with the structural elements of formula (XXVIII) and optionally (XXIX) may be crosslinked in combination with multi-functional monomers, for example with 0.01 to 80 weight- %, preferably 0.1 to 60 weight- % of these monomers, related to 100 g of the polymer. Depending upon the kind of the polymer at least trifunctional carboxylic acids, isocyanates, alcohols, amines, vinyls or epoxides may be used. Furthermore residues containing at least two olefinically (ethylenically) unsaturated groups may be employed. The ethylenically unsaturated crosslinking agent may be selected from the group consisting of divinylbenzol, bi-methylmaleinimide-alkylene like bi-(dimethylmaleinimidyle)-methylene or -ethylene, acrylic acid- or methacrylic acid esters or -amides of polyols, preferably diols to tetrols, or polyamines respectively, preferably diamines to tetramines.

Preferred ethylenically unsaturated crosslinking agents are selected from the group of acrylic or methacrylic acid esters of aliphatic, cycloaliphatic and cycloaliphatic-aliphatic diols to terols and diamines to tetramines containing especially preferred 2 to 12, and particularly preferred 2 to 8 C-atoms. Some examples of these diols are alkylenediols like ethylenglycol, 1,2- or 1,3-propanediol, 1,2-, 1,3- and 1,4-butanediol, pentanediol, hexanediol, octanediol, decanediol, dodecanediol, cyclohexanediol, di(hydroxymethyl)-cyclohexane, polyoxyalkylendiols from preferably $C_2$–$C_6$ alkylendiols with preferably 2 to 100 alkylenediol units, more preferably 2 to 50 alkylenediol units, and most preferably 2 to 20 alkylenediol units, like for example polyethylenediols, polypolypropylenediols, polybutylenediols and polyethylene/polypropylenediols, further 1,1,1-trihydroxymethylethane or -propane, pentaerythritol and dipentaerythritol. Some examples for polyamines are ethylenediamine, 1,3- and 1,3-propanediamine, 1,2-, 1,3- and 1,4-butanediamine, 1,6-hexanediamine, diethylenetriamine, triethylenetetramine, cyclohexanediamine, (aminomethyl)cyclohexaneamine, isophorondiamine and di-(aminomethyl)cyclohexane.

In a preferred embodiment of the invention the polymers contain structural elements of the formulae (XXX)

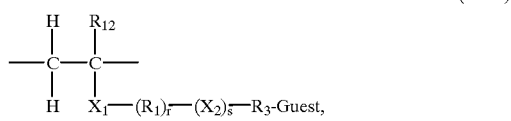

(XXX)

wherein $R_{12}$ is H or methyl, and $X_1$, $X_2$, $R_1$, $R_3$, Guest, r and s have the same meanings as described before, including the preferred embodiments; and optionally structural elements of formula (XXXIX).

The group —$X_1$—$(R_1)_r$—$(X_2)_s$—$R_3$— in the structural elements of formula (XXXX) mean preferably —C(O)—O—, —C(O)—O—$C_2$–$C_6$ alkylene-O—C(O)—, —C(O)—O—$(C_2$–$C_6$ alkylene-O$)_u$—C(O)— with u being a number from 2 to 10, —O—C(O)—$C_6H_5$—$CH_2$—, —O—C(O)—$C_6H_5$- or —O—C(O)—$C_1$ to $C_{12}$ alkylene.

The polymers with the structural elements of formula (XXVIII) or (XXX), and optionally structural elements of formula (XXIX) may contain additionally identical or different structural elements of formula (XXXI)

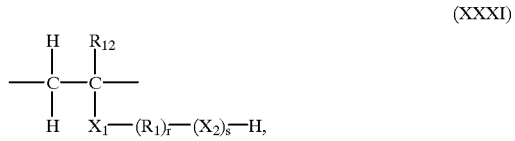

(XXXI)

wherein $R_{12}$, $X_1$, $X_2$, $R_1$, r and s have the meanings given before, inclusive of the preferred embodiments. These structural elements are especially present when the groups Host and Guest are introduced to the polymer through reaction between pendant functional groups on the polymer and functional groups on the respective host and guest molecules.

The polymers with the structural elements of formula (XXVIII) or (XXX), and optionally structural elements of formula (XXIX), contain preferably identical or different structural elements of formula (XXXII) as preferred units of formula (XXIX)

(XXXII)

wherein
$R_{12}$ means H or methyl, and
$R_{13}$ means H, $C_1$–$C_4$ alkyl, $C_1$–$C_4$ alkoxy, —CN, Cl, phenyl, pyrrolidonyl, pyridinyl, imidazolyl, —C(O)OR$_{14}$ or —C(O)—NR$_{15}$R$_{16}$, $R_{14}$ means H or $C_1$–$C_{18}$- and preferably $C_1$–$C_{12}$ alkyl, and $R_{15}$ and $R_{16}$ independently of one another mean H or $C_1$–$C_{12}$-, and preferably $C_1$–$C_6$ alkyl.

The polymers with the structural elements of formula (XXVIII) or (XXX), and optionally identical or different structural elements of formula (XXXIX) or formula (XXXXII), may additionally contain structural elements of formulae (XXXIII) or (XXXIV) as preferred units of crosslinking agents,

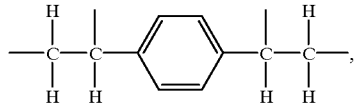
(XXXIII)

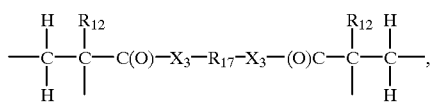
(XXXIV)

wherein
$R_{12}$ means H or methyl,
$X_3$ means —O—, —NH— or —N($C_1$–$C_4$-alkyl)-, and
$R_{17}$ means $C_2$–$C_{12}$- and preferably $C_1$–$C_6$ alkylene, cyclohexylene, cyclohexanedimethylene, phenylene, or $X_3$ means —O— and $R_{17}$ means $C_2$–$C_6$ alkylene-($C_2$–$C_6$ alkylen-O)$_{2\ to\ 20}$-$C_2$–$C_6$ alkylene.

The polymerisates and preferred polymerisates described before may contain additionally same or different ionic structural elements, for example of formula (XXXV)

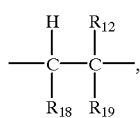
(XXXV)

wherein
$R_{12}$ means H or methyl,
$R_{18}$ means H and $R_{19}$ means —C(O)O$R_{20}$, —SO$_3$R$_{20}$, —C$_6$H$_4$—COOR$_{20}$, —C$_6$H$_4$—SO$_3$R$_{20}$, —C$_6$H$_4$—R$_{21}$ or —C(O)—X$_4$—C$_2$–C$_6$ alkylene-R$_{22}$,
$X_4$ means —O— or —NH—, $R_{18}$ and $R_{19}$ mean independently of one another —C(O)OR$_{20}$ or —C(O)—X$_4$—C$_2$–C$_6$ alkylene-R$_{22}$,
$R_{20}$ means an alkaline metal, preferably Li, Na or K,
$R_{21}$ means an ammonium group or an ammoniummethyl group, and
$R_{22}$ means an ammonium group.

The ammonium group or the ammonium in the ammoniummethyl group may be derived from primary, secondary or tertiary amine groups; preferred are quaternary ammonium groups. The ammonium groups or the ammonium in the ammoniummethyl group may correspond to the formula (XXXVI)

—$^+$NR$_{23}$R$_{24}$R$_{25}$   (XXXVI), wherein
$R_{23}$, $R_{24}$ and $R_{25}$ are independently from one another H, $C_1$–$C_{18}$-, preferably $C_1$–$C_{12}$- and more preferably $C_1$–$C_6$ alkyl, $C_5$- or $C_6$cycloalkyl, phenyl, benzyl, 1-phenyl-2-ethyl, or $R_{23}$ and $R_{24}$ together are tetramethylene, pentamethylene or —CH$_2$CH$_2$—O—CH$_2$CH$_2$—;$R_{26}$ has the meaning as given before.

Suitable counter anions may be derived from inorganic or organic acids, like for example carboxylic acids, sulfonic acids and halogenhydrogen acids. Preferred counter anions are chloride and bromide.

The polymerisates and preferred polymerisates described before may contain additionally structural elements with acidic groups like for example —C(O)OH or —SO$_3$H, especially when emulsion polymerisates are involved.

The structural elements with acidic groups may correspond to the formula (XXXVII)

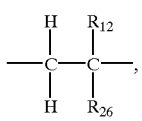
(XXXVII)

wherein
$R_{12}$ means H or methyl,
$R_{27}$ means H and $R_{26}$ means —C(O)OH, —SO$_3$H, —C$_6$H$_4$—COOH, —C$_6$H$_4$—SO$_3$H, or
$R_{26}$ and $R_{27}$ means —C(O)OH.

Polymers with amino or acidic groups may be preferably soluble in water or they may be prepared by emulsion polymerization for dispersing and/or dissolving monomers. In another preferred embodiment the polymers according to the invention may be crosslinked with difunctional guest molecules. These polymers may contain recurring structural elements of formula (XXXVIII), alone or together with structural elements of formula (XXX)

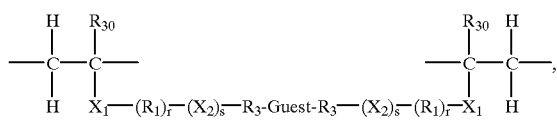
(XXXVIII)

wherein
$R_1$, $R_3$, $R_{12}$, $X_1$, $X_2$, r, s and -Guest- have the meanings given before, inclusive of preferred embodiments.

The structural elements of formula (XXXVIII) may be present in an amount of 0.01 to 50 weight- %, preferably 0.1 to 30 weight- %, more preferably 0.1 to 5 weight- %, most preferably 0.1 to 3 weight- % of the polymer.

The above crosslinked polymers with one or both structural elements of formula (XXXVIII) may contain structural elements of formulae (XXVI), (XXVII), (XXXI), (XXXIII), (XXXIV), (XXXV), (XXXVI) and (XXXVII) alone or in any combination of at least 2 of these structural elements, or may contain structural elements of preferred residues formulae (XXIX), (XXX) and (XXXII), and further (XXXXIII), (XXXXIV), (XXXXV), (XXXXVI) and XXXXVII) alone or in any combination of at least 2 of these structural elements.

Some preferred examples of structural units of formula (XXXVIII) are

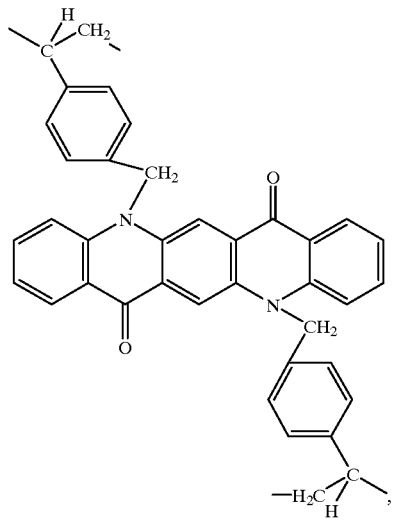

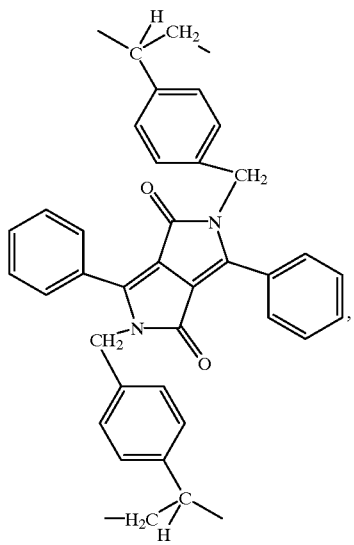

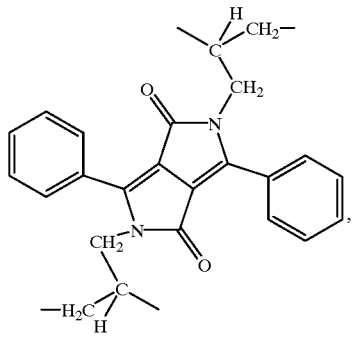

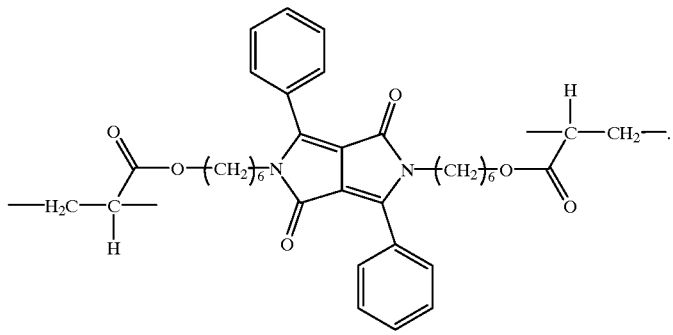

The polymers according to the invention may be random, block, alternating, graft or emulsion polymers (latices).

The preparation of polymers and their immobilization is well known in the art and may be carried out as described for the polymers of composition (a1).

The monomers are partially novel and partially known or they can be prepared by known or analogous methods.

Functional guest chromophores are known or can be synthesized by known or analogous methods for their synthesis described before by employing optionally protected functional intermediates. Guest chromophores may be obtained from chromophore precursors containing NH-groups by the reaction with halogenalkanes which additionally contain a functional group such as a carboxylic group or a vinyl group.

Multi-functional guest compounds can be prepared in a similar fashion to those described in the literature EP 0 337 951.

The solid composition (a2) according to the instant invention comprises a host chromophore and an effective amount of a guest chromophore. The weight ratio between the host chromophores and the guest chromophores is preferably 50:50 to 9999:1, more preferably 60:40 to 999:1 and most preferably 70:30 to 999:1.

Another aspect of this invention is the preparation of semi-interpenetrating networks that employ linear (thermoplastic) polymers of composition (a2). By admixing a guest containing polymer and host molecules with multi-functional comonomers or multi-functional prepolymers, such that neither the guest polymer or host molecules participate in the polymerisation reaction, but are entangled and dispersed respectively therein, a highly fluorescent semi-interpenetrating network is obtained. Alternatively, the host molecules can be dispersed throughout the crosslinked network, by swelling the crosslinked system in a solvent containing host molecules, and allowing them to diffuse into the network. Preferred crosslinking systems include, but are not restricted to, alcohol-isocyanates, amine-isocyanates, multivinyl monomers, multi-vinyl containing prepolymers, multi-allyl containing prepolymers, amine-epoxy and acid-epoxy.

Another aspect of this invention is the preparation of an interpenetrating network employing the polymers of composition (a2). Such a system preferably employs guest polymers that contain pendant- or end functional groups that can participate in the crosslinking reaction with multi-vinyl or multi-functional comonomers or prepolymers, to afford a highly fluorescent crosslinked network. The host molecule are dispersed in the crosslinking reaction medium. Alternatively, if the crosslinked polymer is swollen in a solvent containing host molecules, the host molecules can diffuse into the network. Preferred crosslinking systems include, but are not restricted to, alcohol-isocyanates, amine-isocyanates, multivinyl monomers, multi-vinyl containing prepolymers, multi-allyl containing prepolymers, amine-epoxy and acid-epoxy.

A further preferred embodiment of the present invention concerns a mixture of the inventive host polymer and the inventive guest polymer.

According to the instant invention, the host polymers and guest polymers (hereinafter referred to as "composition b") are prferably identical to those previously described in compositions (a1) and (a2), respectively. These polymers are incorporated by reference, inclusive of the preferred embodiments to host and guest chromophores, and the polymer backbones.

The composition (b) is for example a blend of linear (thermoplastic) polymers. It is proffered that the respective polymers be compatible to ensure the occurance of an effective, preferably full, energy transfer between the host and guest components.

The composition (b) is for example a thermosetting resin containing recurring structural units with covalently linked host chromophores, and containing dissolved and homogeneously distributed a guest chromophore, or recurring structural units with covalently linked guest chromophores and containing dissolved and homogeneously distributed an host chromophore. Preferred thermosetting resins are composed of ethylenically unsaturated monomers, which have been described above for the compositions (a1) and (a2) polymers, incorporated herein by reference, inclusive preferred embodiments.

Another aspect of this invention is the preparation of semi-interpenetrating networks employing the polymers of composition (b). By admixing a host containing polymer and a corresponding guest containing polymer together with multi-functional comonomers or multi-functional prepolymers, such that neither the host polymer or guest polymer do not participate in the reaction, but are entangled in the resultant infusible network, a highly fluorescent semi-interpenetrating network can be afforded. Preferred crosslinking systems include, but are not restricted to, alcohol-isocyanates, amine-isocyanates, multivinyl monomers, multi-vinyl containing prepolymers, multi-allyl containing prepolymers, amine-epoxy and acid-epoxy.

Another aspect of this invention is the preparation of semi-interpenetrating networks employing the polymers of composition (b), wherein either the host polymer or guest polymer can participate in the network forming reaction. By admixing a host containing polymer and a corresponding guest containing polymer together with multi-functional comonomers or multi-functional prepolymers, such that either the host polymer or guest polymer participates in the crosslinking reaction. The polymer selected not to participate in the network forming reaction is resultantly entangled in the crosslinked network. In such cases a highly fluorescent semi-interpenetrating networks can be generated. Preferred crosslinking systems include, but are not restricted to, alcohol-isocyanates, amine-isocyanates, multivinyl monomers, multi-vinyl containing prepolymers, multi-allyl containing prepolymers, amine-epoxy and acid-epoxy.

Another aspect of the invention is the preparation of interpenetrating networks employing the polymers of composition (b). Such a system preferably employs host and guest polymers which contain pendent or end-functional groups that facilitate themselves to participate in a crosslinking reaction with multifunctional comonomers or prepolymers. The furnished materials are highly fluorescent crosslinked networks. Preferred crosslinking systems include, but are not restricted to, alcohol-isocyanates, amine-isocyanates, multivinyl monomers, multi-vinyl containing prepolymers, multi-allyl containing prepolymers, alcohol-epoxy, amine-epoxy and acid-epoxy.

The solid composition (b) according to the instant invention comprises a host chromophore and a guest chromophore. The weight ratio between the host chromophores and the guest chromophores is 50:50 to 9999:1, preferably 60:40 to 999:1 and more preferably 70:30 to 999:1.

Another embodiment of the present invention relates to a process for the preparation of the inventive solid composition, characterized in admixing a host polymer and a guest chromophore, or a guest polymer and a host chromophore, or a host polymer and a guest polymer, preferably in the presence of a solvent and removing the solvent after the admixing.

Another embodiment of the present invention relates to a process for the preparation of the inventive solid compositions, characterised in polymerising a host chromophore monomer or a prepolymer thereof in the presence of a dissolved guest chromophore, or a guest chromophore monomer or a prepolymer thereof in the presence of a dissolved host chromophore, optionally together with a non-fluorescent monomer.

Another preferred embodiment of the present invention relates to a process for the preparation of the solid compositions (a1), (a2) and (b) according to the invention, characterized in (1) homogeneously mixing together the host component and the guest component, whereby at least one component is a polymer (host polymer and/or guest polymer); or (2) polymerizing a host chromophore monomer or a prepolymer thereof in the presence of a dissolved guest chromophore, or a guest chromophore monomer or a prepolymer thereof in the presence of a dissolved host chromophore, optionally together with non-fluorescent monomers; or (3) in case the composition (a1) includes a molecularly dissolved pigment generated from a pigment precursor having for example an alkoxycarbonyl group, then the host component and the guest component preferably are homogeneously mixed, and the alkoxycarbonyl group subsequently removed after the mixing or polymerization.

Various processes for mixing the host and guest components can be used.

Generally, mixing processes are classified into melting processes, dry processes and wet processes.

In the context of the invention mixing of the materials can be achieved through dissolution of the components in a common solvent and followed by the subsequent evaporation of the solvent; precipitation from a good solvent into a poor solvent (vigorous stirring can be applied); freeze-drying; and precipitation during polymerization of polymerizable monomers or oligomers, preferably under vigorous stirring.

Suitable inert solvents have been described previously.

In the precipitation process, differences in the relative solubilities of the components is utilised, wherein upon dissolution into a common good solvent, the host and guest components are added to large excess of a vigorously stirred poor solvent. The furnished materials are highly fluorescent and exhibit all the features characteristic of host/guest materials.

In the process of freeze-drying, a steady state of components and solvent is generated by freezing a solution, wherein the components are in homogeneous distribution. This state is maintained upon removal of the solvent by freeze-drying. The furnished materials are highly fluorescent and exhibit all the features characteristic of host/guest materials.

If one the components is crosslinked it may be possible to introduce the corresponding component by swelling the crosslinked material in a good solvent that contains the counter material dissolved therein. After penetration of the counter material into the gel, removal of the solvent furnishes highly fluorescent host/guest materials.

A further means of mixing the components is by melting-mixing them together at temperatures below the respective decomposition temperatures, and optionally under pressure. This process can be carried out in thermoplastic molding equipment such as injection, extrusion or press molding processes.

Another possibility is dissolve a host or guest chromophore monomer or a prepolymer thereof (like oligomers) in the presence of the respective guest or host chromophores with or without solvent and to polymerize the mixture in a known manner like bulk, solution or emulsion polymerization forming a polymer precipitate. Using emulsion polymerizations finely divided particles can be obtained. This process is suitable to generate crosslinked polymers.

When molecularly dissolved pigments are desired as guest chromophores, they can be generated from pigment precursors containing protecting groups, which are subsequently removed after the preparation and drying of the compositions (a2). The amount of pigment regenerated should be controlled to avoid formation of nano-sized pigment particles. The upper limit is preferably 2.5 percent by weight and more preferably 2 percent by weight, related to the composition (a2).

In the context of the invention, wherein a pigment is deliberated from a pigment precursor, removal of the protecting groups covalently linked to the pigment is required. The protecting groups may additionally have the function to solubilize the insoluble pigment. Removal of the protecting groups may be achieved by chemical means like acid, base, catalysts present in the composition; by irradiation or heating the precipitate, or a combination of these methods. A preferred method is heating, whereby acids, bases and or catalysts may assist to decrease the decomposition temperature of the pigment precursor.

The actual temperatures employed must be lower than the decomposition temperatures of the respective host chromophore and polymers used in the composition. The temperature must be also below the melting temperatures of the host chromophore and the polymers to avoid migration and aggregation of the deliberated pigment. The temperature must be also above the decomposition temperature of the pigment precursor.

The temperature range for the heat treatment of the precipitate may for example be from 50 to 250° C. preferably 70 to 220° C. more preferably 80 to 200° C. and most preferably 100 to 180° C. Higher temperatures may be employed when crosslinked polymers are heated.

When using a polymer matrix comprising pendent host, the selected decomposition temperature of the pigment precursor may also depend on the softening or glass transition temperature of the polymer. This is to avoid migration of the deliberated pigment molecules, which may in turn lead to the generation of undesired nano-size pigment particles. It is also found that the heating temperature may be about or slightly above the softening or glass transition temperature. Furthermore, employing short and optionally repeated heating cycles and times can be a useful means of avoiding any undesired aggression. Short and spared heating times can be achieved, for example, using microwaves or heat radiation. These. methods can also be employed to polymers with low glass transition temperatures like polyolefines or rubbers.

The composition generated by the process of decomposing a pigment precursor affords a material that contains a normally insoluble pigment in the molecularly dissolved state. Additonally, compositions according to the present invention generally do not show the typical color expected of the pigment in compositions of polymer and pure aggregated pigment, or the typical mixed color in compositions containing a host chromophore optionally together with a polymer matrix. The color of the compositions can be used to detect if the pigment precursor has fully decomposed and remains molecularly dissolved.

The compound 1,2,3,4-tetraphenyl-benzo[4,5] imidazo[2, 1-a]isoindol-11-one and its derivatives, which are a preferred group of host compounds used in this invention, possess an absorption maximum at around 370 nm, which lies in the UV region. However, their excitation wavelengths stretch from around 350 nm, in the UV, to 450 nm, in the visible region of the electromagnetic spectrum. Consequently, host/guest type materials employing this class of compounds, as a host, can span a broad number of applications as they readily facilitate themselves to excitation by both UV and daylight radiation sources. Therefore, these materials could be rendered very useful as coloring agents in applications such as road markings and traffic signs for night and daylight uses, as they exhibit brilliant daylight fluorescence and can also be excited by the UV radiation of motor vehicles halogen lamps, thereby providing intense, bright colors during both day and night-time. Other applications include their use as pigments, coloring agents, materials for scintillators, materials for solar energy collectors, materials for light emitting electroluminescent devices, materials for generating fluorescent images as well as in printing inks. Moreover, the choice of guest compound can lend a lot of flexibility to the desired emission wavelength required of the overall system, therein imparting the capability for color-tuning and ease of tailoring of the core system to specific color applications via wavelength modulation. It is also possible to produce fluorescent images (high relief structures) by the well known photoresist technology. The compositions of the invention may also be used in paintings, lacquers or printing inks.

The compositions (a1), (a2) and (b) according to the invention may be used in various forms depending upon the end use purpose:

The composition according to the instant invention may be milled or can be produced in the form of particles. A further object of the invention is a composition in the form of particles, especially finely divided particles.

The average diameter or particle size may be 50 nm to 1000 $\mu$m, preferably 0.5 to 500 $\mu$m, more preferably 0.5 to 200 $\mu$m, most preferably 0.1 to 100 $\mu$m, and especially preferred 5 to 50 $\mu$m. The particles may be round shaped or irregularly shaped, depending on the manufacturing process, and the particles may be compact or porous. The size of the particles are commensurate to the requirements of their final application.

The compositions according to the invention may be admixed with other polymers. A further object of the invention is a composition containing (1) a blend of a non-fluorescent polymer substrate and (2) a composition (a1), (a2) or (b) according to the invention.

The amount of component (2) may be for example from 0.1 to 99.9 percent by weight, preferably 1.0 to 50 percent by weight with respect to the total composition. The amount used depends essentially on the amount of polymers with pendent host and guest chromophores in the composition and also upon the compatibility with the polymer substrate.

The non-fluorescent polymer substrates may be selected from thermoplastics, thermosettings and structurally crosslinked polymers. The admixture of thermoplastics with thermoplastics of the invention are polymeric alloys or blends. The polymers may be homopolymers, copolymers, blockpolymers, graft polymers or random polymers.

The polymers may be opaque or translucent but preferably transparent. The polymers may be selected for example from the group of thermoplastic polymers like polyesters, polyamides, polyimides, polyamide-imides, polyamide esters, polyurethanes, polyureas, polyolefines; polymers from substituted olefines like vinylethers, vinylesters, vinylalcohols, vinylchloride, vinyidichloride, acetonitrile, acrylic acid, methacrylic acid, esters and amides of acrylic acid and methacrylic acid, styrene, chlorostyrene, methylstyrene, styrene sulfonic acid and their esters and amides, vinylcarbazole, vinylpyridine, vinylpyrrolidone: polymaleic acid and esters and amides therefrom; polyethers, polysulfones, polyketones, polyphenylsulfides, and polyacetales; cellulose and its esters and ethers, and starch or derivatives of starch.

Examples of thermosetting resins and structurally crosslinked resins are polyepoxides, unsaturated polyesters, photocrosslinked resins for example from acrylic acid and/or methacrylic esters and/or amides from polyols and/or polyamines, melamine/formaldehyde resins, and phenoyformaldehyde resins; polymers from butadiene, isoprene and or chloroprene and copolymers with olefins, which may be crosslinked and of rubbery nature; as well as silicates obtainable for example through the known solgel process.

The thermoplastic compositions are for example obtainable by known mixing methods like admixing solutions of polymers and removing the solvent, injection molding and extrusion molding. Thermosetting and structurally crosslinked compositions are obtainable by known methods like press molding, whereby the composition of the invention is preferably low molecular weight and dissolved in the polymerisable mixture.

In a further aspect the composition of the invention may be used as filler for thermoplastic, thermosetting and structurally crosslinked polymers.

A further object of the invention is a composition comprising (1) a polymer substrate and (2) polymer particles of a composition (a1), (a2) or (b) according to the invention, or combinations thereof, homogeneously distributed therein.

The amount of the particles may be for example 0.1 to 90 weight %, preferably 0.1 to 70 weight % and more preferably 1 to 50 weight % of the total composition.

The polymer substrate may include those as described above. This composition can be easily prepared by known mixing methods as described above, whereby the particles are dispersed prior to the polymerization of a precursor composition.

The polymeric compositions of the invention may contain further ingredients to enhance certain features such as electrical, physical and mechanical properties, and/or the processability, for example dispersing agents to achieve a uniform distribution of particles, lubricants, plasticizers, antistatica, solvents, molding agents, antioxidants, light stabilizers, fillers and reinforcing fillers like glass balls and glass fibbers, silicates (e.g. mica, clay, wollastonite), metal and semiconductor metal oxides, metal carbonates, metal salts, metals and semiconductor metals, carbon black, as powder, or carbon fibers, whiskers, metal and semiconductor metal carbides, metal and semiconductor metal nitrides, dyes, pigments and others.

A further object of the invention is a shaped article from (1) a composition (a1), (a2) or (b) according to the invention, or (2) a composition of (2-1) a polymer substrate containing composition (a1), (a2) or (b) according to the invention, or (2-2) containing particles of the composition (a1), (a2) or (b) of the invention, alone or together with a composition of the invention, homogeneously distributed in the polymer substrate.

In another aspect the polymers and particles of a composition according to the invention may be used as coatings on carrier materials, using the above mentioned compositions.

Another object of the invention is a composition comprising (1) a carrier material and (2) at least on one surface a coating of
(i) a composition (a1), (a2) or (b) of the invention,
(ii) a polymer as a substrate containing therein homogeneously distributed particles of a composition (a1), (a2) or (b) of the invention, or
(iii) a mixture comprising a polymer as a substrate and in homogeneously distribution a composition (a1), (a2) or (b) of the invention, either alone or in admixture with particles of the composition (a1), (a2) or (b) of the invention.

Suitable carrier materials may be selected from organic or inorganic materials like glass, ceramics, minerals, plastics, paper, wood, semiconductors, metals, metal oxides and semiconductor metal oxides, and metal or semiconductor metalnitrides or -carbides.

The thickness of the coating depends on the desired use and may be from 0.1 to 1000 $\mu$m, preferably 0.5 to 500 $\mu$m, and especially preferred 1 to 100 $\mu$m.

The coatings may be protected by covering coatings which preferably are transparent. Such coatings are well known and in general photocrosslinked coatings are mainly used for this purpose and are well known in the art. Preferred coatings are transparent. Moreover, the materials belonging to compositions of the invention, which are surface modified, may also be protected by coatings.

The coated materials are obtainable by known methods like painting, casting or spincoating, directly or with a solution or dispersion of the polymeric compositions. It is also possible to use a polymerisable composition containing polymer forming monomers, especially crosslinkable olefinically unsaturated monomers. The polymerization may be induced thermally or by actinic radiation. The coating compositions are novel and a further object of the invention.

A further object of the invention is therefore a liquid and optionally a solvent containing composition, comprising
(1) a composition (a1), (a2) or (b) of the invention and optionally a non-fluorescent polymer, or
(2) a polymer substrate containing uniformly dispersed particles of a composition (a1), (a2) or (b) of the invention, alone or in admixture with a composition (a1), (a2) or (b) according to the invention.

These compositions may contain a solvent, such as those mentioned before, and optionally surfactants and dispersing agents. The viscosity range depends on the desired application for the coating wherein the desired viscosity can be achieved by choice of solvent quantity, polymers as binders and fluorescent materials. To further achieve a desired viscosity thickening agents may additionally be used. Again suitable solvents have been mentioned.

The preparation of this composition can be achieved by simply mixing the ingredients together using suitable mixing equipment. Dispersions are in general stable depending upon the viscosity. If particles should aggregate they may be redistributed by stirring.

In a highly advantageous embodiment of preparing coatings polymerisable compositions can be used, wherein at least one surface of a carrier material is coated and subsequently polymerized by heat or radiation. Photopolymerizable mixtures can also be used to generate fluorescent images by known photoresist technology.

A further preferred embodiment of the present invention is a polymerisable composition comprising
(1) polymerisable monomers or prepolymers in admixture with particles of a composition (a1), (a2) or (b) of the invention, and optionally dissolved therein a composition (a1), (a2) or (b) of the invention;
(2) polymerisable monomers or prepolymers and dissolved therein a composition (a1), (a2) or (b) of the invention;
(3a) a polymerisable host chromophore as defined herein, containing at least one polymerisable group or at least two functional groups or a prepolymer of it; optionally nonfluorescent monomers or prepolymers copolymerisable with the host chromophore; and a guest chromophore or a pigment precursor dissolved therein;
(3b) a polymerisable guest chromophore containing at least one polymerisable group or at least two functional groups, or a prepolymer thereof; optionally nonfluorescent monomers or prepolymers copolymerisable with the guest chromophore; and a host chromophore as defined herein, dissolved therein.

The composition may be used to generate the composition (a1), (a2) or (b) of the instant invention as described before. Preferably the composition contains a solvent, when coatings or images are to be generated. The afore described embodiments also apply to this composition, inclusive of the preferred embodiments.

In a preferred embodiment the composition is based on polymerisable monomers and/or prepolymers containing a group selected from olefinically unsaturated groups, preferably from —CH=CH$_2$ and —C(CH$_3$)=CH$_2$, which can be thermally or photo-polymerized.

Photopolymerisable monomers and prepolymers are well known in the art and described for example in EP-A-0 654 711. Preferred photopolymerisable monomers and prepolymers are those based on the esters or amides of acrylic acid or methacrylic acid and alcohols, polyols, amines and polyamines.

The photopolymerisable composition is particularly suitable to generate coatings and images.

A further preferred embodiment of the present invention relates to a composition comprising (1) a carrier material and (2) a high relief image of a polymerized photoresist material on at least one surface of the carrier, which contains (2-1) particles of a composition of the invention in uniform distribution; or dissolved and homogeneously distributed therein a composition (a1), (a2) or (b) of the invention; or both; or (2-2) wherein the photoresist is composed of a polymer obtainable from (c1) a photopolymerisable host chromophore as defined herein, containing at least one photopolymerisable group or at least two functional photoreactive groups or a prepolymer of it; optionally non-fluorescent monomers or prepolymers copolymerisable with the host chromophore; and a guest chromophore or a pigment precursor dissolved therein;

(c2) a photpolymerisable guest chromophore containing at least one photopolymerisable group or at least two functional photoreactive groups or a prepolymer of it; optionally non-fluorescent monomers or prepolymers copolymerisable with the guest chromophore; and a host chromophore as defined herein, dissolved therein.

A further preferred embodiment of the present invention relates to a a process for the preparation of fluorescent high relief images on a carrier, which involves irradiating under a mask or by laser writing, the above dried coated photopolymerisable composition on the carrier, developing the irradiated composition and finally removing the non-irradiated parts.

Removal of the non-irradiated parts is preferably carried out by treatment with solvent.

A further preferred embodiment of the present invention relates to a process for the creation of fluorescent radiation which requires the excitation either electrically or by UV or visible irradiation, or both, of a fluorescent composition (a1), (a2) or (b) according to the invention. Another preferred embodiment of the present invention relates to the use of the compositions (a1), (a2) and (b) according to the invention as fluorescent materials.

All the materials described before are highly fluorescent materials according to observations hitherto which can broadly be used in optical and electroptical devices.

The compositions on hand do show the following advantages if compared to corresponding compositions of the prior art:

i) an intense solid state fluorescence is imparted, wherein the emission wavelengths are in the in the visible region of the electromagnetic spectrum, ii) high ratios of host and guest molecules can be incorporated as part of the polymer whilst retaining solid-state fluorescence properties (i.e. negligible concentration quenching), iii) the compositions can be excited using wavelengths in both the UV and visible regions, iv) very excellent photostabilities can be achieved, v) a wide range emission wavelengths can be achieved through selection of guest molecules (color tuning), vi) a high thermal stability can achieved, vii) soluble and insoluble fluorescent compositions can be generated, viii) migration of fluorescent host and guest molecules is essentially excluded and ix) easy preparation for the materials i.e. single pot reactions are possible.

The present invention will now be described by way of examples.

A) Preparation of Host Chromochores and/or Host Monomer/Polymer Intermediates.

EXAMPLE A1

1,2,3,4 Tetraphenyl-7-(carboxylic acid)-benzo[4,5]-imidazo[2,1-a]isoindol-11-one (A1, inclusive the corrsponding 8-isomer)

Into a reaction vessel equipped with a condenser, light nitrogen purge and magnetic stirrer, 10 g (0.022 mol) of tetraphenylphthalic anhydride and 3.35 g (0.022 mol) of 3,4-diaminobenzoic acid are added, along with 100 ml of acetic acid. The gray colored reaction mixture is heated to reflux temperature. After several hours the reaction begins to take-on a dark yellow color. The reaction mixture is then left for a further 72 hours at slightly below reflux temperature (105° C.).

The bright yellow precipitate is filtered and washed with water and methanol. The yellow product is then left to dry at the water aspirator before final drying in a vacuum oven overnight (60° C.). The obtained yield is 81%.

EXAMPLE A2

1,2,3,4 Tetraphenyl-benzo[4,5]-imidazo[2,1-a] isoindol-11-one-7-carboxylic Acid Chloride (A2, inclusive the 8-isomer)

Into a reaction vessel equipped with a condenser, light nitrogen purge and magnetic stirrer, 5 g (0.0088 mol) of compound A1 and 30 ml of dry benzene are added. Keeping at room temperature, a molar excess of thionyl chloride is added to the reaction mixture, which is then allowed to stir for 30 minutes. The reaction mixture, which is a yellow suspension, is then heated to reflux temperature for about 2 hours, to yield a clear golden colored solution. The solvent and excess thionyl chloride are removed using a stream of nitrogen, to furnish the yellow acid chloride derivative. The yield is 94%.

B) Preparation of Polymerisable Host Derivatives

EXAMPLE B1

1,2,3,4 Tetraphenyl-benzo[4,5] imidazo[2,1-a] isoindol-11-one-7-carboxy Ethyl Methacrylate (B1, inclusive the 8-isomer)

4 g of A2, dissolved in 30 ml of dry pyridine are added slowly over the period of about 30 minutes, to a stirred solution containing 5 g (large excess) hydroxy ethyl methacrylate in 10 ml of dry pyridine at room temperature. The reaction mixture is left at room temperature to stir for a further 2 hours.

The completed reaction mixture is then slowly added, with stirring, to a beaker containing 100 g of ice and 100 ml of 1M HCl. A yellow precipitate is obtained and allowed to settle before filtration (sinter glass G3), by vacuum pumping, to yield the crude product. The crude precipitate is further purified, to remove residual hydroxyethyl methacrylate, by reprecipitation from chloroform into a large excess of hexane (Yield 86%).

C) Preparation of Functionalized Guest Compounds

EXAMPLE C-1

Carboxy Ethyl Methacrylate Derivative of Rhodamine-B (C-1)

Into a reaction vessel equipped with a condenser, light nitrogen purge and magnetic stirrer 3.5 g (0.0073 mol) of rhodamine-B are added to about 30 ml of anhydrous dichloromethane (Aldrich Special Grade). Whilst keeping at room temperature 1.54 g (0.0095 mol, 1.3 excess) of N,N'-carbonyl diimidazole is added over the period of about 10 minutes to the vigorously stirred rhodamine solution. This reaction is left to stir for a further 4 hours at room temperature to afford the desired acid imidazole.

A three times equivalent amount of 2-hydroxyethyl methacrylate (2.8 g, 0.022 mol) is then added to the reaction mixture and allowed to stir for a further 72 hours at room temperature. The solvent is removed from the crude reaction mixture, and the product purified by column chromatography. 90CHCl$_3$/10MeOH is employed as the eluting solvent.

EXAMPLE C-2

Preparation of multifunctional diketopyrrolopyrole compounds similar to C2 below can be achieved by methods described in EP-A 337 951 or preferably as described in example 12 of EP-A 787 731.

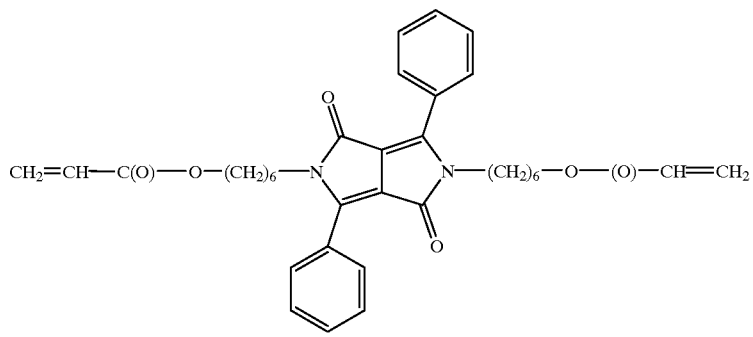

D) Preparation of Fluorescent Polymers

EXAMPLE D-1

Preparation of Host Chromophore Containing Polymer via the Radical Polymerisation of a Host Chromorhore Containing Monomer Into a clean 50 ml reaction flask, 2.04 g of host monomer B1, 1.7 g of methyl methacrylate, 0.0172 g of recrystallized AIBN and 12 ml of chloroform are added. The reaction mixture is removed of oxygen by bubbling with N$_2$ gas for approximately 30 minutes. The reaction mixture is placed in a temperature controlled water bath at 60° C. and terminated when the viscosity of the reaction solution is significantly increased (8 hours). The polymer is isolated by a series of reprecipitations using chloroform and methanol (or hexane) as the solvent and non-solvent combination respectively. Yield 53%, Mw 2.5×10$^5$.

EXAMPLE D2

Preparation of Guest Chromophore Containing Polymer via the Radical Polymerisation of a Guest Chromophore Containing Monomer The monomer feed reaction mixture containing 0.06 g of guest monomer C1, 9.14 g of methyl methacrylate and 0.8 g of hydroxyethyl methacrylate is added to a clean reaction flask, along with 0.04 g of recrystallized 2,2'-azobisisobutyronitrile (AIBN) and 30 ml of chloroform as the polymerisation solvent. After 10 hours at 60° C. a copolymer of Mw ~2.6•10$^5$ is obtained. Yield 47%.

In the following, photoluminescence and excitation spectra of all fluorescent polymer samples were recorded using a Hitachi F-4500 Fluorescence Spectrophotometer in the standard reflectance mode, with the aid of a commercial solid sampler that possess a transparent quartz window. Polymer samples were cast onto glass slides and removed of solvent prior to measurement. The scan rate was 240 nm/min.

EXAMPLE E-1

Preparation of Host/Guest Polymer Alloy

The host polymer of Example D1 and the guest polymer of D2 are dissolved in common solvent (chloroform) such that ratio of solids to solvent is 5 w/v/ %. The weight ratio of the host polymer to the guest polymer is 50:50. After complete mixing, the solution is spread by aid of a bar coater to form a uniform polymer film of the order of c.a. 2 microns.

The absorption and fluorescence characteristics of the host/guest system and its individual components are tabulated in Table 1 below.

TABLE 1

| Host Polymer (wt %) | Guest Polymer (wt %) | AbsMax (nm) | ExMax (nm) | EmMax (nm) | PI Ratio (Enhancement Factor) |
|---|---|---|---|---|---|
| 100 | 0 | 365 | 365 | 501 | 1 |
| 0 | 100 | 560 | 560 | 580 | — |
| 50 | 50 | 365 | 365 | 580 | 2.5 |

(PI; maximum peak intensities, AbsMax; absorption maximum, ExMax; experimental excitation maximum, EmMax; experimental emission maximum).

EXAMPLE C-2

Preparation of Molecular Dispersion of Small Molecule Guest in a Polymer with Covalently Attached Host Molecules A host polymer of Example D1 is mixed with Rhodamine 19 perchlorate (Laser Grade) in a common solvent (95 CH$_2$Cl$_2$/5 CH$_3$OH), such that ratio of solids to solvent was 5 w/v %. The weight ratio of host polymer to guest molecule is 99.8: 0.2. After complete mixing, the solution is spread by aid of a bar coater, to form after solvent removal a polymer film of the order of 2 microns in thickness.

The absorption and fluorescence characteristics of the host/guest system and its individual components are tabulated in Table 2 below:

TABLE 2

| Host (wt %) | Guest (wt %) | AbsMax (nm) | ExMax (nm) | EmMax (nm) | PI Ratio (Enhancement Factor) |
|---|---|---|---|---|---|
| 100 | 0 | 65 | 365 | 501 | — |
| 0 | 0.2# | 560 | 560 | 580 | — |
| 99.8 | 0.2 | 365 | 365 | 580 | 2.7 |

[# matrix is a non-fluorescent polymer Polymethylmethacrylate (PMMA)].
(PI; maximum peak intensities, AbsMax; absorption maximum, ExMax; experimental excitation maximum, EmMax; experimental emission maximum).

EXAMPLE E-3

Molecular Dissolution of Small Molecule Host in a Polymer with Covalently Attached Guest Molecules A guest polymer of Example D2 is mixed with host molecule. The host molecule is prepared in accordance with Example A1, except that the diamine employed is 4-tert-butyl-1,2-diaminobenzene (i.e. 1,2,3,4-tetraphenyl-7(or8)-(2'-methyl-2-propyl)-benzo[4,5]-imidazo[2,1-a]isoindol-11-one). The guest polymer is mixed with the host molecule by dissolving in a common solvent (95CH$_2$Cl$_2$/5CH$_3$OH), such that ratio of solids to solvent is 5 w/v %. The weight ratio of guest polymer to host molecule was 50:50. After complete mixing, the solution was spread by aid of a bar coater to form a uniform polymer film of the order of 2 microns in thickness.

The absorption and fluorescence characteristics of the host/guest system and its individual components are tabulated in Table 3 below:

TABLE 3

| Host (wt %) | Guest Polymer (wt %) | AbsMax (nm) | ExMax (nm) | EmMax (nm) | PI Ratio |
|---|---|---|---|---|---|
| 50# | 0 | 365 | 365 | 501 | 1 |
| 0 | 100 | 560 | 560 | 580 | — |
| 50 | 50 | 365 | 365 | 580 | 8.9 |

(# a polymer film of 50:50 wt % [1,2,3,4-tetraphenyl-7(or8)-(2'-methyl-2-propyl)-benzo[4,5]imidazo[2,1-a]isoindol-11-one/PMMA)].
(PI; maximum peak intensities, AbsMax; absorption maximum, ExMax: experimental excitation maximum, EmMax; experimental emission maximum).

EXAMPLE E-4

Molecular Solution of Small Latent Guest Molecules in a Polymer with Covalently Attached Host Molecules A host polymer of Example D1 is mixed with latent guest molecules. A mixture of 0.1 g of the host polymer and 0.0001 g of pigment precursor N,N'-bis-tert-butoxycarbonyl-1,4-diketo-3,6-diphenyl-pyrrolo-[-3,4-c] pyrrole ("Boc-DPP", prepared in analogy to the method described in EP-A 654 711) is prepared by dissolving both components in chloroform, such that the weight to volume ratio is 5 w/v %. A portion of the solution is cast onto a glass slide and spread by the aid of a bar coater, creating a film of about 2 microns in thickness. This film is then heated on a hot plate at 120° C. for a period of 1 minute, upon which the solublizing t-Boc group is thermally removed, generating a molecular solution of the insoluble pigment 1,4-diketo-3,6-diphenyl-pyrrolo-[-3,4-c] pyrrole. The energy transfer is observed spectroscopically by a change in fluorescence emission.

The absorption and fluorescnece characteristics of the host guest system befroe and after heating are detailed in table 4 below:

TABLE 4

| | Host (wt %) | Guest (wt %) | Abs Max (nm) | Emission Max (nm) | PI Ratio (Enhancement Ratio) |
|---|---|---|---|---|---|
| Before Heat | 99.9 | 0.1 | 365 | 501 | — |
| After Heat | 99.94# | 0.06# | 365 | 508 | 1.3 |

(# the gain and loss in weight percentages for the host and guest arises from the loss of the t-Boc group of the latent guest molecule).
(PI; maximum peak intensities, AbsMax; absorption maximum, EmMax; experimental emission maximum).

What is claimed is:

1. A solid composition comprising at least one host chromophore selected from the group consisting of a benzo [4,5] imidazo[2,1-a]isoindol-11-ones and at least one guest chromophore, wherein the weight ratio between host chromophores and guest chromophores is 50:50 to 9999:1, and if desired a polymer C, wherein the emission spectrum of the host chromophore overlaps with the absorption spectrum of the guest chromophore, and wherein
   (a1) the host chromophore is covalently linked to a polymer backbone A ("host polymer"), and/or
   (a2) the guest chromophore is covalently linked to a polymer backbone B ("guest polymer").

2. (amended) A solid composition according to claim 1, characterized in that (a1) the guest chromophore is homogeneously distributed in a matrix formed by the host polymer, or (a2) the host chromophore is homogeneously distributed, preferred dissolved and homogeneously distributed, in a matrix formed by the guest polymer, or (b) the host polymer and the guest polymer are admixed, preferably homogeneously.

3. A composition according to claim 1 in the form of particles.

4. A composition comprising (1) a carrier material and (2) at least on one surface a coating of a composition according to claim 1.

5. A composition comprising (1) a carrier material and (2) at least on one surface a coating of a polymer as a substrate containing therein homogeneously distributed particles according to claim 3.

6. A composition comprising (1) a carrier material and (2) at least on one surface a coating of a mixture comprising a polymer as a substrate and in homogeneously distribution a composition according to claim 1.

7. A composition comprising (1) a carrier material and (2) at least on one surface a coating of a mixture comprising a polymer as a substrate and in homogeneously distribution a composition according to claim 1 in admixture with a composition according to claim 1 in the form of particles.

8. A polymerisable composition comprising:
   (1) polymerisable monomers or prepolymers in admixture with a composition according to claim 1 in the form of particles, and optionally dissolved therein a composition according to claim 1;
   (2) polymerisable monomers or prepolymers and dissolved therein a composition according to claim 1;
   (3a) a polymerisable host chromophore, containing at least one polymerisable group or at least two functional groups or a prepolymer of it; optionally nonfluorescent monomers or prepolymers copolymerisable with the host chromophore; and a guest chromophore or a pigment precursor dissolved therein; or (3b) a polymerisable guest chromophore containing at least one polymerisable group or at least two functional groups, or a prepolymer thereof; optionally nonfluorescent monomers or prepolymers copolymerisable with the guest chromophore; and a host chromophore dissolved therein, wherein the host chromophore is selected from the group consisting of benzo[4,5]imidazo[2,1-a]isoindol-11-one.

9. A method for making a photoresist image comprising applying a polymerisable composition containing a solid composition according to claim 1 onto a substrate and irradiating at least a portion of the polymerisable composition.

* * * * *

UNITED STATES PATENT AND TRADEMARK OFFICE
CERTIFICATE OF CORRECTION

PATENT NO. : 6,080,516
DATED : June 27, 2000
INVENTOR(S) : Brian Gerrard Devlin et al.

Page 1 of 1

It is certified that error appears in the above-identified patent and that said Letters Patent is hereby corrected as shown below:

Title page, Section [30] should read:

-- [30] Foreign Application Priority Data

| Feb 3, 1997 | (EP) Europe | 97810049.3 |
| Feb 3, 1997 | (EP) Europe | 97810050.1 |
| Feb 3, 1997 | (EP) Europe | 97810051.9 |
| Feb 4, 1997 | (EP) Europe | 97810054.3 |
| Feb 4, 1997 | (EP) Europe | 97810055.0 --. |

Signed and Sealed this

Twenty-first Day of August, 2001

*Attest:*

*Attesting Officer*

NICHOLAS P. GODICI
*Acting Director of the United States Patent and Trademark Office*